US006911314B2

(12) United States Patent
Gatanaga et al.

(10) Patent No.: US 6,911,314 B2
(45) Date of Patent: Jun. 28, 2005

(54) SCREENING FOR DRUGS THAT AFFECT TNF RECEPTOR RELEASING ENZYME

(75) Inventors: Tetsuya Gatanaga, Irvine, CA (US); Gale A. Granger, Laguna Beach, CA (US)

(73) Assignee: The Regents of the University of California, Oakland, CA (US)

( * ) Notice: Subject to any disclaimer, the term of this patent is extended or adjusted under 35 U.S.C. 154(b) by 330 days.

(21) Appl. No.: 09/752,639

(22) Filed: Dec. 29, 2000

(65) Prior Publication Data

US 2002/0091243 A1 Jul. 11, 2002

Related U.S. Application Data

(63) Continuation of application No. 09/712,813, filed on Nov. 13, 2000, which is a continuation of application No. PCT/US99/10793, filed on May 14, 1999.

(51) Int. Cl.$^7$ ...................... G01N 33/566; C12N 15/12; C12N 15/63; C12Q 1/68; C07K 14/00

(52) U.S. Cl. .................. 435/7.2; 435/6; 435/320.1; 435/325; 530/350

(58) Field of Search ................ 435/7.2, 69.1, 435/320.1, 325, 6; 530/350

(56) References Cited

U.S. PATENT DOCUMENTS

| | | | |
|---|---|---|---|
| 4,761,371 A | 8/1988 | Bell et al. | |
| 5,945,397 A | 8/1999 | Smith et al. | |
| 6,083,913 A | 7/2000 | Dower et al. | |
| 6,413,741 B1 | 7/2002 | Jegla et al. | |

FOREIGN PATENT DOCUMENTS

WO   PCT WO 98/20140   5/1998

OTHER PUBLICATIONS

Katsura K, Park M, Gatanaga M, Yu EC, Takishima K, Granger GA, Gatanaga T. Identification of the proteolytic enzyme which cleaves human p75 TNF receptor in vitro. Biochem Biophys Res Commun. May 15, 1996;222(2):298–302.*
Katsura, K et al. Identification and characterization of soluble TNF receptor releasing enzyme (TRRE) from PMA-stimulated human monocytic THP-1 cells. Proceedings of the AACR Annual Meeting, (1996) vol. 37, No. 0, pp. 492. Meeting Info.: Washington, D.C.*
Bjornberg F et al. Metalloproteases and serineproteases are involved in the cleavage of the two tumour necrosis factor (TNF) receptors to soluble forms in the myeloid cell lines U–937 and THP–1. Scand J Immunol. Oct. 1995;42(4):418–24.*
Voet et al. Biochemistry. 1990. John Wiley & Sons, Inc.. pp. 126–128 and 228–234.*

Aderka et al. "Increased serum levels of soluble receptors for tumor necrosis factor in cancer patients." Cancer Res. 51:5602, 1991.
Aggarwal et al. "Characterization of receptors for human tumour necrosis factor and their regulation by gamma-interferon." Nature 318:665, 1985.
Baglioni et al. "Binding of human tumor necrosis factor to high affinity receptors on HeLa and lymphoblastoid cells sensitive to growth inhibition." J. Biol. Chem. 260:13395, 1985.
Brakebusch et al. "Cytoplasmic truncation of the p55 tumour necrosis factor (TNF) receptor abolishes signaling, but not induced shedding of the receptor." EMBO J. 11:943, 1992.
Diez–Ruiz et al. "Soluble receptors for tumour necrosis factor in clinical laboratory diagnosis." Eur. J. Haematol. 54:1, 1995.
Grosen et al. "Measurement of the soluble membrane receptors for tumor necrosis factor and lymphotoxin in the sera of patients with gynecologic malignancy." Gynecol. Oncol. 50:68, 1993.
Gullberg et al. "Involvement of an Asn/Val cleavage site in the production of a soluble form of a human tumor necrosis factor (TNF) receptor. Site-directed mutagenesis of a putative cleavage site in the p55 TNF receptor chain." Eur. J. Cell Biol. 58:307, 1992.
Halwachs et al. "Serum levels of the soluble receptor for tumor necrosis factor in patients with renal disease." Clin. Invest. 72:473, 1994.
Holtmann & Wallach. "Down regulation of the receptors for tumor necrosis factor by interleukin 1 and 4 beta-phorbol-12-myristate-13-acetate." J. Immunol. 139:1161, 1987.
Kochi et al. "Characterization and affinity crosslinking of receptors for tumor necrosis factor in human cells." Arch. Biochem. Biophys. 249:263, 1986.
Kull et al. "Cellular receptor for 125I-labeled tumor necrosis factor: specific binding, affinity labeling, and relationship to sensitivity." Proc. Natl. Acad. Sci. USA 82:5756, 1985.
Porteu et al. "Shedding of tumor necrosis factor receptors by activated human neutrophils." J. Exp. Med. 172:599, 1990.
Redl et al. "Tumor necrosis factor (TNF) dependent shedding of the p55 TNF receptor in a baboon model of bacteremia." Infecl. Immun. 63:297, 1995.

(Continued)

*Primary Examiner*—Lorraine Spector
*Assistant Examiner*—Joseph F. Murphy
(74) *Attorney, Agent, or Firm*—Carol L. Francis; Bozicevic, Field & Francis LLP

(57) ABSTRACT

The biological effects of the cytokine TNF are mediated by binding to receptors on the surface of cells. This disclosure describes new proteins and polynucleotides that promote enzymatic cleavage and release of TNF receptors. Also provided are methods for identifying additional compounds that influence TNF receptor shedding. As the active ingredient in a pharmaceutical composition, the products of this invention increase or decrease TNF signal transduction, thereby alleviating the pathology of disease.

29 Claims, 5 Drawing Sheets

OTHER PUBLICATIONS

Schall et al. "Molecular cloning and expression of a receptor for human tumor necrosis factor." [Relation between membrane TNF–R and the soluble form] Cell 61:361, 1990.

Yonehara et al. "A cell–killing monoclonal antibody (anti–Fas) to a cell surface antigen co–downregulated wtih the receptor of tumor necrosis factor." J. Exp. Med. 169:1747, 1989.

Yoshie et al. Binding and crosslinking of 125I–labeled recombinant human tumor necrosis factor to cell surface receptors. J. Biochem. (Tokyo) 100:531, 1986.

(2000) "ENBREL(R) (etanercept) U.S. and European Long–Term Clinical Trial Data Presented at the Annual Meeting of the European League Against Rheumatism." *Company News On–Call* http://www.prnewswire.com/cgi-bin/stories.pl?ACCT=105&STORY=/www/story/(Jun. 23, 2000)/0001250565.

(2000) "Immunex Reports Second Quarter 2000 Results." *Immunex Investor Relations* http://www.immunex.com/investor/pressreleases/pr000719.html (Jul. 19, 2000).

Lesslauer, et al., "Recombinant soluble tumor necrosis factor recepotr proteins protect mice form lipopolysaccharide–induced lethality." *Eur. J. of Immunol.* (1991) vol. 21:2883–2886.

Mohler, et al., "Soluble tumor necrosis factor (TNF) receptors are effective therapeutic agents in lethal endotoxemia and function simultaneously as both TNF carriers and TNF Antagonists," *J. of Immunol.* (Aug. 1, 1993) vol. 151(3):1548–1561.

Trehu, et al., "Phase I trail of interleukin 2 in combination with the soluble tumor necrosis factor receptor p75 IgG chimera," (Aug. 1996) vol. 2:1341–1351.

* cited by examiner

SEQUENCE LISTING (1) GENERAL INFORMATION:

(iii) NUMBER OF SEQUENCES: 154

(2) INFORMATION FOR SEQ ID NO:1:

(i) SEQUENCE CHARACTERISTICS:
        (A) LENGTH: 4047 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:1:

```
AAGCTTTTTG CTTTCCTTCC CCGGGAAAGG CCGGGGCCAG AGACCCGCAC TCGGACCAGG     60
CGGGGGCTGC GGGGCCAGAG TGGGCTGGGG AGGGCTGGGA GGGCGTCTGG GGCCGGCTCC    120
TCCAGGCTGG GGGCCGCCAG CTCCGGGAAG GCAGTCCTGG CCTGCGGATG GGGCCGCGCG    180
TGGGGCCCGG CGGGGCGGCC TCGGGAGGCG TCCAGGCTGC GGGAGCGGGA GGAGCGGCCG    240
TGCGGGCGCC AGCGCCGTGG GTGGAGGTCG CCGTCCCTCC TGAGGGGCAG CCAGTGCGTT    300
TGGGACCCGG GAGCAGAGCC CGCGCCTCCC CAGCGGCCTC CCCGGGGGTC TCACCGGGTC    360
ACCCGAGAGC GGAGGCCCCG GCTCCGCAGA AACCCGGGGC GGCCGCGGGG AAGCAGCGCC    420
CTCAGGCGTC GGAGGAGCCC CCAGAAGGAC CTCGCGCCTT CCCGCCGGGC TCCGACCGCC    480
TGGGTTCGGT GCGGGACGGC CCAGGCCGCC AGGACCCCCA AGCGCAGCTC AGTCTGCGGG    540
GCACGACCCA GAGGCCAGCA GCAGAGGACG GGGCCGGGGC CGGAGAGGGG CGGGGAGGGC    600
GCTCCTGGGA GGTCAAGGCC AGGGCTAGAC TTTCAGGGTC ATGGCCTGGC CCCTCATCCC    660
CAGGGAGGTG AGGGGGCTCT GTGAGCAGAG GGGGCCCCGG TGGAGAAGGC GCTGCTAGCC    720
AGGGGCGGGG CAGGAGCCCA GGTGGGGACT TAAGGGTGGC TGAAGGGACC CTCAGGCTGC    780
AGGGATAGGG AGGGAAGCTA GGGGTGTGGC TTGGGGAGGT GCTGGGGGAC CGCGGGCGCC    840
CTTTATTCTG AAGCCGAATG TGCTGCCGGA GTCCCCAGTG ACCTAGAAAT CCATTTCAAG    900
ATTTTCAGGA GTTTCAGGTG GAGACAAAGG CCAGGCCCAG GTGAAAATGT GGCAGTGACA    960
GAGTATGGGG TGAGAACCAC GGAGAGAGGA AGTCCCCGAG GCGGATGATG GGACAGAGAG   1020
CGGGGACCAG AATTTTTTAA AACGCATCTG AGATGCGTTT GGCAGACTCA TAGTTGTTTT   1080
CCTTTCACGG AGAAAGTGTG GGCAGAAGCC AGCTCTAAAG CCCAGGCTGC CCAGCCTGCA   1140
CTGGCAGAGC TGACGGAAGG CCAGGGCAGA GCCTTCCCTC CCTGTCACAG ACATGAGCCC   1200
TGGAGATCTG GAATGAGGCA GATGTGCCCA GGGAAAGCTG ATCCGCCCCG ACCCAGGGCC   1260
CCCCGGGTGC CCCTTTGAGC GTGGAATCGT TGCCAGGTCA TGGCTCCCTG CTATCGAACA   1320
CCGGACACGG GTCGTGTGCT GCACCTGGCA GTTGCAGGAC CGACACCCAC AATGCCTTAA   1380
GAGGTGATGA CTGCCTTCCA GGGGCCTGGC TGGCTGACAC TTTGCATGGC TCCTGGAGAA   1440
GAGGGATTGA GTGGAGTCCA CGGGTCATGG CCACGTCCTG GGTGCTGCCT CTGAGGCAGG   1500
GCCCGGCTGG GGTGAGAAGG GGCTGGAGAC AGGTTCCTGC CAGTTCAGCC TCTAACCGGT   1560
GGTCTTCATG CCTAGGAACC CACTGGGGGC TTATGAAACT GCAGGTGGCT GAGTCCTTGC   1620
CATGGGGTCT CTCCTTCAGG AGGTCTGGGT GGGGCCGGAG ACTGTACCCC ACAAAGGGTC   1680
CCAGGTGAGG CGGATGTGGC CTGGCGCTGT GTGGCTCTGG ACCTAGTCCT TGGGCTTGGG   1740
CTGGCGCCCA GGGCCTGGGC TTGAGACAGC TGTGACGCAG GCAAGCCATT TACCCCGTTT   1800
```

-continued

```
GTGGGGACAT TACATCTTCC TAGCTTGGAA CACACAGGCA GCCAGGGTTG TTATCCACAT       1860

TCCTCCTCCA TGTTCTTCTC TTGAGAACTT TTACCAGGTA TGTCAGGAGC TGGGCTCCAC       1920

CAGGGAGACT CAAGTGGAAA GCCCTCATCC TTGTCCTCCA GGAGACAGGA AAACCTATGG       1980

TTACAATTCC AGGGACAAGA GCGATGCATG TGAGGTGTGG CAAATCTCAC TGTTCAACTG       2040

GAGAAATCAG AGACAGCTTC CTGGAGGCAG TGACACCTGG ACAGGCTTCT CCACAGGAGG       2100

AAGCGAGTGA GAGAAGCCAA CTGGGATGGA CCCATCATGT AGGGGAACA GTGCGCGCAG        2160

AACCAACAAC CACCCCCACC CTAGGCCCAG AGCTCACGGA GAGAGCTGGG CCTCTCGGGG       2220

TGACTACATA GTTCCCTGCT GGATCTTAGG TCTTGTCCTT GGGCAGCTCT GCTGAGACCT       2280

CTATGCCTGT TCCAGGCTGC ACCAAGGTTT TGTGACTATT GGTCTGGGGT TGTTTTGCAG       2340

CAACTGAAGT GTTCTGTTGT AAAACAGGCA CTTGATTTGC TGGAAGGAAT GCTGTTTGTT       2400

CTTGCTGCGA CAAACATTGA GCAGCATTTA GTGGGCGGTT TATATCTTGT GGAGTAATGG       2460

GTGTTTTTGA AGTCTGTCCT GGGTACTGCA CATTAAAAGG AATATCATTT TCTGAAACAT       2520

TGCTATTTTC CACACCAGAA ATCATATCCT CTTGCTGGTC CATGTCTGAA GACCTTACAC       2580

GAGAAAGTCT TAATGTAAGT TTAGTAGAGT CCTTGGATGG AGAACTAATT ATATCATACA       2640

TTGCCGCTTT CTCACTCTGC TCTTTTTCAT CCTTGCCTAA TTTCATTTTC TTCTGCTTCT       2700

TTTGTTTTCT TTCTGGAGAA TCTAGCAAGA TATCTGGTGG AACATCTCGA GGTGATGAAC       2760

AAGGTAGAGA CTGAGATTGT AGGATTAAAG GTGGTCTTGA GCCTTTAGGA GTTCCTTCAC       2820

TTCCAGCAGG GGAGCATACT GGCTGTGGAG ATCTCAAGGG AAAAGATGCA GCATTCCTCA       2880

TTGTTGAAGA ATCTCCATCG TCACTACTTA GCCTGTGCAC CATGTGTAGG TAGTCCTCAC       2940

TTGAACCATG TCTAGGATTA TCAGCATGAT GATTAGCTGA ATTGCCAGAC AACGGACCAG       3000

AAACTTTATT ATCATGTATG TTTCTCAAAC CACCTGCAAC AATGGGACTT GATACCGATG       3060

CTTGTTGCAT CTGTGGATGT GTTGTGTAAC TTGAAGGATG GGAATATGGC ATGTATCCTG       3120

CAGGGCTTTG TGGGGCGTAT GGACTAGGCA CTGGGCTATT TTGCTGTGGC ATAAATCTGT       3180

TCCCAGAGCT TGTCTGTGGT GGCACAAACC GGCTGGAGGG GCTATGTGAG ATAGTGGTTT       3240

GTTGATAATT GGAAGATGCA GGACTACTGT GCATGGAATT CTGAGAAAGT TTATACTGAG       3300

ACATCATCAT TCCACTTTGT ACATATCTGT TCTGCATGCT TTTCTCCCTG AAAACATTAG       3360

GACTCCTTGC CAGGACGGCC TGCAACAAGA CTGGTATGTC ACCTTCTGGG TCATCACTGC       3420

CAAGGTTATC TTTCAACTCT ATGTGATCTG TTGATACCTG GTTGAGGCTA TGGACAAGCT       3480

GTGAAACCAA ATTGTCATCC CTACAAGCCA AAAGGCAGTT CACCTCTTCT GCTATTCGTG       3540

CATTAAAGAG AAGGCTCTTT GTAGTTGTAG CAGGTAAAGG AGATGGAAGA GGCAGCTGGT       3600

TCAGGAGGTC TGTGAGACTA GCAATCCCCG CAAGAGTAGT AATGGGACA TGGGCATAT        3660

CCCCATTCAT CCTGAATTTC TGGAATGGTG TTGCCTATAA AAGTACTTAG TTCAGGTGCC       3720

AGCTGTCATT ACTTCCCATT TCCCAAACAC TGGGCGAATC GGCGTCTGAA TCCAAGGGGA       3780

GGCCGAGGCC GCTGTGGCGA GAGACTATAA TCCGGGCCGG GAGGGGGGC GGCTACGGCT        3840

CCTCTTCCGT CTCCTCAGTG CGGGGAACAT GTAGAGCCGG GGGGAGACCA GCCGAGAAGA      3900

CAAATCGTTG CTTCTTCTTC CTCCTCCTCC TCCTTCTCCC ACATAGAAAC ACTCACAAAC      3960

ACCCGACCAC GGGCCCGAGC TACCGGGGGG GCATCGCCGC GGGCCCGGGA ACCAATTCTC      4020

CTGTCGGCGG GGGCGTCCTT TGGATCC                                         4047
```

(2) INFORMATION FOR SEQ ID NO:2:

```
    (i) SEQUENCE CHARACTERISTICS:
        (A) LENGTH: 739 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:2:

GGATCCAAAG GTCAAACTCC CCACCTGGCA CTGTCCCCGG AGCGGGTCGC GCCCGGCCGG        60

CGCGCGGCCG GGCGCTTGGC GCCAGAAGCG AGAGCCCCTC GGGGCTCGCC CCCCCGCCTC       120

ACCGGGTCAG TGAAAAAACG ATCAGAGTAG TGGTATTTCA CCGGCGGCCC GCAGGGCCGG       180

CGGACCCCGC CCCGGGCCCC TCGCGGGGAC ACCGGGGGGG CGCCGGGGGC CTCCCACTTA       240

TTCTACACCT CTCATGTCTC TTCACCGTGC CAGACTAGAG TCAAGCTCAA CAGGGTCTTC       300

TTTCCCCGCT GATTCCGCCA AGCCCGTTCC CTTGGCTGTG GTTTCGCTGG ATAGTAGGTA       360

GGGACAGTGG GAATCTCGTT CATCCATTCA TGCGCGTCAC TAATTAGATG ACGAGGCATT       420

TGGCTACCTT AAGAGAGTCA TAGTTACTCC CGCCGTTTAC CCGCGCTTCA TTGAATTTCT       480

TCACTTTGAC ATTCAGAGCA CTGGGCAGAA ATCACATCGC GTCAACACCC GCCGCGGGCC       540

TTCGCGATGC TTTGTTTTAA TTAAACAGTC GGATTCCCCT GGTCCGCACC AGTTCTAAGT       600

CGGCTGCTAG GCGCCGGCCG AAGCGAGGCG CCGCGCGGAA CCGCGGCCCC CGGGGCGGAC       660

CCGCGGGGGG GACCGGGCCG CGGCCCCTCC GCCGCCTGCC GCCGCCGCCG CCGCCGCGCG       720

CCGAAGAAGA AGGGGGAAA                                                   739

(2) INFORMATION FOR SEQ ID NO:3:

(i) SEQUENCE CHARACTERISTICS:
        (A) LENGTH: 233 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:3:

CAAGAGTGGC GGCCGCAGCA GGCCCCCCGG GTGCCCGGGC CCCCCTCGAG GGGGACAGTG        60

CCCCCGCCGC GGGGGCCCCG CGGCGGGCCG CCGCCGGCCC CTGCCGCCCC GACCCTTCTC       120

CCCCCGCCGC CGCCCCCACG CGGCGCTCCC CCGGGGAGGG GGGAGGACGG GGAGCGGGGG       180

AGAGAGAGAG AGAGAGAGGG CGCGGGGTGG CTCGTGCCGA ATTCAAAAAG CTT             233

(2) INFORMATION FOR SEQ ID NO:4:

(i) SEQUENCE CHARACTERISTICS:
        (A) LENGTH: 2998 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:4:

GGATCCAAAG AATTCGGCAC GAGGTAGTCA CGGCTCTTGT CATTGTTGTA CTTGACGTTG        60

AGGCTGGTGA GCTTGGAAAA GTCGATGCGC AGCGTGCAGC AGGCGTTGTA GATGTTCTGC       120

CCGTCCAGCG ACAGCTTGGC GTGCTGGGCG CTCACGGGGT CCGCATACTG CAGCAGGGCC       180

TGGAACTGGT TGTTCTTGGT GAAGGTGATG ATCTTCAACA CTGTGCCGAA CTTGGAGAAA       240
```

```
ATCTGGTGCA GCACATCCAG GGTCACAGGG TAGAAGAGGT TCTCCACGAT GATCCTGAGC    300

ACGGGGCTCT GCCCGGCCAT CGCCATCCCT GCATCCACGG CCGCCGCCGA GGCAGCCAAG    360

GCCAGGTTCC CCGACTGGAC CGAGTTCACC GCCTGCAGGG CCGCCTGGGC CCGCGCCTGG    420

TTGGGAGAGC TGTCGGTCTT CAGCTCCTTG TGGTTGGAGA ACTGGATGTA GATGGGCTGG    480

CCGCGCAGCA CAGGGGTCAC CGAGGTGTAG TAGTTCACCA TGGTATTGGC AGCCTCCTCC    540

GTGTTCATCT CGATGAAGGC CTGGTTTTTC CCCTTCAGCA TCAGGAGGTT GGTGACCTTC    600

CCAAAGGGCA GCCCCAGGGA GATGACTTCC CCCTCCGTGA CGTCGATGGG GAGCTTCCGG    660

ATGTGGATCA CTCTAGAGGG GACGCCTGCA CTTCGGCTGT CACCTTTGAA CTTCTTGCTG    720

TCATTTCCGT TTGCTGCAGA AGCCGAGTTG CTGCTCATGA TAAACGGTCC GTTAGTGACA    780

CAAGTAGAGA AAAGCTCGTC AGATCCCCGC TTTGTACCAA CGGCTATATC TGGGACAATG    840

CCGTCCATGG CACACAGAGC AGACCCGCGG GGGACGGAGT GGAGGCGCCG GAATCCTGGA    900

GCTAGAGCTG CAGATTGAGT TGCTGCGTGA CGCGAAGCGC AAGTATGAGA GTGTCCTGCA    960

GCTGGGCCGG GCACTGACAG CCCACCTCTA CAGCCTGCTG CAGACCCAGC ATGCACTGGG    1020

TGATGCCTTT GCTGACCTCA GCCAGAAGTC CCCAGAGCTT CAGGAGGAAT TTGGCTACAA    1080

TGCAGAGACA CAGAAACTAC TATGCAAGAA TGGGGAAACG CTGCTAGGAG CCGTGAACTT    1140

CTTTGTCTCT AGCATCAACA CATTGGTCAC CAAGACCATG GAAGACACGC TCATGACTGT    1200

GAAACAGTAT GAGGCTGCCA GGCTGGAATA TGATGCCTAC CGAACAGACT TAGAGGAGCT    1260

GAGTCTAGGC CCCCGGGATG CAGGGACACG TGGTCGACTT GAGAGTGCCC AGGCCACTTT    1320

CCAGGCCCAT CGGGACAAGT ATGAGAAGCT GCGGGGAGAT GTGGCCATCA AGCTCAAGTT    1380

CCTGGAAGAA AACAAGATCA AGGTGATGCA CAAGCAGCTG CTGCTCTTCC ACAATGCTGT    1440

GTCCGCCTAC TTTGCTGGGA ACCAGAAACA GCTGGAGCAG ACCCTGCAGC AGTTCAACAT    1500

CAAGCTGCGG CCTCCAGGAG CTGAGAAACC CTCCTGGCTA GAGGAGCAGT GAGCTGCTCC    1560

CAGCCCAACT TGGCTATCAA GAAAGACATT GGGAAGGGCA GCCCCAGGGT GTGGGAGATT    1620

GGACATGGTA CATCCTTTGT CACTTGCCCT CTGGCTTGGG CTCCTTTTTC TGGCTGGGGC    1680

CTGACACCAG TTTTGCCCAC ATTGCTATGG TGGGAAGAGG GCCTGGAGGC CCAGAAGTTG    1740

CTGCCCTGTC TATCTTCCTG GCCACAGGGC TTCATTCCCA GATCTTTTCC TTCCACTTCA    1800

CAGCCAACGG CTATGACAAA ACCACTCCCT GGCCAATGGC ATCACTCTTC AGGCTGGGGT    1860

GTGCTCCCTG ACCAATGACA GAGCCTGAAA ATGCCCTGTC AGCCAATGGC AGCTCTTCTC    1920

GGACTCCCCT GGGCCAATGA TGTTGCGTCT AATACCCTTT GTCTCTCCTC TATGCGTGCC    1980

CATTGCAGAG AAGGGGACTG GGACCAAAGG GGTGGGGATA ATGGGGAGCC CCATTGCTGG    2040

CCTTGCATCT GAATAGGCCT ACCCTCACCA TTTATTCACT AATACATTTT ATTTGTGTTC    2100

TCTAATTTAA AATTACCTTT TCATCTTGCT TGATTTTCCT TCAGCTAAAT TAGAAATTTG    2160

TAGTTTTTCC CCTAAAAAAT TCAATGGCAT TCTTTCTTAT AAATTACATT CTCTGATTTT    2220

CTTGTCAGCC TGCTTCAAGG AAATCCATGT GTTCAAAATG CTTGCTCGCA GTTTGCTCCA    2280

TACCAAATGG TTGCTTAACC CAAATATCTG AGCAGCAAAT TGAGCTGATC CTTCTGGAGA    2340

AAGTACGGTT GAACAGCCAA GACCACTGGG TAGTCGAAGA AAGACCACA CATCCTGAAC    2400

TCCCCAGTCT GGTGTGAGGG GAGGACAGCT GATAACTGGA TATGCAGTGT TCCCAGACAT    2460

CACTGGTCCC AAACCATTAC TTCTGCCTGC CACTGCCACA AATACAGTAG GAATGCCATC    2520

CCCTTCATAC TCAGCTTTAA TCCTCAGAGT TTCATCTGGT CCTTTATGCG CAGATGTTAC    2580

TCGAAGTTCA CATGGAATGC CAAAATTTCC ACAGGCCTTC TTGATTTTTT CACAGTGACC    2640
```

```
AAGATCAGAA GTAGAGCCCA TCAACACTAC AACCCTGCAC TGACTTTCTG ATTTCAAAAG    2700

CAACTCTACT CTCTCTGCAA CCCACTCAAA GTTTTTCTTT ACCATTTGGA GCCCTTCAGG    2760

AGTTACTTCT TTGAGGTCCC GATAAGACTG TTTGTCTTTC TGTTGGCTTC GATCTCCTGA    2820

TGGCCAGAGT CTCCAGGAAT CATTGTCAAT AACATCAGCA AGAACAATTT CTTTGGTGGT    2880

TACATCAACA CCAAATTCAA TCTTCATATC AACCAGTGTA CAATTCTGGG GCAACCAGGA    2940

TTTCTCCAGT ATTTCAAATA TAGCCTGTGT AGCATCTCGT GCCGAATTCA AAAGCTT      2998

(2) INFORMATION FOR SEQ ID NO:5:

(i) SEQUENCE CHARACTERISTICS:
        (A) LENGTH: 4152 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:5:

AAGCTTTTTG TGAAAACCCT AGGATATGTC CCCTCCCTCA CCACACCCAA CCCCCCGCCC      60

CTGCCCCAGG ACATGACGAT GCCTCACACA CACACACACA CACACATACA CACAAGGCCG     120

TGAGCTGCAC GCAGGAACAT GGGCTGCACT CACGACAACA TTGAAAAAAT ATACATTATA     180

TATGTACACC CGGGGCCCCC ACGTCCCCTC CCGTCCCCGC AGCCTGGCCA CACCAGGTCA     240

CGGAGGAGGG GCCGGGGCTG CAGGACCTCA GGACTGCAAG GGCAGGAAGG GAAACAGGAC     300

AAGAAAGGAA GGAAGTTGGA AAGGAGGGAG AAATGGGGTC CCCAGACTGA AATGGAAATG     360

AGGTGGGGCG ATCATAAGAG AAGCAGGGAC GATGGTCCAG CTGAGGGAGC CCTGCAGAGG     420

GGGAAAAGCT TCCCATGGAC AGGAGAGAGA AGGGAAGGGG AGAGGAGAGG GTTTCCTTCA     480

ATCCCACCCC CAGCCCCAGC CCCAGCCCCA GCCATTGCAA TCGTCACCCT CTCCCCAACA     540

CAGTGAGTGC TAAGGGGGCA GCTGCCATTG GGGGTAGAAA GGCAGCTGAA GTCCAGCCCA     600

CTTTCCAACC CAGCCAGCCC CAGTGCAAGG GGCACACCAG GAGCATGACA GCCCAGAAGT     660

GAGGGATGGG GGGCCGGGGG AGGGGCAGGG CGGACTCCAG AGGGCCCGCT GGGGTTTTGA     720

AATGAAAGGA GGACTGGTTC TGAAGCCTCT CTCCCTCTTG GTCTCTGTGT TCCCAGAAAG     780

TCCTTCTCCC ATGTCTGGAG TGTCTGTTTC ACCAGGGCAG AATTCCCCCT CTGCGTGGGG     840

AGAGGTGTAG GCCTTAGTAG CGGTGTGGGG GGGTCTCGAT GATGCGTCTC TCGTCGCTGC     900

TGGGGGAATC GGCCACCTCC GAGTCACTGC TGTCCTCATC CTCCTGCTGG CCCCCAACAG     960

CCCCCGTCAC ACAGGACTGC CGATTCTGGT AGGACTCCAT GGGGTTCACA ATGATGGTGA    1020

GAGCTGAGTC ATCCCAGAAG AGGTCTGGGT CCTTGGGGTC ACTGGAGGCC CCTGGAGGCC    1080

CGCCGGCCCC TGAGACGCGG CGGTGAAGGG AATGGATGCG CACCAGGCCC AGGACGACCA    1140

TGAGCACCAG GAAGCCCACG CACACCACAA TGATGAGGGT TGCGGCGCTG GGTATCATGG    1200

AGTTTCTGTG GGAGCTGGCT AGGCTGTGTC CAGCCATCTC AGGCGGGGGC TGGTGACCAC    1260

GGTGCAGGAA CTGCTGGGAG CTGAGCACGT GGCTGGGGTG GCAACCCGG TTCATGCTGT     1320

GCAGGACATT GACCTCCACG ATGAATTCAT TGCTGGAGTA ACGGCCATTC ATTTCCGAGC    1380

AGGAAAGCCG GAACTTCCTG GTGTAGAGGG CAGCTCCGTG TCGCAGCCGA TAACGAGCCT    1440

GCCTCAGGAT CTCTTCATAC ACAGTGATGC TCTCCACCCC AGCAATAGTG AGGTAGGCAG    1500

ATGTGTTGGT GAGCTCCAGC CCCCGCTGCT GCAGAGAGGT TGTGTCCAGG AGCAGGCTTT    1560

CCCGCTCGGG ATCCAGGTCA TCCCCCACCA GAGAAATTTC ACAGCCATCC AGGTTGTGCA    1620
```

```
CAATCTCATC CGACATGCGT GTGTCTGTCA CTGTGCCCTG CCAACTCTCA TCCTTTTTGG    1680

CCTCCACCTG GTGAGAAATG GAGCAGGTGA TTTGAAGATC AGGGAACAAA GGGACGCCGT    1740

TGGTTCCCTC AAAGTCCACA GCTGGGCGGG CAAAATGAGC AGTGCCACTC AGCAGGATCT    1800

GGGGGGCGTC AGGCTGAAGG ACGACCACGT AGCCCTCCAC TTCAGGGATG GAGACGCAGG    1860

ACTCTTCGCT GAAGCACTTG ACAGCAGTGG TGAGGCGCAG GGGCCTGACG CCGGGCGTGG    1920

CAAAGCGCAG AGTGTTCATG TAAGCCACAT GCTGCAGGGC ATGGTTGAAG GTCTCCACAT    1980

CATCCCCCTC CAGGGTGAGC AGGGACTGTG AGGGGTTCAC GTGGACCTTC ATGCCTTTGC    2040

CCAGGCTCTC GAAATCCCTA TAGTCCAGCC CCTCCCGACA TGCATAGAGG CACTCGATGA    2100

CCTCGCGGCT CTCCAGGCGA CCTGAGCGCA CGCTGAAACC AGCCAGGTAG CCATGGAAGT    2160

AGTGGTGGAT CGACAAAGGG TCTCCTTGGG TGGTGTCTGT ACTGTTGTCT CCCTTTTCCT    2220

TCTCTTTGTT CTTCTCCTCA GTCCAGCAGG CCCCAATCAT GAGAGCAGGC TCCCTTCGGG    2280

GTGGGTGGAT GAGGCCATTG TCATGGATGA GGGCAGGGTC GAAGGAGATG CCGTCGGTAT    2340

AGAGTGTGAC TGTGGGGAAC TCGAGGTTCA GAGCGTAGTG GTGCCACTCA TCATCACAGA    2400

CCTGCTCCAG CTTCCAGAGG AACTTGACTG GGCGGGCACT CTCAAGCAGG GGCCAGTAGA    2460

GGAAGGCAAT CCTACAGCCG TGGACAGTCA GCGAGTAGTG AGAGAAGCCG TCCTCATTCT    2520

GGACAGTGTT ACATACGATG GTTTCCTCTT CCTTCTTGCC CTTGTTGGGA GTTACGCCAT    2580

GCTTCATCCA GAAGGACAGG GTGAAGTGGT CACTGAGGCT GTCCTGGGGC CCAGAGCCCA    2640

GCCCACTGGG GCCACCCAGG GGCACCTGCA CAGCCTGGGT GCCATTGAAC CAGTAGATCA    2700

GGCTGCTGTC CTGGCTGTAG TGCACCGAGA GTCCTGCTGT CCAGTTGGCA TTGGGGCCAG    2760

GCATGGGCAA CAGATCCACT TCCCCAGTGG CAGCACCACA GAGTTTCCGC AGCGCCCGCT    2820

CTGAGTAGTT GTCACGGTCA CAGCCCTTGG CCACATGGCT GGTCTGCAGC TCTATGGTGG    2880

CCTGAATGTT CCAGAGTGGT TCATCACAGG TCTCCAGGCG GATACCAGGG AACAAAGCCA    2940

AGCTCCCAGC ACCTGGTGCA TATTCGATCC TTTTGTTCCA GCCTTGCCAG CTGGGTTTAC    3000

AGGTGGGCTT CACCTGAATC TCCACCTCAG CATCATCTGC TGCCCGCTTC TTCCCACAGT    3060

CATAAGCTGT CACTGTAAAC TTATAGAGCC TCTCACCACT GTACTGCAGC TTCTCTGTGT    3120

TCTCAATGTT CCCGTCATTG TCAATGAGGA AAGGGGTGTT GGGTGTGAGA ATCTCATAGT    3180

AGCAGATCTG GCTGTACTGG GGGGAGCAGT CACCGTCAAT GGCTTCCACC CGCAGGATGC    3240

GATCGTACAG CTTCCCCTCT GTCACAGCCG CACGATACAG CCGTTCCACA AACACTGGGG    3300

CAAACTCGTT CACATCGTTG ACCCGCACAT GCACAGTGGC CTTGTGGGAC TTCTTGGTGT    3360

TGGCCCCGTC GGGGCCCTCG CCACAGTCAT AGGCCTGGAT GGTGAAGGTG TGTTCCTTCT    3420

GGGCCTCGCA GTCCACAGGC TCCTTGGCCC GGATCAGCCC CTCTCCTGTC GCCTTGTCAA    3480

GGATCACAGC CTCAAAGGGC ACCCCAGACC CATGGAGCCG GAAGCCGCAG ATCTCACCTG    3540

CATAGCGCAG CGGGGCATCC TTGTCCAAGG CAAAGAGTGG TGGATTCAGT AGGACCGTGT    3600

TGTCATTCTC CATGACGATG CCCTGGTACT CTGCCTCAAT CCATGGCTTG TGCTTGTTGG    3660

CTTTGTTACA GGAGCAGGAC GCGAGCAGAG AGGCCAGCAG AAGGGGCAGC AGCAGGAGGG    3720

TCATGGTGCG GCGTGGGGCA GGGCAGGGCC AGGCGTTTGC CTCCCCTGGG AGCCTCCAGC    3780

CTGCGGATTC CACCTTGCGG GAGGGATACA GGGGGGGAAA ACCAAAATAA AACGTCAAAT    3840

AAATTGTGTA GGAGGAGTCC AGCTTAGGAC CGGGCCAGAG CCAGGCCAGG CTCGGGGAGG    3900

GGGCCTCTGC AGGTTCAGAG GATCACTGCT GCCACCACCG CCACCCTGGG AGCCAGTTAT    3960
```

-continued

```
TTTGCCATGG CCTTGATTGC AACAGCTGCC TCCTCTGTCA TGGCAGACAG CACCGTGATC    4020

AGGATCTCTT CTCCACAGTC GTACTTCTGC TCAATCTCCT TGCCAAGGTC TCCCTCAGGG    4080

AGACGAAGGT CCTCTCGTAC CTCCCCGCTG TCCTGGAGCA GTGATAGGTA CCCATCCTGG    4140

ATCTTTGGAT CC                                                        4152
```

(2) INFORMATION FOR SEQ ID NO:6:

(i) SEQUENCE CHARACTERISTICS:
        (A) LENGTH: 3117 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:6:

```
GGATCCAAAG ATTCGGCACG AGTGGCCACA TCATGAACCT CCAGGCCCAG CCCAAGGCTC      60

AGAACAAGCG GAAGCGTTGC CTCTTTGGGG GCCAGGAACC AGCTCCCAAG GAGCAGCCCC     120

CTCCCCTGCA GCCCCCCCAG CAGTCCATCA GAGTGAAGGA GGAGCAGTAC CTCGGGCACG     180

AGGGTCCAGG AGGGGCAGTC TCCACCTCTC AGCCTGTGGA ACTGCCCCCT CCTAGCAGCC     240

TGGCCCTGCT GAACTCTGTG GTGTATGGGC CTGAGCGGAC CTCAGCAGCC ATGCTGTCCC     300

AGCAGGTGGC CTCAGTAAAG TGGCCCAACT CTGTGATGGC TCCAGGGCGG GGCCCGGAGC     360

GTGGAGGAGG TGGGGGTGTC AGTGACAGCA GCTGGCAGCA GCAGCCAGGC CAGCCTCCAC     420

CCCATTCAAC ATGGAACTGC CACAGTCTGT CCCTCTACAG TGCAACCAAG GGGAGCCCGC     480

ATCCTGGAGT GGGAGTCCCG ACTTACTATA ACCACCCTGA GGCACTGAAG CGGGAGAAAG     540

CGGGGGGCCC ACAGCTGGAC CGCTATGTGC GACCAATGAT GCCACAGAAG GTGCAGCTGG     600

AGGTAGGGCG GCCCCAGGCA CCCCTGAATT CTTTCCACGC AGCCAAGAAA CCCCCAAACC     660

AGTCACTGCC CCTGCAACCC TTCCAGCTGG CATTCGGCCA CCAGGTGAAC CGGCAGGTCT     720

TCCGGCAGGG CCCACCGCCC CCAAACCCGG TGGCTGCCTT CCCTCCACAG AAGCAGCAGC     780

AGCAGCAGCA ACCACAGCAG CAGCAGCAGC AGCAGCAGGC AGCCCTACCC AGATGCCGC     840

TCTTTGAGAA CTTCTATTCC ATGCCACAGC AACCCTCGCA GCAACCCCAG GACTTTGGCC     900

TGCAGCCAGC TGGGCCACTG GGACAGTCCC ACCTGGCTCA CCACAGCATG GCACCCTACC     960

CCTTCCCCCC CAACCCAGAT ATGAACCCAG AACTGCGCAA GGCCCTTCTG CAGGACTCAG    1020

CCCCGCAGCC AGCGCTACCT CAGGTCCAGA TCCCCTTCCC CCGCCGCTCC CGCCGCCTCT    1080

CTAAGGAGGG TATCCTGCCT CCCAGCGCCC TGGATGGGGC TGGCACCCAG CCTGGGCAGG    1140

AGGCCACTGG CAACCTGTTC CTACATCACT GGCCCCTGCA GCAGCCGCCA CCTGGCTCCC    1200

TGGGGCAGCC CCATCCTGAA GCTCTGGGAT TCCCGCTGGA GCTGAGGGAG TCGCAGCTAC    1260

TGCCTGATGG GGAGAGACTA GCACCCAATG GCCGGGAGCG AGAGGCTCCT GCCATGGGCA    1320

GCGAGGAGGG CATGAGGGCA GTGAGCACAG GGACTGTGGG GCAGGTGCTA CGGGGCGGAG    1380

TGATCCAGAG CACGCGACGG AGGCGCCGGG CATCCCAGGA GGCCAATTTG CTGACCCTGG    1440

CCCAGAAGGC TGTGGAGCTG GCCTCACTGC AGAATGCAAA GGATGGCAGT GGTTCTGAAG    1500

AGAAGCGGAA AAGTGTATTG GCCTCAACTA CCAAGTGTGG GGTGGAGTTT TCTGAGCCTT    1560

CCTTAGCCAC CAAGCGAGCA CGAGAAGACA GTGGGATGGT ACCCCTCATC ATCCCAGTGT    1620

CTGTGCCTGT GCGAACTGTG GACCCAACTG AGGCAGCCCA GGCTGGAGGT CTTGATGAGG    1680

ACGGGAAGGG TCTTGAACAG AACCCTGCTG AGCACAAGCC ATCAGTCATC GTCACCCGCA    1740
```

-continued

```
GGCGGTCCAC CCGAATCCCC GGGACAGATG CTCAAGCTCA GGCGGAGGAC ATGAATGTCA       1800

AGTTGGAGGG GGAGCCTTCC GTGCGGAAAC CAAAGCAGCG GCCCAGGCCC GAGCCCCTCA       1860

TCATCCCCAC CAAGGCGGGC ACTTTCATCG CCCCTCCCGT CTACTCCAAC ATCACCCCAT       1920

ACCAGAGCCA CCTGCGCTCT CCCGTGCGCC TAGCTGACCA CCCCTCTGAG CGGAGCTTTG       1980

AGCTACCTCC CTACACGCCG CCCCCCATCC TCAGCCCTGT GCGGGAAGGC TCTGGCCTCT       2040

ACTTCAATGC CATCATATCA ACCAGCACCA TCCCTGCCCC TCCTCCCATC ACGCCTAAGA       2100

GTGCCCATCG CACGCTGCTC CGGACTAACA GTGCTGAAGT AACCCCGCCT GTCCTCTCTG       2160

TGATGGGGGA GGCCACCCCA GTGAGCATCG AGCCACGGAT CAACGTGGGC TCCCGGTTCC       2220

AGGCAGAAAT CCCCTTGATG AGGGACCGTG CCCTGGCAGC TGCAGATCCC CACAAGGCTG       2280

ACTTGGTGTG GCAGCCATGG GAGGACCTAG AGAGCAGCCG GGAGAAGCAG AGGCAAGTGG       2340

AAGACCTGCT GACAGCCGCC TGCTCCAGCA TTTTCCCTGG TGCTGGCACC AACCAGGAGC       2400

TGGCCCTGCA CTGTCTGCAC GAATCCGAGA GAGACATCCT GGAAACGCTG AATAAGCTGC       2460

TGCTGAAGAA GCCCCTGCGG CCCCACAACC ATCCGCTGGC AACTTATCAC TACACAGGCT       2520

CTGACCAGTG GAAGATGGCC GAGAGGAAGC TGTTCAACAA AGGCATTGCC ATCTACAAGA       2580

AGGATTTCTT CCTGGTGCAG AAGCTGATCC AGACCAAGAC CGTGGCCCAG TGCGTGGAGT       2640

TCTACTACAC CTACAAGAAG CAGGTGAAAA TCGGCCGCAA TGGGACTCTA ACCTTTGGGG       2700

ATGTGGATAC GAGCGATGAG AAGTCGGCCC AGGAAGAGGT TGAAGTGGAT ATTAAGACTT       2760

CCCAAAAGTT CCCAAGGGTG CCTCTTCCCA GAAGAGAGTC CCCAAGTGAA GAGAGGCTGG       2820

AGCCCAAGAG GGAGGTGAAG GAGCCCAGGA AGGAGGGGGA GGAGGAGGTG CCAGAGATCC       2880

AAGAGAAGGA GGAGCAGGAA GAGGGGCGAG AGCGCAGCAG GCGGGCAGCG GCAGTCAAAG       2940

CCACGCAGAC ACTACAGGCC AATGAGTCGG CCAGTGACAT CCTCATCCTC CGGAGCCACG       3000

AGTCCAACGC CCCTGGGTCT GCCGGTGGCC AGGCCTCGGA GAAGCAAGG GAAGGGACAG       3060

GGAAGTCACG AAGGGCACTA CCTTTTTCAG AAAAAAAAAA AAAAAAACAA AAAGCTT         3117
```

(2) INFORMATION FOR SEQ ID NO:7:

(i) SEQUENCE CHARACTERISTICS:
        (A) LENGTH: 3306 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:7:

```
GAATTCGGCA CGAGGTCAGT TTCCTGTGGA ACACAGAGGC TGCCTGTCCC ATTCAGACAA        60

CGACGGATAC AGACCAGGCT TGCTCTATAA GGGATCCCAA CAGTGGATTT GTGTTTAATC       120

TTAATCCGCT AAACAGTTCG CAAGGATATA ACGTCTCTGG CATTGGGAAG ATTTTTATGT       180

TTAATGTCTG CGGCACAATG CCTGTCTGTG GGACCATCCT GGGAAAACCT GCTTCTGGCT       240

GTGAGGCAGA AACCCAAACT GAAGAGCTCA AGAATTGGAA GCCAGCAAGG CCAGTCGGAA       300

TTGAGAAAAG CCTCCAGCTG TCCACAGAGG GCTTCATCAC TCTGACCTAC AAAGGGCCTC       360

TCTCTGCCAA AGGTACCGCT GATGCTTTTA TCGTCCGCTT TGTTTGCAAT GATGATGTTT       420

ACTCAGGGCC CCTCAAATTC CTGCATCAAG ATATCGACTC TGGGCAAGGG ATCCGAAACA       480

CTTACTTTGA GTTTGAAACC GCGTTGGCCT GTGTTCCTTC TCCAGTGGAC TGCCAAGTCA       540

CCGACCTGGC TGGAAATGAG TACGACCTGA CTGGCCTAAG CACAGTCAGG AAACCTTGGA       600
```

```
CGGCTGTTGA CACCTCTGTC GATGGGAGAA AGAGGACTTT CTATTTGAGC GTTTGCAATC      660
CTCTCCCTTA CATTCCTGGA TGCCAGGGCA GCGCAGTGGG GTCTTGCTTA GTGTCAGAAG      720
GCAATAGCTG GAATCTGGGT GTGGTGCAGA TGAGTCCCCA AGCCGCGGCG AATGGATCTT      780
TGAGCATCAT GTATGTCAAC GGTGACAAGT GTGGGAACCA GCGCTTCTCC ACCAGGATCA      840
CGTTTGAGTG TGCTCAGATA TCGGGCTCAC CAGCATTTCA GCTTCAGGAT GGTTGTGAGT      900
ACGTGTTTAT CTGGAGAACT GTGGAAGCCT GTCCCGTTGT CAGAGTGGAA GGGGACAACT      960
GTGAGGTGAA AGACCCAAGG CATGGCAACT TGTATGACCT GAAGCCCCTG GGCCTCAACG     1020
ACACCATCGT GAGCGCTGGC GAATACACTT ATTACTTCCG GGTCTGTGGG AAGCTTTCCT     1080
CAGACGTCTG CCCCACAAGT GACAAGTCCA AGGTGGTCTC CTCATGTCAG GAAAAGCGGG     1140
AACCGCAGGG ATTTCACAAA GTGGCAGGTC TCCTGACTCA GAAGCTAACT TATGAAAATG     1200
GCTTGTTAAA AATGAACTTC ACGGGGGGG ACACTTGCCA TAAGGTTTAT CAGCGCTCCA      1260
CAGCCATCTT CTTCTACTGT GACCGCGGCA CCCAGCGGCC AGTATTTCTA AAGGAGACTT     1320
CAGATTGTTC CTACTTGTTT GAGTGGCGAA CGCAGTATGC CTGCCCACCT TTCGATCTGA     1380
CTGAATGTTC ATTCAAAGAT GGGGCTGGCA ACTCCTTCGA CCTCTCGTCC CTGTCAAGGT     1440
ACAGTGACAA CTGGGAAGCC ATCACTGGGA CGGGGGACCC GGAGCACTAC CTCATCAATG     1500
TCTGCAAGTC TCTGGCCCCG CAGGCTGCA CTGAGCCGTG CCCTCCAGAA GCAGCCGCGT      1560
GTCTGCTGGG TGGCTCCAAG CCCGTGAACC TCGGCAGGGT AAGGGACGGA CCTCAGTGGA     1620
GAGATGGCAT AATTGTCCTG AAATACGTTG ATGGCGACTT ATGTCAGAT GGGATTCGGA      1680
AAAAGTCAAC CACCATCCGA TTCACCTGCA GCGAGAGCCA AGTGAACTCC AGGCCCATGT     1740
TCATCAGCGC CGTGGAGGAC TGTGAGTACA CCTTTGCCTG GCCCACAGCC ACAGCCTGTC     1800
CCATGAAGAG CAACGAGCAT GATGACTGCC AGGTCACCAA CCCAAGCACA GGACACCTGT     1860
TTGATCTGAG CTCCTTAAGT GGCAGGGCGG GATTCACAGC TGCTTACAGC GAGAAGGGGT     1920
TGGTTTACAT GAGCATCTGT GGGGAGAATG AAAACTGCCC TCCTGGCGTG GGGGCCTGCT     1980
TTGGACAGAC CAGGATTAGC GTGGGCAAGG CCAACAAGAG GCTGAGATAC GTGGACCAGG     2040
TCCTGCAGCT GGTGTACAAG GATGGGTCCC CTTGTCCCTC CAAATCCGGC CTGAGCTATA     2100
AGAGTGTGAT CAGTTTCGTG TGCAGGCCTG AGGCCGGGCC AACCAATAGG CCCATGCTCA     2160
TCTCCCTGGA CAAGCAGACA TGCACTCTCT TCTTCTCCTG GCACACGCCG CTGGCCTGCG     2220
AGCAAGCGAC CGAATGTTCC GTGAGGAATG GAAGCTCTAT TGTTGACTTG TCTCCCCTTA     2280
TTCATCGCAC TGGTGGTTAT GAGGCTTATG ATGAGAGTGA GGATGATGCC TCCGATACCA     2340
ACCCTGATTT CTACATCAAT ATTTGTCAGC CACTAAATCC CATGCACGGA GTGCCCTGTC     2400
CTGCCGGAGC CGCTGTGTGC AAAGTTCCTA TTGATGGTCC CCCCATAGAT ATCGGCCGGG     2460
TAGCAGGACC ACCAATACTC AATCCAATAG CAAATGAGAT TTACTTGAAT TTTGAAAGCA     2520
GTACTCCTTG CCAGGAATTC AGTTGTAAAT AAAATTGAAC CTGCTCAACA GCTGAGGGAG     2580
ACTAGAAATG ATGGGTCCAT ATCCTGGTGC ATTGTCATAC AATTCAAACA ATGGTGCAGC     2640
TACCAGCTTG TAATTTTTAG GGACTGCAAA CAAGGCTTTT TCTTGAAGCT GAACCAGAAA     2700
CAACTTCTTA TGTTCCTTAG GCTTTGTAAT ATGTGCAGGA ATATATGGAT ACTGAGGAGG     2760
TTCAAAATTT GGTCTCCACC AGTTACCAAT GCAATCGTCA ATGACCCAGT CTTGCAAAAC     2820
TCCATCCTGA CGACCCAGTA TCTCTGTCAT TAAGCGTTTT AGTCCTTCAA CTTCATCTTC     2880
TCCTGGGTTA AGTTCACCAC CAGGTAGTTT GAAGAAAGTT GTTCCCAGCT GCAGCAGTAA     2940
CACATGGGGT AGCCGGTGCT CATGTACAAT CAGAACCCCT TCTACAGTCC TCCTCATTCC     3000
```

| | | | | |
|---|---|---|---|---|
| AATTTTATCA | AATTCTTCCC | TCATGCGCTG | AAATCTGGCT | GCAACAGAGC | TGTCCTTCTC | 3060 |
| GTAGAGGGGC | TCTTTTGTAC | CAAAAGTATA | ATTGGTAAGA | GGGTACAGGT | TGATGGTGCG | 3120 |
| CTCCAGGGTG | AGGGGCTTCG | TCTGCTGGAT | GTACTTGTTG | CCGAACTGAG | TGACCCCCCG | 3180 |
| GGGCCAGCCG | GTCTGCGAGC | GATTGGGCGG | TACCACAGAC | ATGCTGGCGA | GCTCCGGCGC | 3240 |
| TGACGGCGAG | CAGAAAGTGG | CAGGCAGGGT | AGACTTTCCC | CGTGCGGGAA | GCCTCGTGCC | 3300 |
| GAATTC | | | | | | 3306 |

(2) INFORMATION FOR SEQ ID NO:8:

(i) SEQUENCE CHARACTERISTICS:
        (A) LENGTH: 4218 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:8:

| | | | | | | |
|---|---|---|---|---|---|---|
| GAATTCGGCA | CGAGAATGGA | TCAACCTCAA | CAACACGTTA | AAGCTAGACG | AAAGAAGTAA | 60 |
| TACACAGTGT | ATGAGTCTCA | CATGAAATAC | CCGGATGTAA | ATCCAAAGAA | ACAGGAAGCA | 120 |
| GATTGGTGGT | TGCCAGGGAC | AAGGGCGGTG | GGAGGAGAAA | ATGGAGAGTA | ACGGGACTTT | 180 |
| ACTTTTGGAG | TGATGAGAAT | GTTTTGGAGC | TAGATAGAAG | TGGTGGTTGT | ACACCATTGT | 240 |
| GGATGTACTA | CCACTTAATT | GTTCACTTAA | AAAGTTAATT | TATGTGAATT | GCATCTTAAT | 300 |
| TAAAAACAAG | GATAACATTC | CAACTCCTGG | ACATTATCCT | TCCTTTCCAT | TTGATGTCAG | 360 |
| GCCCGTGTTA | GAATTCTCAT | CCGGTTTGGT | CACTGCACTT | AAGATGTGGA | GAAATTAGGA | 420 |
| CGCACAGTTA | AGAGGAAGGA | TAACACTGAT | TAAGGTAGTG | CTTTTCTAGG | TTTCCCCTAA | 480 |
| ACAATTTAAC | AGATGGATAG | TGGCACCACT | TACGAGATGG | AAAAACCAGC | GGAAGGAAGA | 540 |
| TTTGGGGGAG | AAGTTAAGTT | TGTCTTGGGC | CTGTGTTTTG | CAACCTGAGT | GTAAAAGACA | 600 |
| TATGTTAAGT | CTTCAGTGGC | GAAACACTAA | AACTAGAAAT | GGATCAGAAT | TTTATCTTTG | 660 |
| GATGTGACTT | CTCAAGGATG | GTCTTGTCAC | TTCAGTGCCT | GGTCAAATGA | CAAGATGGGC | 720 |
| AATCTTTTCC | TGAAGGTCCA | AGCACCTGAA | CGTGGCAGGG | TGACCCGATT | CCGATTTGCT | 780 |
| TAGAACAATC | CTAGTTCATG | CCTATTGTCC | CTCATGTAAT | TAATATCACT | CTCAAAATGT | 840 |
| CTCATTTTGT | GCAATAAATT | CTGCAACGTG | ATGGCGCGAC | TCTCGCGGCC | CGAGCGGCCG | 900 |
| GACCTTGTCT | TCGAGGAAGA | GGACCTCCCC | TATGAGGAGG | AAATCATGCG | GAACCAATTC | 960 |
| TCTGTCAAAT | GCTGGCTTCA | CTACATCGAG | TTCAAACAGG | GCGCCCCGAA | GCCCAGGCTC | 1020 |
| AATCAGCTAT | ACGAGCGGGC | ACTCAAGCTG | CTGCCCTGCA | GCTACAAACT | CTGGTACCGA | 1080 |
| TACCTGAAGG | CGCGTCGGGC | ACAGGTGAAG | CATCGCTGTG | TGACCGACCC | TGCCTATGAA | 1140 |
| GATGTCAACA | ACTGTCATGA | GAGGGCCTTT | GTGTTCATGC | ACAAGATGCC | TCGTCTGTGG | 1200 |
| CTAGATTACT | GCCAGTTCCT | CATGGACCAG | GGGCGCGTCA | CACACACCCG | CCGCACCTTC | 1260 |
| GACCGTGCCC | TCCGGGCACT | GCCCATCACG | CAGCACTCTC | GAATTTGGCC | CCTGTATCTG | 1320 |
| CGCTTCCTGC | GCTCACACCC | ACTGCCTGAG | ACAGCTGTGC | GAGGCTATCG | GCGCTTCCTC | 1380 |
| AAGCTGAGTC | CTGAGAGTGC | AGAGGAGTAC | ATTGAGTACC | TCAAGTCAAG | TGACCGGCTG | 1440 |
| GATGAGGCCG | CCCAGCGCCT | GGCCACCGTG | GTGAACGACG | AGCGTTTCGT | GTCTAAGGCC | 1500 |
| GGCAAGTCCA | ACTACCAGCT | GTGGCACGAG | CTGTGCGACC | TCATCTCCCA | GAATCCGGAC | 1560 |
| AAGGTACAGT | CCCTCAATGT | GGACGCCATC | ATCCGCGGGG | GCCTCACCCG | CTTCACCGAC | 1620 |

```
CAGCTGGGCA AGCTCTGGTG TTCTCTCGCC GACTACTACA TCCGCAGCGG CCATTTCGAG    1680

AAGGCTCGGG ACGTGTACGA GGAGGCCATC CGGACAGTGA TGACCGTGCG GGACTTCACA    1740

CAGGTGTTTG ACAGCTACGC CCAGTTCGAG GAGAGCATGA TCGCTGCAAA GATGGAGACC    1800

GCCTCGGAGC TGGGGCGCGA GGAGGAGGAT GATGTGGACC TGGAGCTGCG CCTGGCCCGC    1860

TTCGAGCAGC TCATCAGCCG GCGGCCCCTG CTCCTCAACA GCGTCTTGCT GCGCCAAAAC    1920

CCACACCACG TGCACGAGTG GCACAAGCGT GTCGCCCTGC ACCAGGGCCG CCCCCGGGAG    1980

ATCATCAACA CCTACACAGA GGCTGTGCAG ACGGTGGACC CCTTCAAGGC CACAGGCAAG    2040

CCCCACACTC TGTGGGTGGC GTTTGCCAAG TTTTATGAGG ACAACGGACA GCTGGACGAT    2100

GCCCGTGTCA TCCTGGAGAA GGCCACCAAG GTGAACTTCA GCAGGTGGA TGACCTGGCA    2160

AGCGTGTGGT GTCAGTGCGG AGAGCTGGAG CTCCGACACG AGAACTACGA TGAGGCCTTG    2220

CGGCTGCTGC GAAAGGCCAC GGCGCTGCCT GCCCGCCGGG CCGAGTACTT TGATGGTTCA    2280

GAGCCCGTGC AGAACCGCGT GTACAAGTCA CTGAAGGTCT GGTCCATGCT CGCCGACCTG    2340

GAGGAGAGCC TCGGCACCTT CCAGTCCACC AAGGCCGTGT ACGACCGCAT CCTGGACCTG    2400

CGTATCGCAA CACCCCAGAT CGTCATCAAC TATGCCATGT TCCTGGAGGA GCACAAGTAC    2460

TTCGAGGAGA GCTTCAAGGC GTACGAGCGC GGCATCTCGC TGTTCAAGTG GCCCAACGTG    2520

TCCGACATCT GGAGCACCTA CCTGACCAAA TTCATTGCCC GCTATGGGGG CCGCAAGCTG    2580

GAGCGGGCAC GGGACCTGTT TGAACAGGCT CTGGACGGCT GCCCCCCAAA ATATGCCAAG    2640

ACCTTGTACC TGCTGTACGC ACAGCTGGAG GAGGAGTGGG GCCTGGCCCG GCATGCCATG    2700

GCCGTGTACG AGCGTGCCAC CAGGGCCGTG GAGCCCGCCC AGCAGTATGA CATGTTCAAC    2760

ATCTACATCA AGCGGGCGGC CGAGATCTAT GGGGTCACCC ACACCCGCGG CATCTACCAG    2820

AAGGCCATTG AGGTGCTGTC GGACGAGCAC GCGCGTGAGA TGTGCCTGCG GTTTGCAGAC    2880

ATGGAGTGCA AGCTCGGGGA GATTGACCGC GCCCGGGCCA TCTACAGCTT CTGCTCCCAG    2940

ATCTGTGACC CCCGGACGAC CGGCGCGTTC TGGCAGACGT GGAAGGACTT TGAGGTCCGG    3000

CATGGCAATG AGGACACCAT CAAGGAAATG CTGCGTATCC GGCGCAGCGT GCAGGCCACG    3060

TACAACACGC AGGTCAACTT CATGGCCTCG CAGATGCTCA AGGTCTCGGG CAGTGCCACG    3120

GGCACCGTGT CTGACCTGGC CCCTGGGCAG AGTGGCATGG ACGACATGAA GCTGCTGGAA    3180

CAGCGGGCAG AGCAGCTGGC GGCTGAGGCG GAGCGTGACC AGCCCTTGCG CGCCCAGAGC    3240

AAGATCCTGT TCGTGAGGAG TGACGCCTCC CGGGAGGAGC TGGCAGAGCT GGCACAGCAG    3300

GTCAACCCCG AGGAGATCCA GCTGGGCGAG GACGAGGACG AGGACGAGAT GGACCTGGAG    3360

CCCAACGAGG TTCGGCTGGA GCAGCAGAGC GTGCCAGCCG CAGTGTTTGG GAGCCTGAAG    3420

GAAGACTGAC CCGTCCCCTC GTGCCGAATT CGGCACGAGC AAGACCAGCC CCCAGATCAT    3480

TTGCCTCAAA GGTTTTCCCT CGAAGTCACA AATGTTTCAA GGAATCTCAA ATTTTACAAA    3540

GTTTGAAGTG TGGGCATTGG TGGCCTGTGG CTGTGTCCTC TCTCTGTAGC TGTTTTCTCC    3600

CTACATCCCT GAAAGGAAGT TGAGCCTGCT CCTCCATCCG CAGACCTCCC TTTCCAGCGC    3660

CCAGGGCATG GGGTGCTGTG AGGGCAGCAT GCTAGGTGTG ACCGTGCTCC TGGCCTCCAG    3720

GCCCGTGTCC CTCTGTCCTC TAGCCCACTA AGGCCCTGGC CCATTTGTGC TAAACAGGCA    3780

GTCGGACCTA GAAAGAGCAG ACAATCTCTC TGGGTCACCA GTCTGGCTAG GAGCTGGTCT    3840

CCTGACTGGG ATCCAGGCCT TCTCCCCTGC CCATGTGAAT TCCCAGGGGC AGAGCCTGAA    3900

ATGTTGAACA CAGCACTGGC CAAAGAGATG TCACCGTGGG AACCGAGGCT CTCTTCTCCT    3960
```

```
CCTGCCTGCT TTCGTGGGTT CAGAGTAGCT GAGGCTTGTC TGAGAGGAGT TGGAGTGCTG    4020

GTTTTCACCC TGGTTGGTGT GCTTTGCTTT GAGGGCACTT AGAAAGCCCA GCCCAGCCCT    4080

TGCTCCTGCC CTGCACACAG CGGAGCGACT TTTCTAGGTA TGCTCTTGAT TTCTGCAGAA    4140

GCAGCAGGTG GCATGGAGCC AAGAGGAAGT GTGACTGAAA CTGTCCACTC ATAGCCCGGC    4200

TGCCGTATTG AGAGGGCT                                                  4218

(2) INFORMATION FOR SEQ ID NO:9:

(i) SEQUENCE CHARACTERISTICS:
        (A) LENGTH: 1187 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:9:

GAGCTCGCGC GCCTGCAGGT CGACACTAGT GGATCCAAAG AATTCGGCAC GAGGGAAACT      60

CAACGGTGTA CGAGTGGAGG ACAGGGACAG AGCCCTCTGT GGTGGAACGA CCCCACCTCG     120

AGGAGCTTCC TGAGCAGGTG GCAGAAGATG CGATTGACTG GGGCGACTTT GGGGTAGAGG     180

CAGTGTCTGA GGGGACTGAC TCTGGCATCT CTGCCGAGGC TGCTGGAATC GACTGGGGCA     240

TCTTCCCGGA ATCAGATTCA AAGGATCCTG GAGGTGATGG GATAGACTGG GGAGACGATG     300

CTGTTGCTTT GCAGATCACA GTGCTGGAAG CAGGAACCCA GGCTCCAGAA GGTGTTGCCA     360

GGGGCCCAGA TGCCCTGACA CTGCTTGAAT ACACTGAGAC CCGGAATCAG TTCCTTGATG     420

AGCTCATGGA GCTTGAGATC TTCTTAGCCC AGAGAGCAGT GGAGTTGAGT GAGGAGGCAG     480

ATGTCCTGTC TGTGAGCCAG TTCCAGCTGG CTCCAGCCAT CCTGCAGGGC CAGACCAAAG     540

AGAAGATGGT TACCATGGTG TCAGTGCTGG AGGATCTGAT TGGCAAGCTT ACCAGTCTTC     600

AGCTGCAACA CCTGTTTATG ATCCTGGCCT CACCAAGGTA TGTGGACCGA GTGACTGAAT     660

TCCTCCAGCA AAAGCTGAAG CAGTCCCAGC TGCTGGCTTT GAAGAAAGAG CTGATGGTGC     720

AGAAGCAGCA GGAGGCACTT GAGGAGCAGG CGGCTCTGGA GCCTAAGCTG GACCTGCTAC     780

TGGAGAAGAC CAAGGAGCTG CAGAAGCTGA TTGAAGCTGA CATCTCCAAG AGGTACAGCG     840

GGCGCCCTGT GAACCTGATG GGAACCTCTC TGTGACACCC TCCGTGTTCT TGCCTGCCCA     900

TCTTCTCCGC TTTTGGGATG AAGATGATAG CCAGGGCTGT TGTTTTGGGG CCCTTCAAGG     960

CAAAAGACCA GGCTGACTGG AAGATGGAAA GCCACAGGAA GGAAGCGGCA CCTGATGGTG    1020

ATCTTGGCAC TCTCCATGTT CTCTACAAGA AGCTGTGGTG ATTGGCCCTG TGGTCTATCA    1080

GGCGAAAACC ACAGATTCTC CTTCTAGTTA GTATAGCGCA AAAAGCTTCT CGAGAGTACT    1140

TCTAGAGCGG CCGCGGGCCC ATCGATTTTC CACCCGGGTG GGGTACC                  1187

(2) INFORMATION FOR SEQ ID NO:10:

(i) SEQUENCE CHARACTERISTICS:
        (A) LENGTH: 3306 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:10:

CCCTCACTAA AGGGAACAAA AGCTGGAGCT CGCGCGCCTG CAGGTCGACA CTAGTGGATC      60

GAAAGTTCGT TACGCCAAGC TCGAAATTAA CTCTGGGCTG ACCCATAAAC ATTTGTCTGA     120
```

-continued

```
TCTAGGATAT AGTTGCGTTT CTTGCGGGCA GCAATCTGGA TGAGGCGGTT GAGGCACTGG    180
GTGGCCTGCT GGATCAGGAC ATCCCAGCGG CCAGCATAGT TCCGCTGCCG GCGTAGGCCC    240
ATCACCCGCA TCTTATCCAT GATGGCATTG GTACCCAGGA TGTTGTACTT CTTGGAAGGG    300
TTGGAGGCTG CATGTTTGAT GGCCCATGTG GTCTTGCCAG CAGCAGGCAG GCCCACCATC    360
ATCAGAATCT CACATTCTGC CTTGCTCTTT GGTCCAACGG TGCCCCGGAT ACGCTCACTA    420
AGGGGAAGGT GCTGGATGAA GGTAAACCCC GGGAGGACAG AACAGTAGGG CTCTGCTCTC    480
TGTCCGAAGT TGAACTCCAC TGCGCAATTC TTCACCAGGA CATGAGGATA GAGGGCCTGA    540
CCCCCCAAGG CTTCCTTCTG GATTCGGAAA GCAATGCCCA TCCACTTTCC ATTCTTGGTA    600
AAAGACAGTT CCACGTCATT TCCACATTCA AAATCCGCAA AGCAGCCAAT CACCGGAGAG    660
CTCTGCGGTG CTAGGAGAGC GGCTGGGCCC GCAGACTGGG GGGAAAGCTC CGCAGCCGCA    720
GTGGGCCCCA GGATCAGGCC CCGCGTGGCC TGGAGAAGCC CAGTCTGGGC TGGAGCGGGA    780
GCTGGACAGT GTGGCCTTGC GTTCGCCCCC GGGAGCGCTG CGAGTGTCGC GGCCTCGGGT    840
GGATTTGCTG AGCACCAATA CCTCACGGTT GCCAACCTGG GGTTTTAGCT CCCTTGGTTT    900
TAATCCCCTA GGGGCGGGTG GGGGCACGGG AGGAAGGATG GGCCAGCTGG GTGCAATCCT    960
GCTGTAAGCC AGCCATTCCT TGATTTCTTA GAATTAACTA AACGGTCGCG CCGGAGGCCG   1020
CGGGGGCCGG AGCGGAGCAG CCGCGGCTGA GGTTCCCGAG TCGGCCGCTC GGGGCTGCGC   1080
TCCGCCGCCG GGACCCCGGC CTCTGGCCGC GCCGGCTCCG GCCTCCGGGG GGCCGGGGC    1140
CGCCGGGACA TGGTGCCAGT CGCACCCCTT CCCCGCCGCC GCTGAGCTCG CCGGCCGCGC   1200
CCGGGCTGGG ACGTCCGAGC GGGAAGATGT TTTCCGCCCT GAAGAAGCTG GTGGGGTCGG   1260
ACCAGGCCCC GGGCCGGGAC AAGAACATCC CCGCCGGGCT GCAGTCCATG AACCAGGCGT   1320
TGCAGAGGCG CTTCGCCAAG GGGGTGCAGT ACAACATGAA GATAGTGATC CGGGGAGACA   1380
GGAACACGGG CAAGACAGCG CTGTGGCACC GCCTGCAGGG CCGGCCGTTC GTGGAGGAGT   1440
ACATCCCCAC ACAGGAGATC CAGGTCACCA GCATCCACTG GAGCTACAAG ACCACGGATG   1500
ACATCGTGAA GGTTGAAGTC TGGGATGTAG TAGACAAAGG AAAATGCAAA AAGCGAGGCG   1560
ACGGCTTAAA GATGGAGAAC GACCCCCAGG AGNCGGAGTC TGAAATGGCC CTGGATGCTG   1620
AGTTCCTGGA CGTGTACAAG AACTGCAACG GGGTGGTCAT GATGTTCGAC ATTACCAAGC   1680
AGTGGACCTT CAATTACATT CTCCGGGAGC TTCCAAAAGT GCCCACCCAC GTGCCAGTGT   1740
GCGTGCTGGG GAACTACCGG GACATGGGCG AGCACCGAGT CATCCTGCCG GACGACGTGC   1800
GTGACTTCAT CGACAACCTG GACAGACCTC CAGGTTCCTC CTACTTCCGC TATGCTGAGT   1860
CTTCCATGAA GAACAGCTTC GGCCTAAAGT ACCTTCATAA GTTCTTCAAT ATCCCATTTT   1920
TGCAGCTTCA GAGGGAGACG CTGTTGCGGC AGCTGGAGAC GAACCAGCTG GACATGGACG   1980
CCACGCTGGA GGAGCTGTCG GTGCAGCAGG AGACGGAGGA CCAGAACTAC GGCATCTTCC   2040
TGGAGATGAT GGAGGCTCGC AGCCGTGGCC ATGCGTCCCC ACTGGCGGCC AACGGGCAGA   2100
GCCCATCCCC GGGCTCCCAG TCACCAGTCC TGCCTGCACC CGCTGTGTCC ACGGGGAGCT   2160
CCAGCCCCGG CACACCCCAG CCCGCCCCAC AGCTGCCCCT CAATGCTGCC CCACCATCCT   2220
CTGTGCCCCC TGTACCACCC TCAGAGGCCC TGCCCCACC TGCGTGCCCC TCAGCCCCCG    2280
CCCCACGGCG CAGCATCATC TCTAGGCTGT TTGGGACGTC ACCTGCCACC GAGGCAGCCC   2340
CTCCACCTCC AGAGCCAGTC CCGGCCGCAC AGGGCCCAGC AACGGTCCAG AGTGTGGAGG   2400
ACTTTGTTCC TGACGACCGC CTGGACCGCA GCTTCCTGGA AGACACAACC CCCGCCAGGG   2460
```

-continued

| | | | | |
|---|---|---|---|---|
| ACGAGAAGAA | GGTGGGGGCC | AAGGCTGCCC | AGCAGGACAG | TGACAGTGAT GGGGAGGCCC | 2520 |
| TGGGCGGCAA | CCCGATGGTG | GCAGGGTTCC | AGGACGATGT | GGACCTCGAA GACCAGCCAC | 2580 |
| GTGGGAGTCC | CCCGCTGCCT | GCAGGCCCCG | TCCCCAGTCA | AGACATCACT CTTTCGAGTG | 2640 |
| AGGAGGAAGC | AGAAGTGGCA | GCTCCCACAA | AAGGCCCTGC | CCCAGCTCCC CAGCAGTGCT | 2700 |
| CAGAGCCAGA | GACCAAGTGG | TCCTCCATAC | CAGCTTCGAA | GCCACGGAGG GGACAGCTC | 2760 |
| CCACGAGGAC | CGCAGCACCC | CCCTGGCCAG | GCGGTGTCTC | TGTTCGCACA GGTCCGGAGA | 2820 |
| AGCGCAGCAG | CACCAGGCCC | CCTGCTGAGA | TGGAGCCGGG | GAAGGGTGAG CAGGCCTCCT | 2880 |
| CGTCGGAGAG | TGACCCCGAG | GGACCCATTG | CTGCACAAAT | GCTGTCCTTC GTCATGGATG | 2940 |
| ACCCCGACTT | TGAGAGCGAG | GGATCAGACA | CACAGCGCAG | GCGGATGAC TTTCCCGTGC | 3000 |
| GAGATGACCC | CTCCGATGTG | ACTGACGAGG | ATGAGGGCCC | TGCCGAGCCG CCCCCACCCC | 3060 |
| CCAAGCTCCC | TCTCCCCGCC | TTCAGACTGA | AGAATGACTC | GGACCTCTTC GGGCTGGGGC | 3120 |
| TGGAGGAGGC | CGGACCCAAG | GAGAGCAGTG | AGGAAGGTAA | GGAGGGCAAA ACCCCCTCTA | 3180 |
| AGGAGAAGAA | AAAAAAAACA | AAAAGCTTCT | CGAGAGTACT | TCTAGAGCGG CCGCGGGCCC | 3240 |
| ATCGATTTTC | CACCCGGGTG | GGGTACCAGG | TAAGTGTACC | CAATTCGCCC TATAGTGAGT | 3300 |
| CGTATT | | | | | 3306 |

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:11:

TGCGGGGCCA GAGTGGGCTG                                 20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:12:

GCAGTCCTGG CCTGCGGATG                                 20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:13:

GTCGACAGGA GAATTGGTTC                                 20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:14:

```
GCCTGGGTTC GGTGCGGGAC                                                    20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:15:

TGGTCGGGTG TTTGTGAGTG                                                    20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:16:

CCTCTTCCGT CTCCTCAGTG                                                    20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:17:

GGATTGCTAG TCTCACAGAC                                                    20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:18:

TTAAGGGTGG CTGAAGGGAC                                                    20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:19:

ACCTTCCCTC CCTGTCACAG                                                    20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:20:
```

```
TGGTCGGGTG TTTGTGAGTG                                                    20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:21:

ACACCATTCC AGAAATTCAG                                                    20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:22:

AAACTGCAGG TGGCTGAGTC                                                    20

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:23:

GTCCTAATGT TTTCAGGGAG                                                    20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:24:

AAAACCTATG GTTACAATTC                                                    20

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:25:

TCCTAGACAT GGTTCAAGTG                                                    20

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:26:

GATATAATTA GTTCTCCATC                                                    20
```

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:27:

ATGCCTGTTC CAGGCTGCAC                                               20

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:28:

GGACGGCGAC CTCCACCCAC                                               20

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:29:

GGGCTCCTCC GACGCCTGAG                                               20

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:30:

AGTCTAGCCC TGGCCTTGAC                                               20

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:31:

GTCACTGGGG ACTCCGGCAG                                               20

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:32:

CAGCTTTCCC TGGGCACATG                                               20

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:33:

CACAGCTGTC TCAAGCCCAG                                      20

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:34:

ACTGTTCCCC CTACATGATG                                      20

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:35:

ATCATATCCT CTTGCTGGTC                                      20

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:36:

GTTCCCAGAG CTTGTCTGTG                                      20

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:37:

GTTTGGCAGA CTCATAGTTG                                      20

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:38:

TAGCAGGGAG CCATGACCTG                                      20

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:39:

CTTGGCGCCA GAAGCGAGAG                                            20

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:40:

CCTCTCTCTC TCTCTCTCTC                                            20

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:41:

TCCCCGCTGA TTCCGCCAAG                                            20

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:42:

CTTTTTGAAT TCGGCACGAG                                            20

(2) INFORMATION FOR SEQ ID NO:43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:43:

CCCCTGGTCC GCACCAGTTC                                            20

(2) INFORMATION FOR SEQ ID NO:44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:44:

GAGAAGGGTC GGGGCGGCAG                                            20

(2) INFORMATION FOR SEQ ID NO:45:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:45:

AAATCACATC GCGTCAACAC                                                   20

(2) INFORMATION FOR SEQ ID NO:46:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:46:

TAAGAGAGTC ATAGTTACTC                                                   20

(2) INFORMATION FOR SEQ ID NO:47:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:47:

GCTCTAGAAG TACTCTCGAG                                                   20

(2) INFORMATION FOR SEQ ID NO:48:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:48:

ACTCTGGCCA TCAGGAGATC                                                   20

(2) INFORMATION FOR SEQ ID NO:49:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:49:

CAGGCGTTGT AGATGTTCTG                                                   20

(2) INFORMATION FOR SEQ ID NO:50:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:50:

AGTGGCAGGC AGAAGTAATG                                                   20

(2) INFORMATION FOR SEQ ID NO:51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:51:

GGTTGGAGAA CTGGATGTAG                                                         20

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:52:

CTATTCAGAT GCAACGCCAG                                                         20

(2) INFORMATION FOR SEQ ID NO:53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:53:

CCATGGCACA CAGAGCAGAC                                                         20

(2) INFORMATION FOR SEQ ID NO:54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:54:

GCTACCATGC AGAGACACAG                                                         20

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:55:

CAGGCTGACA AGAAAATCAG                                                         20

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:56:

GGCACGCATA GAGGAGAGAC                                                         20

(2) INFORMATION FOR SEQ ID NO:57:

(i) SEQUENCE CHARACTERISTICS:

(A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:57:

TGGGTGATGC CTTTGCTGAC                                              20

(2) INFORMATION FOR SEQ ID NO:58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:58:

AAAACAAGAT CAAGGTGATG                                              20

(2) INFORMATION FOR SEQ ID NO:59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:59:

TTGCCCACAT TGCTATGGTG                                              20

(2) INFORMATION FOR SEQ ID NO:60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:60:

GACCAAGATC AGAAGTAGAG                                              20

(2) INFORMATION FOR SEQ ID NO:61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:61:

CCCCTGGGCC AATGATGTTG                                              20

(2) INFORMATION FOR SEQ ID NO:62:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:62:

TCTTCCCACC ATAGCAATG                                               19

(2) INFORMATION FOR SEQ ID NO:63:

(i) SEQUENCE CHARACTERISTICS:
        (A) LENGTH: 20 base pairs

```
        (B) TYPE: nucleic acid
        (C) STRANDEDNESS: single
        (D) TOPOLOGY: linear (xi) SEQUENCE DESCRIPTION: SEQ ID NO:63:

TGGTCTTGGT GACCAATGTG                                               20

(2) INFORMATION FOR SEQ ID NO:64:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:64:

ACACCTCGGT GACCCCTGTG                                               20

(2) INFORMATION FOR SEQ ID NO:65:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:65:

TCTCCAAGTT CGGCACAGTG                                               20

(2) INFORMATION FOR SEQ ID NO:66:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:66:

ACATGGGCTG CACTCACGAC                                               20

(2) INFORMATION FOR SEQ ID NO:67:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:67:

GATCCTCTGA ACCTGCAGAG                                               20

(2) INFORMATION FOR SEQ ID NO:68:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:68:

GGAAATGAGG TGGGGCGATC                                               20

(2) INFORMATION FOR SEQ ID NO:69:

(i) SEQUENCE CHARACTERISTICS:
        (A) LENGTH: 20 base pairs
        (B) TYPE: nucleic acid
```

(C) STRANDEDNESS: single
        (D) TOPOLOGY: linear (xi) SEQUENCE DESCRIPTION: SEQ ID NO:69:

CTTTGCCTTG GACAAGGATG                                                    20

(2) INFORMATION FOR SEQ ID NO:70:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:70:

GCACCTGCCA TTGGGGGTAG                                                    20

(2) INFORMATION FOR SEQ ID NO:71:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:71:

GGTGGAAGCC ATTGACGGTG                                                    20

(2) INFORMATION FOR SEQ ID NO:72:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:72:

TGCGTCTCTC GTCGCTGCTG                                                    20

(2) INFORMATION FOR SEQ ID NO:73:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:73:

GCGGAAACTC TGTGGTGCTG                                                    20

(2) INFORMATION FOR SEQ ID NO:74:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:74:

AGGATTGCCT TCCTCTACTG                                                    20

(2) INFORMATION FOR SEQ ID NO:75:

(i) SEQUENCE CHARACTERISTICS:
        (A) LENGTH: 20 base pairs
        (B) TYPE: nucleic acid
        (C) STRANDEDNESS: single (D) TOPOLOGY: linear (xi) SEQUENCE DESCRIPTION: SEQ ID NO:75:

TGTCTGTTTC ACCAGGGCAG                                              20

(2) INFORMATION FOR SEQ ID NO:76:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:76:

CCAGTGCCTC TATGCATGTC                                              20

(2) INFORMATION FOR SEQ ID NO:77:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:77:

AGGAAGCCCA CGCACACCAC                                              20

(2) INFORMATION FOR SEQ ID NO:78:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:78:

CCCTTTGTTC CCTGATCTTC                                              20

(2) INFORMATION FOR SEQ ID NO:79:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:79:

CGCTCGGGAT CCAGGTCATC                                              20

(2) INFORMATION FOR SEQ ID NO:80:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:80:

TCGAGGTTCA GAGCGTAGTG                                              20

(2) INFORMATION FOR SEQ ID NO:81:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:81:

TCTTGGATCT CTGGCACCTC                                              20

(2) INFORMATION FOR SEQ ID NO:82:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:82:

CCATCAGAGT GAAGGAGGAG                                              20

(2) INFORMATION FOR SEQ ID NO:83:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:83:

CCATCTTCCA CTGGTCAGAG                                              20

(2) INFORMATION FOR SEQ ID NO:84:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:84:

CTCCTTCTCT TGGATCTCTG                                              20

(2) INFORMATION FOR SEQ ID NO:85:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:85:

TTACTTCAGC ACTGTTAGTC                                              20

(2) INFORMATION FOR SEQ ID NO:86:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:86:

AGGGAGGTAG CTCAAAGCTC                                              20

(2) INFORMATION FOR SEQ ID NO:87:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:87:

TGGGTCCACA GTTCGCACAG                                              20

(2) INFORMATION FOR SEQ ID NO:88:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:88:

CAACTCTGTG ATGGCTCCAG                                              20

(2) INFORMATION FOR SEQ ID NO:89:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:89:

AGCAGGGTTC TGTTCAAGAC                                              20

(2) INFORMATION FOR SEQ ID NO:90:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:90:

CCATTGGGTG CTAGTCTCTC                                              20

(2) INFORMATION FOR SEQ ID NO:91:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:91:

CAGCCATGCT GTCCCAGCAG                                              20

(2) INFORMATION FOR SEQ ID NO:92:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:92:

CTGGACCTGA GGTAGCGCTG                                              20

(2) INFORMATION FOR SEQ ID NO:93:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:93:

-continued

ATAACCACCC TGAGGCACTG                                       20

(2) INFORMATION FOR SEQ ID NO:94:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:94:

CCTGCAGGTC GACACTAGTG                                       20

(2) INFORMATION FOR SEQ ID NO:95:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:95:

AATTGGAATG AGGAGGACTG                                       20

(2) INFORMATION FOR SEQ ID NO:96:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:96:

GCTCTAGAAG TACTCTCGAG                                       20

(2) INFORMATION FOR SEQ ID NO:97:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:97:

ATTGTATGAC AATGCACCAG                                       20

(2) INFORMATION FOR SEQ ID NO:98:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:98:

TCCACAGAGG GCTTCATCAC                                       20

(2) INFORMATION FOR SEQ ID NO:99:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:99:

| | |
|---|---|
| CCTGACTGGC CTAAGCACAG | 20 |

(2) INFORMATION FOR SEQ ID NO:100:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:100:

| | |
|---|---|
| AAGCCTCATA ACCACCAGTG | 20 |

(2) INFORMATION FOR SEQ ID NO:101:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:101:

| | |
|---|---|
| TGTCAACGGT GACAAGTGTG | 20 |

(2) INFORMATION FOR SEQ ID NO:102:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:102:

| | |
|---|---|
| TTGTACACCA GCTGCAGGTC | 20 |

(2) INFORMATION FOR SEQ ID NO:103:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:103:

| | |
|---|---|
| GGGTGTGGTG CAGATGAGTC | 20 |

(2) INFORMATION FOR SEQ ID NO:104:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:104:

| | |
|---|---|
| ATCACACTCT TATAGCTCAG | 20 |

(2) INFORMATION FOR SEQ ID NO:105:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:105:

| | |
|---|---|
| GTGGGAAGCT TTCCTCAGAC | 20 |

(2) INFORMATION FOR SEQ ID NO:106:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:106:

TGATGAACAT GGGCCTGGAG                                              20

(2) INFORMATION FOR SEQ ID NO:107:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:107:

CATTGTGGAT GTACTACCAC                                              20

(2) INFORMATION FOR SEQ ID NO:108:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:108:

TGTGTTTTGC AACCTGAGTG                                              20

(2) INFORMATION FOR SEQ ID NO:109:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:109:

ATAGTGGCAC CACTTACGAG                                              20

(2) INFORMATION FOR SEQ ID NO:110:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:110:

AATTCTGCAA CGTGATGGCG                                              20

(2) INFORMATION FOR SEQ ID NO:111:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:111:

CACAAGATGC CTCGTCTGTG                                              20

(2) INFORMATION FOR SEQ ID NO:112:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:112:

AATCCGGACA AGGTACAGTC                                           20

(2) INFORMATION FOR SEQ ID NO:113:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:113:

GCACGAGTGG CACAAGCGTG                                           20

(2) INFORMATION FOR SEQ ID NO:114:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:114:

GCAAGCGTGT GGTGTCAGTG                                           20

(2) INFORMATION FOR SEQ ID NO:115:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:115:

TGTTTGAACA GGCTCTGGAC                                           20

(2) INFORMATION FOR SEQ ID NO:116:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:116:

CGGCATGGCA ATGAGGACAC                                           20

(2) INFORMATION FOR SEQ ID NO:117:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:117:

AGGACGAGAT GGACCTCCAG                                           20

-continued (2) INFORMATION FOR SEQ ID NO:118:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:118:

CCCTCTGTCC TCTAGCCCAC                                                   20

(2) INFORMATION FOR SEQ ID NO:119:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:119:

TCTTGAGGGG ACTGACTCTG                                                   20

(2) INFORMATION FOR SEQ ID NO:120:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:120:

TGAGTGAGGA GGCAGATGTC                                                   20

(2) INFORMATION FOR SEQ ID NO:121:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:121:

TGGCTTTGAA GAAAGAGCTG                                                   20

(2) INFORMATION FOR SEQ ID NO:122:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:122:

GCAAAAGACC AGGCTGACTG                                                   20

(2) INFORMATION FOR SEQ ID NO:123:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:123:

TGCAGCTCCT TGGTCTTCTC                                                   20

(2) INFORMATION FOR SEQ ID NO:124:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:124:

GATTCACAGT CCCAAGGCTC                                              20

(2) INFORMATION FOR SEQ ID NO:125:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:125:

ATCTGGATGA GGCGGTTGAG                                              20

(2) INFORMATION FOR SEQ ID NO:126:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:126:

GGTCACTCTC CGACGAGGAG                                              20

(2) INFORMATION FOR SEQ ID NO:127:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:127:

GGATCCAAAG TTCGTCTCTG                                              20

(2) INFORMATION FOR SEQ ID NO:128:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:128:

CGCTGTGTGT CTGATCCCTC                                              20

(2) INFORMATION FOR SEQ ID NO:129:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:129:

ATGAAGGTAA ACCCCGGGAG                                              20

(2) INFORMATION FOR SEQ ID NO:130:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:130:

TGGTCTCTGG CTCTGAGCAC                                               20

(2) INFORMATION FOR SEQ ID NO:131:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:131:

GCCTGGAGAA GCCCAGTCTG                                               20

(2) INFORMATION FOR SEQ ID NO:132:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:132:

CACACTCTGG ACCGTTGCTG                                               20

(2) INFORMATION FOR SEQ ID NO:133:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:133:

AAAGCTCCGC AGCCGCAGTG                                               20

(2) INFORMATION FOR SEQ ID NO:134:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:134:

TCTTCCAGGA AGCTGCGGTC                                               20

(2) INFORMATION FOR SEQ ID NO:135:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:135:

GATGGTGGGG CAGCATTGAG                                               20

(2) INFORMATION FOR SEQ ID NO:136:

(i) SEQUENCE CHARACTERISTICS:

```
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:136:

GTCACCAGTG GTGCCTGCAG                                            20

(2) INFORMATION FOR SEQ ID NO:137:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:137:

ACCTCACGGT TGCCAACCTG                                            20

(2) INFORMATION FOR SEQ ID NO:138:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:138:

CGCAACAGCG TCTCCCTCTG                                            20

(2) INFORMATION FOR SEQ ID NO:139:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:139:

AGTACCTTCA TAAGTTCTTC                                            20

(2) INFORMATION FOR SEQ ID NO:140:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:140:

TCCCAGACTT CAACCTTCAC                                            20

(2) INFORMATION FOR SEQ ID NO:141:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:141:

AAACATCTTC CCGGTCGGAC                                            20

(2) INFORMATION FOR SEQ ID NO:142:

(i) SEQUENCE CHARACTERISTICS:
        (A) LENGTH: 20 base pairs
```

```
        (B) TYPE: nucleic acid
        (C) STRANDEDNESS: single
        (D) TOPOLOGY: linear (xi) SEQUENCE DESCRIPTION: SEQ ID NO:142:

GCTGAGCACC TTTACCTCAC                                                   20

(2) INFORMATION FOR SEQ ID NO:143:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:143:

GACGTCCGTC CGGGAAGATG                                                   20

(2) INFORMATION FOR SEQ ID NO:144:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:144:

ACACAGGAGA TGCAGGTCAC                                                   20

(2) INFORMATION FOR SEQ ID NO:145:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:145:

GAGTCTTCCA TGAAGAACAG                                                   20

(2) INFORMATION FOR SEQ ID NO:146:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:146:

GCAGTGAGGA AGGTAAGGAG                                                   20

(2) INFORMATION FOR SEQ ID NO:147:

(i) SEQUENCE CHARACTERISTICS:
        (A) LENGTH: 4047 base pairs
        (B) TYPE: nucleic acid
        (C) STRANDEDNESS: double
        (D) TOPOLOGY: linear (ii) MOLECULE TYPE: Genomic DNA (ix) FEATURE:
        (A) NAME/KEY: Coding Sequence
        (B) LOCATION: 378...1799
        (D) OTHER INFORMATION:

(xi) SEQUENCE DESCRIPTION: SEQ ID NO:147:

GGATCCAAAG GACGCCCCCG CCGACAGGAG AATTGGTTCC CGGGCCCGCG GCGATGCCCC       60
```

```
CCCGGTAGCT CGGGCCCGTG GTCGGGTGTT TGTGAGTGTT TCTATGTGGG AGAAGGAGGA        120

GGAGGAGGAA GAAGAAGCAA CGATTTGTCT TCTCGGCTGG TCTCCCCCCG GCTCTACATG        180

TTCCCCGCAC TGAGGAGACG GAAGAGGAGC CGTAGCCGCC CCCCCTCCCG GCCCGGATTA        240

TAGTCTCTCG CCACAGCGGC CTCGGCCTCC CCTTGGATTC AGACGCCGAT TCGCCCAGTG        300

TTTGGGAAAT GGGAAGTAAT GACAGCTGGC ACCTGAACTA AGTACTTTTA TAGGCAACAC        360

CATTCCAGAA ATTCAGG ATG AAT GGG GAT ATG CCC CAT GTC CCC ATT ACT          410
                    Met Asn Gly Asp Met Pro His Val Pro Ile Thr
                      1               5                      10

ACT CTT GCG GGG ATT GCT AGT CTC ACA GAC CTC CTG AAC CAG CTG CCT         458
Thr Leu Ala Gly Ile Ala Ser Leu Thr Asp Leu Leu Asn Gln Leu Pro
            15                  20                  25

CTT CCA TCT CCT TTA CCT GCT ACA ACT ACA AAG AGC CTT CTC TTT AAT         506
Leu Pro Ser Pro Leu Pro Ala Thr Thr Thr Lys Ser Leu Leu Phe Asn
        30                  35                  40

GCA CGA ATA GCA GAA GAG GTG AAC TGC CTT TTG GCT TGT AGG GAT GAC         554
Ala Arg Ile Ala Glu Glu Val Asn Cys Leu Leu Ala Cys Arg Asp Asp
    45                  50                  55

AAT TTG GTT TCA CAG CTT GTC CAT AGC CTC AAC CAG GTA TCA ACA GAT         602
Asn Leu Val Ser Gln Leu Val His Ser Leu Asn Gln Val Ser Thr Asp
60              65                  70                  75

CAC ATA GAG TTG AAA GAT AAC CTT GGC AGT GAT GAC CCA GAA GGT GAC         650
His Ile Glu Leu Lys Asp Asn Leu Gly Ser Asp Asp Pro Glu Gly Asp
            80                  85                  90

ATA CCA GTC TTG TTG CAG GCC GTC CTG GCA AGG AGT CCT AAT GTT TTC         698
Ile Pro Val Leu Leu Gln Ala Val Leu Ala Arg Ser Pro Asn Val Phe
        95                  100                 105

AGG GAG AAA AGC ATG CAG AAC AGA TAT GTA CAA AGT GGA ATG ATG ATG         746
Arg Glu Lys Ser Met Gln Asn Arg Tyr Val Gln Ser Gly Met Met Met
    110                 115                 120

TCT CAG TAT AAA CTT TCT CAG AAT TCC ATG CAC AGT AGT CCT GCA TCT         794
Ser Gln Tyr Lys Leu Ser Gln Asn Ser Met His Ser Ser Pro Ala Ser
125                 130                 135

TCC AAT TAT CAA CAA ACC ACT ATC TCA CAT AGC CCC TCC AGC CGG TTT         842
Ser Asn Tyr Gln Gln Thr Thr Ile Ser His Ser Pro Ser Ser Arg Phe
140                 145                 150                 155

GTG CCA CCA CAG ACA AGC TCT GGG AAC AGA TTT ATG CCA CAG CAA AAT         890
Val Pro Pro Gln Thr Ser Ser Gly Asn Arg Phe Met Pro Gln Gln Asn
            160                 165                 170

AGC CCA GTG CCT AGT CCA TAC GCC CCA CAA AGC CCT GCA GGA TAC ATG         938
Ser Pro Val Pro Ser Pro Tyr Ala Pro Gln Ser Pro Ala Gly Tyr Met
        175                 180                 185

CCA TAT TCC CAT CCT TCA AGT TAC ACA ACA CAT CCA CAG ATG CAA CAA         986
Pro Tyr Ser His Pro Ser Ser Tyr Thr Thr His Pro Gln Met Gln Gln
    190                 195                 200

GCA TCG GTA TCA AGT CCC ATT GTT GCA GGT GGT TTG AGA AAC ATA CAT         1034
Ala Ser Val Ser Ser Pro Ile Val Ala Gly Gly Leu Arg Asn Ile His
205                 210                 215

GAT AAT AAA GTT TCT GGT CCG TTG TCT GGC AAT TCA GCT AAT CAT CAT         1082
Asp Asn Lys Val Ser Gly Pro Leu Ser Gly Asn Ser Ala Asn His His
220                 225                 230                 235

GCT GAT AAT CCT AGA CAT GGT TCA AGT GAG GAC TAC CTA CAC ATG GTG         1130
Ala Asp Asn Pro Arg His Gly Ser Ser Glu Asp Tyr Leu His Met Val
            240                 245                 250

CAC AGG CTA AGT AGT GAC GAT GGA GAT TCT TCA ACA ATG AGG AAT GCT         1178
His Arg Leu Ser Ser Asp Asp Gly Asp Ser Ser Thr Met Arg Asn Ala
        255                 260                 265
```

| | | |
|---|---|---|
| GCA TCT TTT CCC TTG AGA TCT CCA CAG CCA GTA TGC TCC CCT GCT GGA<br>Ala Ser Phe Pro Leu Arg Ser Pro Gln Pro Val Cys Ser Pro Ala Gly<br>270                       275                        280 | | 1226 |
| AGT GAA GGA ACT CCT AAA GGC TCA AGA CCA CCT TTA ATC CTA CAA TCT<br>Ser Glu Gly Thr Pro Lys Gly Ser Arg Pro Pro Leu Ile Leu Gln Ser<br>      285                       290                       295 | | 1274 |
| CAG TCT CTA CCT TGT TCA TCA CCT CGA GAT GTT CCA CCA GAT ATC TTG<br>Gln Ser Leu Pro Cys Ser Ser Pro Arg Asp Val Pro Pro Asp Ile Leu<br>300                       305                       310              315 | | 1322 |
| CTA GAT TCT CCA GAA AGA AAA CAA AAG AAG CAG AAG AAA ATG AAA TTA<br>Leu Asp Ser Pro Glu Arg Lys Gln Lys Lys Gln Lys Lys Met Lys Leu<br>                 320                       325                   330 | | 1370 |
| GGC AAG GAT GAA AAA GAG CAG AGT GAG AAA GCG GCA ATG TAT GAT ATA<br>Gly Lys Asp Glu Lys Glu Gln Ser Glu Lys Ala Ala Met Tyr Asp Ile<br>           335                       340                      345 | | 1418 |
| ATT AGT TCT CCA TCC AAG GAC TCT ACT AAA CTT ACA TTA AGA CTT TCT<br>Ile Ser Ser Pro Ser Lys Asp Ser Thr Lys Leu Thr Leu Arg Leu Ser<br>          350                       355                    360 | | 1466 |
| CGT GTA AGG TCT TCA GAC ATG GAC CAG CAA GAG GAT ATG ATT TCT GGT<br>Arg Val Arg Ser Ser Asp Met Asp Gln Gln Glu Asp Met Ile Ser Gly<br>365                       370                       375 | | 1514 |
| GTG GAA AAT AGC AAT GTT TCA GAA AAT GAT ATT CCT TTT AAT GTG CAG<br>Val Glu Asn Ser Asn Val Ser Glu Asn Asp Ile Pro Phe Asn Val Gln<br>380                       385                       390              395 | | 1562 |
| TAC CCA GGA CAG ACT TCA AAA ACA CCC ATT ACT CCA CAA GAT ATA AAC<br>Tyr Pro Gly Gln Thr Ser Lys Thr Pro Ile Thr Pro Gln Asp Ile Asn<br>                 400                       405                   410 | | 1610 |
| CGC CCA CTA AAT GCT GCT CAA TGT TTG TCG CAG CAA GAA CAA ACA GCA<br>Arg Pro Leu Asn Ala Ala Gln Cys Leu Ser Gln Gln Glu Gln Thr Ala<br>             415                       420                   425 | | 1658 |
| TTC CTT CCA GCA AAT CAA GTG CCT GTT TTA CAA CAG AAC ACT TCA GTT<br>Phe Leu Pro Ala Asn Gln Val Pro Val Leu Gln Gln Asn Thr Ser Val<br>          430                       435                    440 | | 1706 |
| GCT GCA AAA CAA CCC CAG ACC AAT AGT CAC AAA ACC TTG GTG CAG CCT<br>Ala Ala Lys Gln Pro Gln Thr Asn Ser His Lys Thr Leu Val Gln Pro<br>445                       450                       455 | | 1754 |
| GGA ACA GGC ATA GAG GTC TCA GCA GAG CTG CCC AAG GAC AAG ACC TAAGA<br>Gly Thr Gly Ile Glu Val Ser Ala Glu Leu Pro Lys Asp Lys Thr<br>460                       465                       470 | | 1804 |
| TCCAGCAGGG AACTATGTAG TCACCCCGAG AGGCCCAGCT CTCTCCGTGA GCTCTGGGCC | | 1864 |
| TAGGGTGGGG GTGGTTGTTG GTTCTGCGCG CACTGTTCCC CCTACATGAT GGGTCCATCC | | 1924 |
| CAGTTGGCTT CTCTCACTCG CTTCCTCCTG TGGAGAAGCC TGTCCAGGTG TCACTGCCTC | | 1984 |
| CAGGAAGCTG TCTCTGATTT CTCCAGTTGA CAGTGAGAT TTGCCACACC TCACATGCAT | | 2044 |
| CGCTCTTGTC CCTGGAATTG TAACCATAGG TTTTCCTGTC TCCTGGAGGA CAAGGATGAG | | 2104 |
| GGCTTTCCAC TTGAGTCTCC CTGGTGGAGC CCAGCTCCTG ACATACCTGG TAAAAGTTCT | | 2164 |
| CAAGAGAAGA ACATGGAGGA GGAATGTGGA TAACAACCCT GGCTGCCTGT GTGTTCCAAG | | 2224 |
| CTAGGAAGAT GTAATGTCCC CACAAACGGG GTAAATGGCT TGCCTGCGTC ACAGCTGTCT | | 2284 |
| CAAGCCCAGG CCCTGGGCGC CAGCCCAAGC CCAAGGACTA GGTCCAGAGC CACACAGCGC | | 2344 |
| CAGGCCACAT CCGCCTCACC TGGGACCCTT TGTGGGGTAC AGTCTCCGGC CCCACCCAGA | | 2404 |
| CCTCCTGAAG GAGAGACCCC ATGGCAAGGA CTCAGCCACC TGCAGTTTCA TAAGCCCCCA | | 2464 |
| GTGGGTTCCT AGGCATGAAG ACCACCGGTT AGAGGCTGAA CTGGCAGGAA CCTGTCTCCA | | 2524 |
| GCCCCTTCTC ACCCCAGCCG GGCCCTGCCT CAGAGGCAGC ACCCAGGACG TGGCCATGAC | | 2584 |
| CCGTGGACTC CACTCAATCC CTCTTCTCCA GGAGCCATGC AAAGTGTCAG CCAGCCAGGC | | 2644 |

-continued

```
CCCTGGAAGG CAGTCATCAC CTCTTAAGGC ATTGTGGGTG TCGGTCCTGC AACTGCCAGG       2704

TGCAGCACAC GACCCGTGTC CGGTGTTCGA TAGCAGGGAG CCATGACCTG GCAACGATTC       2764

CACGCTCAAA GGGGCACCCG GGGGGCCCTG GGTCGGGGCG GATCAGCTTT CCCTGGGCAC       2824

ATCTGCCTCA TTCCAGATCT CCAGGGCTCA TGTCTGTGAC AGGGAGGGAA GGCTCTGCCC       2884

TGGCCTTCCG TCAGCTCTGC CAGTGCAGGC TGGGCAGCCT GGGCTTTAGA GCTGGCTTCT       2944

GCCCACACTT TCTCCGTGAA AGGAAAACAA CTATGAGTCT GCCAAACGCA TCTCAGATGC       3004

GTTTTAAAAA ATTCTGGTCC CCGCTCTCTG TCCCATCATC CGCCTCGGGG ACTTCCTCTC       3064

TCCGTGGTTC TCACCCCATA CTCTGTCACT GCCACATTTT CACCTGGGCC TGGCCTTTGT       3124

CTCCACCTGA AACTCCTGAA AATCTTGAAA TGGATTTCTA GGTCACTGGG GACTCCGGCA       3184

GCACATTCGG CTTCAGAATA AAGGGCGCCC GCGGTCCCCC AGCACCTCCC CAAGCCACAC       3244

CCCTAGCTTC CCTCCCTATC CCTGCAGCCT GAGGGTCCCT TCAGCCACCC TTAAGTCCCC       3304

ACCTGGGCTC CTGCCCCGCC CCTGGCTAGC AGCGCCTTCT CCACCGGGGC CCCCTCTGCT       3364

CACAGAGCCC CCTCACCTCC CTGGGGATGA GGGGCCAGGC CATGACCCTG AAAGTCTAGC       3424

CCTGGCCTTG ACCTCCCAGG AGCGCCCTCC CCGCCCTCTC CCGGCCCCGG CCCCGTCCTC       3484

TGCTGCTGGC CTCTGGGTCG TGCCCCGCAG ACTGAGCTGC GCTTGGGGGT CCTGGCGGCC       3544

TGGGCCGTCC CGCACCGAAC CCAGGCGGTC GGAGCCCGGC GGGAAGGCGC GAGGTCCTTC       3604

TGGGGGCTCC TCCGACGCCT GAGGGCGCTG CTTCCCCGCG GCCGCCCCGG GTTTCTGCGG       3664

AGCCGGGGCC TCCGCTCTCG GGTGACCCGG TGAGACCCCC GGGGAGGCCG CTGGGGAGGC       3724

GCGGGCTCTG CTCCCGGGTC CCAAACGCAC TGGCTGCCCC TCAGGAGGGA CGGCGACCTC       3784

CACCCACGGC GCTGGCGCCC GCACGGCCGC TCCTCCCGCT CCCGCAGCCT GGACGCCTCC       3844

CGAGGCCGCC CCGCCGGGCC CCACGCGCGG CCCCATCCGC AGGCCAGGAC TGCCTTCCCG       3904

GAGCTGGCGG CCCCCAGCCT GGAGGAGCCG GCCCCAGACG CCCTCCCAGC CCTCCCCAGC       3964

CCACTCTGGC CCCGCAGCCC CCGCCTGGTC CGAGTGCGGG TCTCTGGCCC CGGCCTTTCC       4024

CGGGGAAGGA AAGCAAAAAG CTT                                              4047
```

(2) INFORMATION FOR SEQ ID NO:148:

(i) SEQUENCE CHARACTERISTICS:
        (A) LENGTH: 474 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:148:

```
Met Asn Gly Asp Met Pro His Val Pro Ile Thr Thr Leu Ala Gly Ile
 1               5                  10                  15

Ala Ser Leu Thr Asp Leu Leu Asn Gln Leu Pro Leu Pro Ser Pro Leu
            20                  25                  30

Pro Ala Thr Thr Thr Lys Ser Leu Leu Phe Asn Ala Arg Ile Ala Glu
        35                  40                  45

Glu Val Asn Cys Leu Leu Ala Cys Arg Asp Asp Asn Leu Val Ser Gln
    50                  55                  60

Leu Val His Ser Leu Asn Gln Val Ser Thr Asp His Ile Glu Leu Lys
65                  70                  75                  80
```

-continued

```
Asp Asn Leu Gly Ser Asp Asp Pro Glu Gly Asp Ile Pro Val Leu Leu
                85                  90                  95
Gln Ala Val Leu Ala Arg Ser Pro Asn Val Phe Arg Glu Lys Ser Met
            100                 105                 110
Gln Asn Arg Tyr Val Gln Ser Gly Met Met Ser Gln Tyr Lys Leu
            115                 120                 125
Ser Gln Asn Ser Met His Ser Ser Pro Ala Ser Ser Asn Tyr Gln Gln
        130                 135                 140
Thr Thr Ile Ser His Ser Pro Ser Ser Arg Phe Val Pro Pro Gln Thr
145                 150                 155                 160
Ser Ser Gly Asn Arg Phe Met Pro Gln Gln Asn Ser Pro Val Pro Ser
                165                 170                 175
Pro Tyr Ala Pro Gln Ser Pro Ala Gly Tyr Met Pro Tyr Ser His Pro
            180                 185                 190
Ser Ser Tyr Thr Thr His Pro Gln Met Gln Gln Ala Ser Val Ser Ser
        195                 200                 205
Pro Ile Val Ala Gly Gly Leu Arg Asn Ile His Asp Asn Lys Val Ser
    210                 215                 220
Gly Pro Leu Ser Gly Asn Ser Ala Asn His His Ala Asp Asn Pro Arg
225                 230                 235                 240
His Gly Ser Ser Glu Asp Tyr Leu His Met Val His Arg Leu Ser Ser
                245                 250                 255
Asp Asp Gly Asp Ser Ser Thr Met Arg Asn Ala Ala Ser Phe Pro Leu
            260                 265                 270
Arg Ser Pro Gln Pro Val Cys Ser Pro Ala Gly Ser Glu Gly Thr Pro
        275                 280                 285
Lys Gly Ser Arg Pro Pro Leu Ile Leu Gln Ser Gln Ser Leu Pro Cys
    290                 295                 300
Ser Ser Pro Arg Asp Val Pro Pro Asp Ile Leu Leu Asp Ser Pro Glu
305                 310                 315                 320
Arg Lys Gln Lys Lys Gln Lys Met Lys Leu Gly Lys Asp Glu Lys
                325                 330                 335
Glu Gln Ser Glu Lys Ala Ala Met Tyr Asp Ile Ile Ser Ser Pro Ser
            340                 345                 350
Lys Asp Ser Thr Lys Leu Thr Leu Arg Leu Ser Arg Val Arg Ser Ser
        355                 360                 365
Asp Met Asp Gln Gln Glu Asp Met Ile Ser Gly Val Glu Asn Ser Asn
    370                 375                 380
Val Ser Glu Asn Asp Ile Pro Phe Asn Val Gln Tyr Pro Gly Gln Thr
385                 390                 395                 400
Ser Lys Thr Pro Ile Thr Pro Gln Asp Ile Asn Arg Pro Leu Asn Ala
                405                 410                 415
Ala Gln Cys Leu Ser Gln Gln Glu Gln Thr Ala Phe Leu Pro Ala Asn
            420                 425                 430
Gln Val Pro Val Leu Gln Gln Asn Thr Ser Val Ala Ala Lys Gln Pro
        435                 440                 445
Gln Thr Asn Ser His Lys Thr Leu Val Gln Pro Gly Thr Gly Ile Glu
    450                 455                 460
Val Ser Ala Glu Leu Pro Lys Asp Lys Thr
465                 470
```

(2) INFORMATION FOR SEQ ID NO:149:

(i) SEQUENCE CHARACTERISTICS:

(A) LENGTH: 2998 base pairs
        (B) TYPE: nucleic acid
        (C) STRANDEDNESS: double
        (D) TOPOLOGY: linear (ii) MOLECULE TYPE: Genomic DNA (ix) FEATURE:
        (A) NAME/KEY: Coding Sequence
        (B) LOCATION: 26...799
        (D) OTHER INFORMATION:

(xi) SEQUENCE DESCRIPTION: SEQ ID NO:149:

```
AAGCTTTTTG AATTCGGCAC GAGAT GCT ACA CAG GCT ATA TTT GAA ATA CTG          52
                           Ala Thr Gln Ala Ile Phe Glu Ile Leu
                            1               5

GAG AAA TCC TGG TTG CCC CAG AAT TGT ACA CTG GTT GAT ATG AAG ATT          100
Glu Lys Ser Trp Leu Pro Gln Asn Cys Thr Leu Val Asp Met Lys Ile
 10              15                  20                  25

GAA TTT GGT GTT GAT GTA ACC ACC AAA GAA ATT GTT CTT GCT GAT GTT          148
Glu Phe Gly Val Asp Val Thr Thr Lys Glu Ile Val Leu Ala Asp Val
                 30                  35                  40

ATT GAC AAT GAT TCC TGG AGA CTC TGG CCA TCA GGA GAT CGA AGC CAA          196
Ile Asp Asn Asp Ser Trp Arg Leu Trp Pro Ser Gly Asp Arg Ser Gln
             45                  50                  55

CAG AAA GAC AAA CAG TCT TAT CGG GAC CTC AAA GAA GTA ACT CCT GAA          244
Gln Lys Asp Lys Gln Ser Tyr Arg Asp Leu Lys Glu Val Thr Pro Glu
         60                  65                  70

GGG CTC CAA ATG GTA AAG AAA AAC TTT GAG TGG GTT GCA GAG AGA GTA          292
Gly Leu Gln Met Val Lys Lys Asn Phe Glu Trp Val Ala Glu Arg Val
 75                  80                  85

GAG TTG CTT TTG AAA TCA GAA AGT CAG TGC AGG GTT GTA GTG TTG ATG          340
Glu Leu Leu Leu Lys Ser Glu Ser Gln Cys Arg Val Val Val Leu Met
 90                  95                 100                 105

GGC TCT ACT TCT GAT CTT GGT CAC TGT GAA AAA ATC AAG AAG GCC TGT          388
Gly Ser Thr Ser Asp Leu Gly His Cys Glu Lys Ile Lys Lys Ala Cys
                110                 115                 120

GGA AAT TTT GGC ATT CCA TGT GAA CTT CGA GTA ACA TCT GCG CAT AAA          436
Gly Asn Phe Gly Ile Pro Cys Glu Leu Arg Val Thr Ser Ala His Lys
            125                 130                 135

GGA CCA GAT GAA ACT CTG AGG ATT AAA GCT GAG TAT GAA GGG GAT GGC          484
Gly Pro Asp Glu Thr Leu Arg Ile Lys Ala Glu Tyr Glu Gly Asp Gly
        140                 145                 150

ATT CCT ACT GTA TTT GTG GCA GTG GCA GGC AGA AGT AAT GGT TTG GGA          532
Ile Pro Thr Val Phe Val Ala Val Ala Gly Arg Ser Asn Gly Leu Gly
155                 160                 165

CCA GTG ATG TCT GGG AAC ACT GCA TAT CCA GTT ATC AGC TGT CCT CCC          580
Pro Val Met Ser Gly Asn Thr Ala Tyr Pro Val Ile Ser Cys Pro Pro
170                 175                 180                 185

CTC ACA CCA GAC TGG GGA GTT CAG GAT GTG TGG TCT TCT CTT CGA CTA          628
Leu Thr Pro Asp Trp Gly Val Gln Asp Val Trp Ser Ser Leu Arg Leu
                190                 195                 200

CCC AGT GGT CTT GGC TGT TCA ACC GTA CTT TCT CCA GAA GGA TCA GCT          676
Pro Ser Gly Leu Gly Cys Ser Thr Val Leu Ser Pro Glu Gly Ser Ala
            205                 210                 215

CAA TTT GCT GCT CAG ATA TTT GGG TTA AGC AAC CAT TTG GTA TGG AGC          724
Gln Phe Ala Ala Gln Ile Phe Gly Leu Ser Asn His Leu Val Trp Ser
        220                 225                 230

AAA CTG CGA GCA AGC ATT TTG AAC ACA TGG ATT TCC TTG AAG CAG GCT          772
Lys Leu Arg Ala Ser Ile Leu Asn Thr Trp Ile Ser Leu Lys Gln Ala
235                 240                 245

GAC AAG AAA ATC AGA GAA TGT AAT TTA TAAGAAAGAA TGCCATTGAA TTTTTTA       826
```

```
Asp Lys Lys Ile Arg Glu Cys Asn Leu
250             255

GGGGAAAAAC TACAAATTTC TAATTTAGCT GAAGGAAAAT CAAGCAAGAT GAAAAGGTAA      886

TTTTAAATTA GAGAACACAA ATAAAATGTA TTAGTGAATA AATGGTGAGG GTAGGCCTAT      946

TCAGATGCAA GGCCAGCAAT GGGGCTCCCC ATTATCCCCA CCCCTTTGGT CCCAGTCCCC     1006

TTCTCTGCAA TGGGCACGCA TAGAGGAGAG ACAAAGGGTA TTAGACGCAA CATCATTGGC     1066

CCAGGGGAGT CCGAGAAGAG CTGCCATTGG CTGACAGGGC ATTTTCAGGC TCTGTCATTG     1126

GTCAGGGAGC ACACCCCAGC CTGAAGAGTG ATGCCATTGG CCAGGGAGTG GTTTTGTCAT     1186

AGCCGTTGGC TGTGAAGTGG AAGGAAAAGA TCTGGGAATG AAGCCCTGTG CCAGGAAGA      1246

TAGACAGGGC AGCAACTTCT GGGCCTCCAG GCCCTCTTCC CACCATAGCA ATGTGGGCAA     1306

AACTGGTGTC AGGCCCCAGC CAGAAAAAGG AGCCCAAGCC AGAGGGCAAG TGACAAAGGA     1366

TGTACCATGT CCAATCTCCC ACACCCTGGG GCTGCCCTTC CCAATGTCTT TCTTGATAGC     1426

CAAGTTGGGC TGGGAGCAGC TCACTGCTCC TCTAGCCAGG AGGGTTTCTC AGCTCCTGGA     1486

GGCCGCAGCT TGATGTTGAA CTGCTGCAGG GTCTGCTCCA GCTGTTTCTG GTTCCCAGCA     1546

AAGTAGGCGG ACACAGCATT GTGGAAGAGC AGCAGCTGCT TGTGCATCAC CTTGATCTTG     1606

TTTTCTTCCA GGAACTTGAG CTTGATGGCC ACATCTCCCC GCAGCTTCTC ATACTTGTCC     1666

CGATGGGCCT GGAAAGTGGC CTGGGCACTC TCAAGTCGAC CACGTGTCCC TGCATCCCGG     1726

GGGCCTAGAC TCAGCTCCTC TAAGTCTGTT CGGTAGGCAT CATATTCCAG CCTGGCAGCC     1786

TCATACTGTT TCACAGTCAT GAGCGTGTCT TCCATGGTCT TGGTGACCAA TGTGTTGATG     1846

CTAGAGACAA AGAAGTTCAC GGCTCCTAGC AGCGTTTCCC CATTCTTGCA TAGTAGTTTC     1906

TGTGTCTCTG CATTGTAGCC AAATTCCTCC TGAAGCTCTG GGGACTTCTG GCTGAGGTCA     1966

GCAAAGGCAT CACCCAGTGC ATGCTGGGTC TGCAGCAGGC TGTAGAGGTG GGCTGTCAGT     2026

GCCCGGCCCA GCTGCAGGAC ACTCTCATAC TTGCGCTTCG TCTCACGCAG CAACTCAATC     2086

TGCAGCTCTA GCTCCAGGAT TCCGGCGCCT CCACTCCGTC CCCCGCGGGT CTGCTCTGTG     2146

TGCCATGGAC GGCATTGTCC CAGATATAGC CGTTGGTACA AAGCGGGGAT CTGACGAGCT     2206

TTTCTCTACT TGTGTCACTA ACGGACCGTT TATCATGAGC AGCAACTCGG CTTCTGCAGC     2266

AAACGGAAAT GACAGCAAGA AGTTCAAAGG TGACAGCCGA AGTGCAGGCG TCCCTCTAG      2326

AGTGATCCAC ATCCGGAAGC TCCCCATCGA CGTCACGGAG GGGGAAGTCA TCTCCCTGGG     2386

GCTGCCCTTT GGGAAGGTCA CCAACCTCCT GATGCTGAAG GGGAAAAACC AGGCCTTCAT     2446

CGAGATGAAC ACGGAGGAGG CTGCCAATAC CATGGTGAAC TACTACACCT CGGTGACCCC     2506

TGTGCTGCGC GGCCAGCCCA TCTACATCCA GTTCTCCAAC CACAAGGAGC TGAAGACCGA     2566

CAGCTCTCCC AACCAGGCGC GGGCCCAGGC GGCCCTGCAG GCGGTGAACT CGGTCCAGTC     2626

GGGGAACCTG GCCTTGGCTG CCTCGGCGGC GGCCGTGGAT GCAGGGATGG CGATGGCCGG     2686

GCAGAGCCCC GTGCTCAGGA TCATCGTGGA GAACCTCTTC TACCCTGTGA CCCTGGATGT     2746

GCTGCACCAG ATTTTCTCCA AGTTCGGCAC AGTGTTGAAG ATCATCACCT TCACCAAGAA     2806

CAACCAGTTC CAGGCCCTGC TGCAGTATGC GGACCCCGTG AGCGCCCAGC ACGCCAAGCT     2866

GTCGCTGGAC GGGCAGAACA TCTACAACGC CTGCTGCACG CTGCGCATCG ACTTTTCCAA     2926

GCTCACCAGC CTCAACGTCA AGTACAACAA TGACAAGAGC CGTGACTACC TCGTGCCGAA     2986

TTCTTTGGAT CC                                                        2998

(2) INFORMATION FOR SEQ ID NO:150:
```

(i) SEQUENCE CHARACTERISTICS:
    (A) LENGTH: 258 amino acids
    (B) TYPE: amino acid
    (C) STRANDEDNESS: single
    (D) TOPOLOGY: linear (ii) MOLECULE TYPE: protein (v) FRAGMENT TYPE: internal (xi) SEQUENCE DESCRIPTION: SEQ ID NO:150:

```
Ala Thr Gln Ala Ile Phe Glu Ile Leu Glu Lys Ser Trp Leu Pro Gln
 1               5                  10                  15

Asn Cys Thr Leu Val Asp Met Lys Ile Glu Phe Gly Val Asp Val Thr
            20                  25                  30

Thr Lys Glu Ile Val Leu Ala Asp Val Ile Asp Asn Asp Ser Trp Arg
        35                  40                  45

Leu Trp Pro Ser Gly Asp Arg Ser Gln Gln Lys Asp Lys Gln Ser Tyr
    50                  55                  60

Arg Asp Leu Lys Glu Val Thr Pro Glu Gly Leu Gln Met Val Lys Lys
65                  70                  75                  80

Asn Phe Glu Trp Val Ala Glu Arg Val Glu Leu Leu Lys Ser Glu
                85                  90                  95

Ser Gln Cys Arg Val Val Val Leu Met Gly Ser Thr Ser Asp Leu Gly
            100                 105                 110

His Cys Glu Lys Ile Lys Lys Ala Cys Gly Asn Phe Gly Ile Pro Cys
        115                 120                 125

Glu Leu Arg Val Thr Ser Ala His Lys Gly Pro Asp Glu Thr Leu Arg
    130                 135                 140

Ile Lys Ala Glu Tyr Glu Gly Asp Gly Ile Pro Thr Val Phe Val Ala
145                 150                 155                 160

Val Ala Gly Arg Ser Asn Gly Leu Gly Pro Val Met Ser Gly Asn Thr
                165                 170                 175

Ala Tyr Pro Val Ile Ser Cys Pro Pro Leu Thr Pro Asp Trp Gly Val
        180                 185                 190

Gln Asp Val Trp Ser Ser Leu Arg Leu Pro Ser Gly Leu Gly Cys Ser
    195                 200                 205

Thr Val Leu Ser Pro Glu Gly Ser Ala Gln Phe Ala Ala Gln Ile Phe
    210                 215                 220

Gly Leu Ser Asn His Leu Val Trp Ser Lys Leu Arg Ala Ser Ile Leu
225                 230                 235                 240

Asn Thr Trp Ile Ser Leu Lys Gln Ala Asp Lys Lys Ile Arg Glu Cys
                245                 250                 255

Asn Leu
```

(2) INFORMATION FOR SEQ ID NO:151:

(i) SEQUENCE CHARACTERISTICS:
    (A) LENGTH: 1038 amino acids
    (B) TYPE: amino acid
    (C) STRANDEDNESS: single
    (D) TOPOLOGY: linear (xi) SEQUENCE DESCRIPTION: SEQ ID NO:151:

```
Ile Gln Arg Phe Gly Thr Ser Gly His Ile Met Asn Leu Gln Ala Gln
 1               5                  10                  15

Pro Lys Ala Gln Asn Lys Arg Lys Arg Cys Leu Phe Gly Gly Gln Glu
            20                  25                  30
```

```
Pro Ala Pro Lys Glu Gln Pro Pro Leu Gln Pro Pro Gln Gln Ser
        35                  40                  45

Ile Arg Val Lys Glu Glu Gln Tyr Leu Gly His Glu Gly Pro Gly Gly
50                  55                  60

Ala Val Ser Thr Ser Gln Pro Val Glu Leu Pro Pro Pro Ser Ser Leu
65                  70                  75                  80

Ala Leu Leu Asn Ser Val Val Tyr Gly Pro Glu Arg Thr Ser Ala Ala
                85                  90                  95

Met Leu Ser Gln Gln Val Ala Ser Val Lys Trp Pro Asn Ser Val Met
            100                 105                 110

Ala Pro Gly Arg Gly Pro Glu Arg Gly Gly Gly Gly Val Ser Asp
        115                 120                 125

Ser Ser Trp Gln Gln Gln Pro Gly Gln Pro Pro His Ser Thr Trp
    130                 135                 140

Asn Cys His Ser Leu Ser Leu Tyr Ser Ala Thr Lys Gly Ser Pro His
145                 150                 155                 160

Pro Gly Val Gly Val Pro Thr Tyr Tyr Asn His Pro Glu Ala Leu Lys
                165                 170                 175

Arg Glu Lys Ala Gly Gly Pro Gln Leu Asp Arg Tyr Val Arg Pro Met
            180                 185                 190

Met Pro Gln Lys Val Gln Leu Glu Val Gly Arg Pro Gln Ala Pro Leu
        195                 200                 205

Asn Ser Phe His Ala Ala Lys Lys Pro Pro Asn Gln Ser Leu Pro Leu
    210                 215                 220

Gln Pro Phe Gln Leu Ala Phe Gly His Gln Val Asn Arg Gln Val Phe
225                 230                 235                 240

Arg Gln Gly Pro Pro Pro Asn Pro Val Ala Ala Phe Pro Pro Gln
                245                 250                 255

Lys Gln Gln Gln Gln Gln Pro Gln Gln Gln Gln Gln Gln Gln
            260                 265                 270

Ala Ala Leu Pro Gln Met Pro Leu Phe Glu Asn Phe Tyr Ser Met Pro
        275                 280                 285

Gln Gln Pro Ser Gln Gln Pro Gln Asp Phe Gly Leu Gln Pro Ala Gly
    290                 295                 300

Pro Leu Gly Gln Ser His Leu Ala His His Ser Met Ala Pro Tyr Pro
305                 310                 315                 320

Phe Pro Pro Asn Pro Asp Met Asn Pro Glu Leu Arg Lys Ala Leu Leu
                325                 330                 335

Gln Asp Ser Ala Pro Gln Pro Ala Leu Pro Gln Val Gln Ile Pro Phe
            340                 345                 350

Pro Arg Arg Ser Arg Arg Leu Ser Lys Glu Gly Ile Leu Pro Pro Ser
        355                 360                 365

Ala Leu Asp Gly Ala Gly Thr Gln Pro Gly Gln Glu Ala Thr Gly Asn
    370                 375                 380

Leu Phe Leu His His Trp Pro Leu Gln Gln Pro Pro Gly Ser Leu
385                 390                 395                 400

Gly Gln Pro His Pro Glu Ala Leu Gly Phe Pro Leu Glu Leu Arg Glu
                405                 410                 415

Ser Gln Leu Leu Pro Asp Gly Glu Arg Leu Ala Pro Asn Gly Arg Glu
            420                 425                 430

Arg Glu Ala Pro Ala Met Gly Ser Glu Glu Gly Met Arg Ala Val Ser
        435                 440                 445
```

-continued

```
Thr Gly Asp Cys Gly Gln Val Leu Arg Gly Val Ile Gln Ser Thr
450                 455                 460
Arg Arg Arg Arg Arg Ala Ser Gln Glu Ala Asn Leu Leu Thr Leu Ala
465                 470                 475                 480
Gln Lys Ala Val Glu Leu Ala Ser Leu Gln Asn Ala Lys Asp Gly Ser
                485                 490                 495
Gly Ser Glu Glu Lys Arg Lys Ser Val Leu Ala Ser Thr Thr Lys Cys
            500                 505                 510
Gly Val Glu Phe Ser Glu Pro Ser Leu Ala Thr Lys Arg Ala Arg Glu
        515                 520                 525
Asp Ser Gly Met Val Pro Leu Ile Ile Pro Val Ser Val Pro Val Arg
530                 535                 540
Thr Val Asp Pro Thr Glu Ala Ala Gln Ala Gly Gly Leu Asp Glu Asp
545                 550                 555                 560
Gly Lys Gly Leu Glu Gln Asn Pro Ala Glu His Lys Pro Ser Val Ile
                565                 570                 575
Val Thr Arg Arg Arg Ser Thr Arg Ile Pro Gly Thr Asp Ala Gln Ala
                580                 585                 590
Gln Ala Glu Asp Met Asn Val Lys Leu Glu Gly Glu Pro Ser Val Arg
        595                 600                 605
Lys Pro Lys Gln Arg Pro Arg Pro Glu Pro Leu Ile Ile Pro Thr Lys
610                 615                 620
Ala Gly Thr Phe Ile Ala Pro Pro Val Tyr Ser Asn Ile Thr Pro Tyr
625                 630                 635                 640
Gln Ser His Leu Arg Ser Pro Val Arg Leu Ala Asp His Pro Ser Glu
                645                 650                 655
Arg Ser Phe Glu Leu Pro Pro Tyr Thr Pro Pro Ile Leu Ser Pro
                660                 665                 670
Val Arg Glu Gly Ser Gly Leu Tyr Phe Asn Ala Ile Ile Ser Thr Ser
        675                 680                 685
Thr Ile Pro Ala Pro Pro Ile Thr Pro Lys Ser Ala His Arg Thr
690                 695                 700
Leu Leu Arg Thr Asn Ser Ala Glu Val Thr Pro Val Leu Ser Val
705                 710                 715                 720
Met Gly Glu Ala Thr Pro Val Ser Ile Glu Pro Arg Ile Asn Val Gly
                725                 730                 735
Ser Arg Phe Gln Ala Glu Ile Pro Leu Met Arg Asp Arg Ala Leu Ala
                740                 745                 750
Ala Ala Asp Pro His Lys Ala Asp Leu Val Trp Gln Pro Trp Glu Asp
            755                 760                 765
Leu Glu Ser Ser Arg Glu Lys Gln Arg Gln Val Glu Asp Leu Leu Thr
770                 775                 780
Ala Ala Cys Ser Ser Ile Phe Pro Gly Ala Gly Thr Asn Gln Glu Leu
785                 790                 795                 800
Ala Leu His Cys Leu His Glu Ser Arg Gly Asp Ile Leu Glu Thr Leu
                805                 810                 815
Asn Lys Leu Leu Leu Lys Lys Pro Leu Arg Pro His Asn His Pro Leu
                820                 825                 830
Ala Thr Tyr His Tyr Thr Gly Ser Asp Gln Trp Lys Met Ala Glu Arg
            835                 840                 845
Lys Leu Phe Asn Lys Gly Ile Ala Ile Tyr Lys Lys Asp Phe Phe Leu
        850                 855                 860
Val Gln Lys Leu Ile Gln Thr Lys Thr Val Ala Gln Cys Val Glu Phe
```

```
                865                 870                 875                 880
Tyr Tyr Thr Tyr Lys Lys Gln Val Lys Ile Gly Arg Asn Gly Thr Leu
                885                 890                 895

Thr Phe Gly Asp Val Asp Thr Ser Asp Glu Lys Ser Ala Gln Glu Glu
                900                 905                 910

Val Glu Val Asp Ile Lys Thr Ser Gln Lys Phe Pro Arg Val Pro Leu
                915                 920                 925

Pro Arg Arg Glu Ser Pro Ser Glu Glu Arg Leu Glu Pro Lys Arg Glu
                930                 935                 940

Val Lys Glu Pro Arg Lys Glu Gly Glu Glu Val Pro Glu Ile Gln
945                 950                 955                 960

Glu Lys Glu Glu Gln Glu Gly Arg Glu Arg Ser Arg Arg Ala Ala
                965                 970                 975

Ala Val Lys Ala Thr Gln Thr Leu Gln Ala Asn Glu Ser Ala Ser Asp
                980                 985                 990

Ile Leu Ile Leu Arg Ser His Glu Ser Asn Ala Pro Gly Ser Ala Gly
                995                 1000                1005

Gly Gln Ala Ser Glu Lys Pro Arg Glu Gly Thr Gly Lys Ser Arg Arg
        1010                1015                1020

Ala Leu Pro Phe Ser Glu Lys Lys Lys Lys Gln Lys Ala
1025                1030                1035
```

(2) INFORMATION FOR SEQ ID NO:152:

(i) SEQUENCE CHARACTERISTICS:
        (A) LENGTH: 849 amino acids
        (B) TYPE: amino acid
        (C) STRANDEDNESS: single
        (D) TOPOLOGY: linear (xi) SEQUENCE DESCRIPTION: SEQ ID NO:152:

```
Ile Arg His Glu Val Ser Phe Leu Trp Asn Thr Glu Ala Ala Cys Pro
1               5                   10                  15

Ile Gln Thr Thr Thr Asp Thr Asp Gln Ala Cys Ser Ile Arg Asp Pro
                20                  25                  30

Asn Ser Gly Phe Val Phe Asn Leu Asn Pro Leu Asn Ser Ser Gln Gly
                35                  40                  45

Tyr Asn Val Ser Gly Ile Gly Lys Ile Phe Met Phe Asn Val Cys Gly
        50                  55                  60

Thr Met Pro Val Cys Gly Thr Ile Leu Gly Lys Pro Ala Ser Gly Cys
65                  70                  75                  80

Glu Ala Glu Thr Gln Thr Glu Glu Leu Lys Asn Trp Lys Pro Ala Arg
                85                  90                  95

Pro Val Gly Ile Glu Lys Ser Leu Gln Leu Ser Thr Glu Gly Phe Ile
                100                 105                 110

Thr Leu Thr Tyr Lys Gly Pro Leu Ser Ala Lys Gly Thr Ala Asp Ala
                115                 120                 125

Phe Ile Val Arg Phe Val Cys Asn Asp Asp Val Tyr Ser Gly Pro Leu
                130                 135                 140

Lys Phe Leu His Gln Asp Ile Asp Ser Gly Gln Gly Ile Arg Asn Thr
145                 150                 155                 160

Tyr Phe Glu Phe Glu Thr Ala Leu Ala Cys Val Pro Ser Pro Val Asp
                165                 170                 175

Cys Gln Val Thr Asp Leu Ala Gly Asn Glu Tyr Asp Leu Thr Gly Leu
                180                 185                 190
```

-continued

```
Ser Thr Val Arg Lys Pro Trp Thr Ala Val Asp Thr Ser Val Asp Gly
        195                 200                 205

Arg Lys Arg Thr Phe Tyr Leu Ser Val Cys Asn Pro Leu Pro Tyr Ile
        210                 215                 220

Pro Gly Cys Gln Gly Ser Ala Val Gly Ser Cys Leu Val Ser Glu Gly
225                 230                 235                 240

Asn Ser Trp Asn Leu Gly Val Val Gln Met Ser Pro Gln Ala Ala Ala
                245                 250                 255

Asn Gly Ser Leu Ser Ile Met Tyr Val Asn Gly Asp Lys Cys Gly Asn
                260                 265                 270

Gln Arg Phe Ser Thr Arg Ile Thr Phe Glu Cys Ala Gln Ile Ser Gly
        275                 280                 285

Ser Pro Ala Phe Gln Leu Gln Asp Gly Cys Glu Tyr Val Phe Ile Trp
        290                 295                 300

Arg Thr Val Glu Ala Cys Pro Val Val Arg Val Glu Gly Asp Asn Cys
305                 310                 315                 320

Glu Val Lys Asp Pro Arg His Gly Asn Leu Tyr Asp Leu Lys Pro Leu
                325                 330                 335

Gly Leu Asn Asp Thr Ile Val Ser Ala Gly Glu Tyr Thr Tyr Tyr Phe
                340                 345                 350

Arg Val Cys Gly Lys Leu Ser Ser Asp Val Cys Pro Thr Ser Asp Lys
        355                 360                 365

Ser Lys Val Val Ser Ser Cys Gln Glu Lys Arg Glu Pro Gln Gly Phe
        370                 375                 380

His Lys Val Ala Gly Leu Leu Thr Gln Lys Leu Thr Tyr Glu Asn Gly
385                 390                 395                 400

Leu Leu Lys Met Asn Phe Thr Gly Gly Asp Thr Cys His Lys Val Tyr
                405                 410                 415

Gln Arg Ser Thr Ala Ile Phe Phe Tyr Cys Asp Arg Gly Thr Gln Arg
        420                 425                 430

Pro Val Phe Leu Lys Glu Thr Ser Asp Cys Ser Tyr Leu Phe Glu Trp
        435                 440                 445

Arg Thr Gln Tyr Ala Cys Pro Pro Phe Asp Leu Thr Glu Cys Ser Phe
        450                 455                 460

Lys Asp Gly Ala Gly Asn Ser Phe Asp Leu Ser Ser Leu Ser Arg Tyr
465                 470                 475                 480

Ser Asp Asn Trp Glu Ala Ile Thr Gly Thr Gly Asp Pro Glu His Tyr
                485                 490                 495

Leu Ile Asn Val Cys Lys Ser Leu Ala Pro Gln Ala Gly Thr Glu Pro
                500                 505                 510

Cys Pro Pro Glu Ala Ala Ala Cys Leu Leu Gly Gly Ser Lys Pro Val
        515                 520                 525

Asn Leu Gly Arg Val Arg Asp Gly Pro Gln Trp Arg Asp Gly Ile Ile
        530                 535                 540

Val Leu Lys Tyr Val Asp Gly Asp Leu Cys Pro Asp Gly Ile Arg Lys
545                 550                 555                 560

Lys Ser Thr Thr Ile Arg Phe Thr Cys Ser Glu Ser Gln Val Asn Ser
                565                 570                 575

Arg Pro Met Phe Ile Ser Ala Val Glu Asp Cys Glu Tyr Thr Phe Ala
                580                 585                 590

Trp Pro Thr Ala Thr Ala Cys Pro Met Lys Ser Asn Glu His Asp Asp
        595                 600                 605

Cys Gln Val Thr Asn Pro Ser Thr Gly His Leu Phe Asp Leu Ser Ser
```

-continued

```
            610                 615                 620
Leu Ser Gly Arg Ala Gly Phe Thr Ala Ala Tyr Ser Glu Lys Gly Leu
625                 630                 635                 640

Val Tyr Met Ser Ile Cys Gly Glu Asn Glu Asn Cys Pro Pro Gly Val
                    645                 650                 655

Gly Ala Cys Phe Gly Gln Thr Arg Ile Ser Val Gly Lys Ala Asn Lys
                660                 665                 670

Arg Leu Arg Tyr Val Asp Gln Val Leu Gln Leu Val Tyr Lys Asp Gly
            675                 680                 685

Ser Pro Cys Pro Ser Lys Ser Gly Leu Ser Tyr Lys Ser Val Ile Ser
690                 695                 700

Phe Val Cys Arg Pro Glu Ala Gly Pro Thr Asn Arg Pro Met Leu Ile
705                 710                 715                 720

Ser Leu Asp Lys Gln Thr Cys Thr Leu Phe Phe Ser Trp His Thr Pro
                725                 730                 735

Leu Ala Cys Glu Gln Ala Thr Glu Cys Ser Val Arg Asn Gly Ser Ser
                740                 745                 750

Ile Val Asp Leu Ser Pro Leu Ile His Arg Thr Gly Gly Tyr Glu Ala
            755                 760                 765

Tyr Asp Glu Ser Glu Asp Asp Ala Ser Asp Thr Asn Pro Asp Phe Tyr
770                 775                 780

Ile Asn Ile Cys Gln Pro Leu Asn Pro Met His Gly Val Pro Cys Pro
785                 790                 795                 800

Ala Gly Ala Ala Val Cys Lys Val Pro Ile Asp Gly Pro Pro Ile Asp
                805                 810                 815

Ile Gly Arg Val Ala Gly Pro Pro Ile Leu Asn Pro Ile Ala Asn Glu
            820                 825                 830

Ile Tyr Leu Asn Phe Glu Ser Ser Thr Pro Cys Gln Glu Phe Ser Cys
            835                 840                 845

Lys (2) INFORMATION FOR SEQ ID NO:153:

(i) SEQUENCE CHARACTERISTICS:
        (A) LENGTH: 852 amino acids
        (B) TYPE: amino acid
        (C) STRANDEDNESS: single
        (D) TOPOLOGY: linear (xi) SEQUENCE DESCRIPTION: SEQ ID NO:153:

Met Ala Arg Leu Ser Arg Pro Glu Arg Pro Asp Leu Val Phe Glu Glu
1               5                   10                  15

Glu Asp Leu Pro Tyr Glu Glu Ile Met Arg Asn Gln Phe Ser Val
                20                  25                  30

Lys Cys Trp Leu His Tyr Ile Glu Phe Lys Gln Gly Ala Pro Lys Pro
            35                  40                  45

Arg Leu Asn Gln Leu Tyr Glu Arg Ala Leu Lys Leu Pro Cys Ser
        50                  55                  60

Tyr Lys Leu Trp Tyr Arg Tyr Leu Lys Ala Arg Ala Gln Val Lys
65                  70                  75                  80

His Arg Cys Val Thr Asp Pro Ala Tyr Glu Asp Val Asn Asn Cys His
                85                  90                  95

Glu Arg Ala Phe Val Phe Met His Lys Met Pro Arg Leu Trp Leu Asp
            100                 105                 110

Tyr Cys Gln Phe Leu Met Asp Gln Gly Arg Val Thr His Thr Arg Arg
```

```
                115                 120                 125
Thr Phe Asp Arg Ala Leu Arg Ala Leu Pro Ile Thr Gln His Ser Arg
130                 135                 140
Ile Trp Pro Leu Tyr Leu Arg Phe Leu Arg Ser His Pro Leu Pro Glu
145                 150                 155                 160
Thr Ala Val Arg Gly Tyr Arg Arg Phe Leu Lys Leu Ser Pro Glu Ser
                165                 170                 175
Ala Glu Glu Tyr Ile Glu Tyr Leu Lys Ser Ser Asp Arg Leu Asp Glu
                180                 185                 190
Ala Ala Gln Arg Leu Ala Thr Val Val Asn Asp Glu Arg Phe Val Ser
                195                 200                 205
Lys Ala Gly Lys Ser Asn Tyr Gln Leu Trp His Glu Leu Cys Asp Leu
210                 215                 220
Ile Ser Gln Asn Pro Asp Lys Val Gln Ser Leu Asn Val Asp Ala Ile
225                 230                 235                 240
Ile Arg Gly Gly Leu Thr Arg Phe Thr Asp Gln Leu Gly Lys Leu Trp
                245                 250                 255
Cys Ser Leu Ala Asp Tyr Tyr Ile Arg Ser Gly His Phe Glu Lys Ala
                260                 265                 270
Arg Asp Val Tyr Glu Glu Ala Ile Arg Thr Val Met Thr Val Arg Asp
                275                 280                 285
Phe Thr Gln Val Phe Asp Ser Tyr Ala Gln Phe Glu Glu Ser Met Ile
290                 295                 300
Ala Ala Lys Met Glu Thr Ala Ser Glu Leu Gly Arg Glu Glu Glu Asp
305                 310                 315                 320
Asp Val Asp Leu Glu Leu Arg Leu Ala Arg Phe Glu Gln Leu Ile Ser
                325                 330                 335
Arg Arg Pro Leu Leu Leu Asn Ser Val Leu Leu Arg Gln Asn Pro His
                340                 345                 350
His Val His Glu Trp His Lys Arg Val Ala Leu His Gln Gly Arg Pro
                355                 360                 365
Arg Glu Ile Ile Asn Thr Tyr Thr Glu Ala Val Gln Thr Val Asp Pro
370                 375                 380
Phe Lys Ala Thr Gly Lys Pro His Thr Leu Trp Val Ala Phe Ala Lys
385                 390                 395                 400
Phe Tyr Glu Asp Asn Gly Gln Leu Asp Asp Ala Arg Val Ile Leu Glu
                405                 410                 415
Lys Ala Thr Lys Val Asn Phe Lys Gln Val Asp Asp Leu Ala Ser Val
                420                 425                 430
Trp Cys Gln Cys Gly Glu Leu Glu Leu Arg His Glu Asn Tyr Asp Glu
                435                 440                 445
Ala Leu Arg Leu Leu Arg Lys Ala Thr Ala Leu Pro Ala Arg Arg Ala
450                 455                 460
Glu Tyr Phe Asp Gly Ser Glu Pro Val Gln Asn Arg Val Tyr Lys Ser
465                 470                 475                 480
Leu Lys Val Trp Ser Met Leu Ala Asp Leu Glu Glu Ser Leu Gly Thr
                485                 490                 495
Phe Gln Ser Thr Lys Ala Val Tyr Asp Arg Ile Leu Asp Leu Arg Ile
                500                 505                 510
Ala Thr Pro Gln Ile Val Ile Asn Tyr Ala Met Phe Leu Glu Glu His
                515                 520                 525
Lys Tyr Phe Glu Glu Ser Phe Lys Ala Tyr Glu Arg Gly Ile Ser Leu
530                 535                 540
```

-continued

```
Phe Lys Trp Pro Asn Val Ser Asp Ile Trp Ser Thr Tyr Leu Thr Lys
545                 550                 555                 560

Phe Ile Ala Arg Tyr Gly Gly Arg Lys Leu Glu Arg Ala Arg Asp Leu
                565                 570                 575

Phe Glu Gln Ala Leu Asp Gly Cys Pro Pro Lys Tyr Ala Lys Thr Leu
            580                 585                 590

Tyr Leu Leu Tyr Ala Gln Leu Glu Glu Glu Trp Gly Leu Ala Arg His
        595                 600                 605

Ala Met Ala Val Tyr Glu Arg Ala Thr Arg Ala Val Glu Pro Ala Gln
    610                 615                 620

Gln Tyr Asp Met Phe Asn Ile Tyr Ile Lys Arg Ala Ala Glu Ile Tyr
625                 630                 635                 640

Gly Val Thr His Thr Arg Gly Ile Tyr Gln Lys Ala Ile Glu Val Leu
                645                 650                 655

Ser Asp Glu His Ala Arg Glu Met Cys Leu Arg Phe Ala Asp Met Glu
            660                 665                 670

Cys Lys Leu Gly Glu Ile Asp Arg Ala Arg Ala Ile Tyr Ser Phe Cys
        675                 680                 685

Ser Gln Ile Cys Asp Pro Arg Thr Thr Gly Ala Phe Trp Gln Thr Trp
690                 695                 700

Lys Asp Phe Glu Val Arg His Gly Asn Glu Asp Thr Ile Lys Glu Met
705                 710                 715                 720

Leu Arg Ile Arg Arg Ser Val Gln Ala Thr Tyr Asn Thr Gln Val Asn
                725                 730                 735

Phe Met Ala Ser Gln Met Leu Lys Val Ser Gly Ser Ala Thr Gly Thr
            740                 745                 750

Val Ser Asp Leu Ala Pro Gly Gln Ser Gly Met Asp Met Lys Leu
        755                 760                 765

Leu Glu Gln Arg Ala Glu Gln Leu Ala Ala Glu Ala Glu Arg Asp Gln
770                 775                 780

Pro Leu Arg Ala Gln Ser Lys Ile Leu Phe Val Arg Ser Asp Ala Ser
785                 790                 795                 800

Arg Glu Glu Leu Ala Glu Leu Ala Gln Gln Val Asn Pro Glu Glu Ile
                805                 810                 815

Gln Leu Gly Glu Asp Glu Asp Glu Asp Glu Met Asp Leu Glu Pro Asn
            820                 825                 830

Glu Val Arg Leu Glu Gln Gln Ser Val Pro Ala Ala Val Phe Gly Ser
        835                 840                 845

Leu Lys Glu Asp
850
```

(2) INFORMATION FOR SEQ ID NO:154:

(i) SEQUENCE CHARACTERISTICS:
        (A) LENGTH: 693 amino acids
        (B) TYPE: amino acid
        (C) STRANDEDNESS: single
        (D) TOPOLOGY: linear (xi) SEQUENCE DESCRIPTION: SEQ ID NO:154:

```
Met Phe Ser Ala Leu Lys Lys Leu Val Gly Ser Asp Gln Ala Pro Gly
1               5                   10                  15

Arg Asp Lys Asn Ile Pro Ala Gly Leu Gln Ser Met Asn Gln Ala Leu
            20                  25                  30

Gln Arg Arg Phe Ala Lys Gly Val Gln Tyr Asn Met Lys Ile Val Ile
```

-continued

```
            35                  40                  45
Arg Gly Asp Arg Asn Thr Gly Lys Thr Ala Leu Trp His Arg Leu Gln
 50                  55                  60
Gly Arg Pro Phe Val Glu Glu Tyr Ile Pro Thr Gln Glu Ile Gln Val
 65                  70                  75                  80
Thr Ser Ile His Trp Ser Tyr Lys Thr Thr Asp Asp Ile Val Lys Val
                     85                  90                  95
Glu Val Trp Asp Val Val Asp Lys Gly Lys Cys Lys Lys Arg Gly Asp
                100                 105                 110
Gly Leu Lys Met Glu Asn Asp Pro Gln Glu Xaa Glu Ser Glu Met Ala
            115                 120                 125
Leu Asp Ala Glu Phe Leu Asp Val Tyr Lys Asn Cys Asn Gly Val Val
130                 135                 140
Met Met Phe Asp Ile Thr Lys Gln Trp Thr Phe Asn Tyr Ile Leu Arg
145                 150                 155                 160
Glu Leu Pro Lys Val Pro Thr His Val Pro Val Cys Val Leu Gly Asn
                165                 170                 175
Tyr Arg Asp Met Gly Glu His Arg Val Ile Leu Pro Asp Asp Val Arg
                180                 185                 190
Asp Phe Ile Asp Asn Leu Asp Arg Pro Pro Gly Ser Ser Tyr Phe Arg
            195                 200                 205
Tyr Ala Glu Ser Ser Met Lys Asn Ser Phe Gly Leu Lys Tyr Leu His
            210                 215                 220
Lys Phe Asn Ile Pro Phe Leu Gln Leu Gln Arg Glu Thr Leu Leu
225                 230                 235                 240
Arg Gln Leu Glu Thr Asn Gln Leu Asp Met Asp Ala Thr Leu Glu Glu
                245                 250                 255
Leu Ser Val Gln Gln Glu Thr Glu Asp Gln Asn Tyr Gly Ile Phe Leu
                260                 265                 270
Glu Met Met Glu Ala Arg Ser Arg Gly His Ala Ser Pro Leu Ala Ala
            275                 280                 285
Asn Gly Gln Ser Pro Ser Pro Gly Ser Gln Ser Pro Val Leu Pro Ala
290                 295                 300
Pro Ala Val Ser Thr Gly Ser Ser Pro Gly Thr Pro Gln Pro Ala
305                 310                 315                 320
Pro Gln Leu Pro Leu Asn Ala Ala Pro Pro Ser Ser Val Pro Pro Val
                325                 330                 335
Pro Pro Ser Glu Ala Leu Pro Pro Ala Cys Pro Ser Ala Pro Ala
                340                 345                 350
Pro Arg Arg Ser Ile Ile Ser Arg Leu Phe Gly Thr Ser Pro Ala Thr
            355                 360                 365
Glu Ala Ala Pro Pro Pro Glu Pro Val Pro Ala Ala Gln Gly Pro
            370                 375                 380
Ala Thr Val Gln Ser Val Glu Asp Phe Val Pro Asp Asp Arg Leu Asp
385                 390                 395                 400
Arg Ser Phe Leu Glu Asp Thr Thr Pro Ala Arg Asp Glu Lys Lys Val
                405                 410                 415
Gly Ala Lys Ala Ala Gln Gln Asp Ser Asp Ser Asp Gly Glu Ala Leu
            420                 425                 430
Gly Gly Asn Pro Met Val Ala Gly Phe Gln Asp Asp Val Asp Leu Glu
            435                 440                 445
Asp Gln Pro Arg Gly Ser Pro Leu Pro Ala Gly Pro Val Pro Ser
450                 455                 460
```

-continued

```
Gln Asp Ile Thr Leu Ser Ser Glu Glu Glu Ala Glu Val Ala Ala Pro
465                 470                 475                 480

Thr Lys Gly Pro Ala Pro Ala Pro Gln Gln Cys Ser Glu Pro Glu Thr
                485                 490                 495

Lys Trp Ser Ser Ile Pro Ala Ser Lys Pro Arg Arg Gly Thr Ala Pro
                500                 505                 510

Thr Arg Thr Ala Ala Pro Pro Trp Pro Gly Gly Val Ser Val Arg Thr
            515                 520                 525

Gly Pro Glu Lys Arg Ser Ser Thr Arg Pro Pro Ala Glu Met Glu Pro
        530                 535                 540

Gly Lys Gly Glu Gln Ala Ser Ser Ser Glu Ser Asp Pro Glu Gly Pro
545                 550                 555                 560

Ile Ala Ala Gln Met Leu Ser Phe Val Met Asp Asp Pro Asp Phe Glu
                565                 570                 575

Ser Glu Gly Ser Asp Thr Gln Arg Arg Ala Asp Asp Phe Pro Val Arg
                580                 585                 590

Asp Asp Pro Ser Asp Val Thr Asp Glu Asp Glu Gly Pro Ala Glu Pro
            595                 600                 605

Pro Pro Pro Pro Lys Leu Pro Leu Pro Ala Phe Arg Leu Lys Asn Asp
        610                 615                 620

Ser Asp Leu Phe Gly Leu Gly Leu Glu Gly Ala Gly Pro Lys Glu Ser
625                 630                 635                 640

Ser Glu Glu Gly Lys Glu Gly Lys Thr Pro Ser Lys Glu Lys Lys Lys
                645                 650                 655

Lys Thr Lys Ser Phe Ser Arg Val Leu Leu Glu Arg Pro Arg Ala His
                660                 665                 670

Arg Phe Ser Thr Arg Val Gly Tyr Gln Val Ser Val Pro Asn Ser Pro
            675                 680                 685

Tyr Ser Glu Ser Tyr
    690
```

SCREENING FOR DRUGS THAT AFFECT TNF RECEPTOR RELEASING ENZYME

CROSS-REFERENCE TO RELATED APPLICATIONS

This application is a continuation of U.S. patent application Ser. No. 09/712,813, filed Nov. 13, 2000 which application is a continuation of PCT Application No. PCT/US99/10793, filed May 14, 1999, which International Application was published by the International Bureau in English on Nov. 18, 1999, which application claims the priority benefit of U.S. application Ser. No. 09/081,385, filed May 14, 1998, pending. For purposes of prosecution in the U.S., the priority applications are hereby incorporated herein by reference in their entirety.

FIELD OF THE INVENTION

This invention relates generally to the field of signal transduction between cells, via cytokines and their receptors. More specifically, it relates to enzymatic activity that cleaves and releases the receptor for TNF found on the cell surface, and the consequent biological effects. Certain embodiments of this invention are compositions that affect such enzymatic activity, and may be included in medicaments for disease treatment.

BACKGROUND OF THE INVENTION

Cytokines play a central role in the communication between cells. Secretion of a cytokine from one cell in response to a stimulus can trigger an adjacent cell to undergo an appropriate biological response—such as stimulation, differentiation, or apoptosis. It is hypothesized that important biological events can be influenced not only by affecting cytokine release from the first cell, but also by binding to receptors on the second cell, which mediates the subsequent response. The invention described in this patent application provides new compounds for affecting signal transduction from tumor necrosis factor.

The cytokine known as tumor necrosis factor (TNF or TNF-α) is structurally related to lymphotoxin (LT or TNF-β). They have about 40 percent amino acid sequence homology (Old, Nature 330:602–603, 1987). These cytokines are released by macrophages, monocytes and natural killer cells and play a role in inflammatory and immunological events. The two cytokines cause a broad spectrum of effects both in vitro and in vivo, including: (i) vascular thrombosis and tumor necrosis; (ii) inflammation; (iii) activation of macrophages and neutrophils; (iv) leukdcytosis; (v) apoptosis; and (vi) shock. TNF has been associated with a variety of disease states including various forms of cancer, arthritis, psoriasis, endotoxic shock, sepsis, autoimmune diseases, infections, obesity, and cachexia. TNF appears to play a role in the three factors contributing to body weight control: intake, expenditure, and storage of energy (Rothwell, Int. J. Obesity 17:S98–S101, 1993). In septicemia, increased endotoxin concentrations appear to raise TNF levels (Beutler et al. Science 229:869–871, 1985).

Attempts have been made to alter the course of a disease by treating the patient with TNF inhibitors, with varying degrees of success. For example, the TNF inhibitor dexanabinol provided protection against TNF mediated effects following traumatic brain injury (Shohami et al. J. Neuroimmun. 72:169–77, 1997). Some improvement in Crohn's disease was afforded by treatment with anti-TNF antibodies (Neurath et al., Eur. J. Immun. 27:1743–50, 1997).

Human TNF and LT mediate their biological activities by binding specifically to two distinct glycoprotein plasma membrane receptors (55 kDa and 75 kDa in size, known as p55 and p75 TNF-R, respectively). The two receptors share 28 percent amino acid sequence homology in their extracellular domains, which are composed of four repeating cysteine-rich regions (Tartaglia and Goeddel, Immunol. Today 13:151–153, 1992). However, the receptors lack significant sequence homology in their intracellular domains, and mediate different intracellular responses to receptor activation. In accordance with the different activities of TNF and LT, most human cells express low levels of both TNF receptors: about 2,000 to 10,000 receptors per cell (Brockhaus et al., Proc. Natl. Acad. Sci. USA 87:3127–3131, 1990).

Expression of TNF receptors on both lymphoid and non-lymphoid cells can be influenced experimentally by many different agents, such as bacterial lipopolysaccharide (LPS), phorbol myristate acetate (PMA; a protein kinase C activator), interleukin-1 (IL-1), interferon-gamma (IFN-γ) and IL-2 (Gatanaga et al. Cell Immunol. 138:1–10, 1991; Yui et al. Placenta 15:819–835, 1994). It has been shown that complexes of human TNF bound to its receptor are internalized from the cell membrane, and then the receptor is either degraded or recycled (Armitage, Curr. Opin. Immunol. 6:407–413, 1994). It has been proposed that TNF receptor activity can be modulated using peptides that bind intracellularly to the receptor, or which bind to the ligand binding site, or that affect receptor shedding. See for example patent publications WO 95/31544, WO 95/33051, WO 96/01642, and EP 568 925.

TNF binding proteins (TNF-BP) have been identified at elevated levels in the serum and urine of febrile patients, patients with renal failure, and cancer patients, and even certain healthy individuals. Human brain and ovarian tumors produced high serum levels of TNF-BP. These molecules have been purified, characterized, and cloned (Gatanaga et al., Lymphokine Res. 9:225–229, 1990a; Gatanaga et al., Proc. Natl. Acad. Sci USA 87:8781–8784, 1990b). Human TNF-BP consists of 30 kDa and 40 kDa proteins which are identical to the N-terminal extracellular domains of p55 and p75 TNF receptors, respectively (U.S. Pat. No. 5,395,760; EP 418,014). Such proteins have been suggested for use in treating endotoxic shock. Mohler et al. J. Immunol. 151:1548–1561, 1993.

There are several mechanisms possible for the production of secreted proteins resembling membrane bound receptors. One involves translation from alternatively spliced mRNAs lacking transmembrane and cytoplasmic regions. Another involves proteolytic cleavage of the intact membrane receptors, followed by shedding of the cleaved receptor from the cell. The soluble form of p55 and p75 TNF-R do not appear to be generated from mRNA splicing, since only full length receptor mRNA has been detected in human cells in vitro (Gatanaga et al., 1991). Carboxyl-terminal sequencing and mutation studies on human p55 TNF-R indicates that a cleavage site may exist between residues Asn 172 and Val 173 (Gullberg et al. Eur. J. Cell. Biol. 58:307–312, 1992).

There are reports that a specific metalloprotease inhibitor, TNF-α protease inhibitor (TAPI) blocks the shedding of soluble p75 and p55 TNF-R (Crowe et al. J. Exp. Med. 181:1205–1210, 1995; Mullberg et al. J. Immunol. 155:5198–5205, 1995). The processing of pro-TNF on the cell membrane to release the TNF ligand appears to be dependent on a matrix metalloprotease like enzyme (Gearing et al. Nature 370:555–557, 1994). This is a family of structurally related matrix-degrading enzymes that play a major role in tissue remodeling and repair associated with development and inflammation (Birkedal-Hansen et al. *Crit. Rev. Oral Biol. Med.* 4:197–250, 1993). The enzymes have $Zn^{2+}$ in their catalytic domains, and $Ca^{2+}$ stabilizes their tertiary structure significantly.

In European patent application EP 657536A1, Wallach et al. suggest that it would be possible to obtain an enzyme that cleaves the 55,000 kDa TNF receptor by finding a mutated form of the receptor that is not cleaved by the enzyme, but still binds to it. The only proposed source for the enzyme is a detergent extract of membranes for cells that appear to have the protease activity. If it were possible to obtain an enzyme according to this scheme, then the enzyme would presumably comprise a membrane spanning region. The patent application does not describe any protease that was actually obtained.

In a previous patent application in the present series (International Patent Publication WO 9820140), methods are described for obtaining an isolated enzyme that cleaves both the p55 and p75 TNF-R from cell surfaces. A convenient source is the culture medium of cells that have been stimulated with phorbol myristate acetate (PMA). The enzyme activity was given the name TRRE (TNF receptor releasing enzyme). In other studies, TRRE was released immediately upon PMA stimulation, indicating that it is presynthesized in an inactive form to be rapidly converted to the active form upon stimulation. Evidence for direct cleavage of TNF-R is that the shedding begins very quickly (~5 min) with maximal shedding within 30 min. TRRE is specific for the TNF-R, and does not cleave IL-1 receptors, CD30, ICAM-1 or CD11b. TRRE activity is enhanced by adding $Ca^{++}$ or $Zn^{++}$, and inhibited by EDTA and phenaritroline.

Given the involvement of TNF in a variety of pathological conditions, it is desirable to obtain a variety of factors that would allow receptor shedding to be modulated, thereby controlling the signal transduction from TNF at a disease site.

SUMMARY OF THE INVENTION

This disclosure provides new compounds that promote enzymatic cleavage and release of TNF receptors from the cell surface. Nine new DNA clones have been selected after repeat screening in an assay that tests the ability to enhance receptor release. The polynucleotide sequences of this invention and the proteins encoded by them have potential as diagnostic aids, and therapeutic compounds that can be used to adjust TNF signal transduction in a beneficial way.

One embodiment of the invention is an isolated polynucleotide comprising a nucleotide sequence with the following properties: a) the sequence is expressed at the mRNA level in Jurkat T cells; b) when COS-1 cells expressing TNF-receptor are genetically transformed to express the sequence, the cells have increased enzymatic activity for cleaving and releasing the receptor. If a polynucleotide sequence is expressed in Jurkat cells, then it can be found in the Jurkat cell expression library deposited with the ATCC (Accession No. TIB-152). It is recognized that the polynucleotide can be obtained from other cell lines, or produced by recombinant techniques.

Included are polynucleotides in which the nucleotide sequence is contained in any of SEQ. ID NOS:1–10. Also embodied are polynucleotides comprising at least 30 and preferably more consecutive nucleotides in said nucleotide sequence, or at least 50 consecutive nucleotides that are homologous to said sequence at a significant level, preferably at the 90% level or more. Also included antisense and ribozyme polynucleotides that inhibit the expression of a TRRE modulator.

Another embodiment of the invention is isolated polypeptides comprising an amino acid sequence encoded by a polynucleotide of this invention. Non-limiting examples are sequences shown in SEQ. ID NOS: 147–158. Fragments and fusion proteins are included in this invention, and preferably comprise at least 10 consecutive residues encoded by a polynucleotide of this invention, or at least 15 consecutive amino acids that are homologous at a significant level, preferably at least 80%. Preferred polypeptides promote cleavage and release of TNF receptors from the cell surface, especially COS-1 cells genetically transformed to express TNF receptor. The polypeptides may or may not have a membrane spanning domain, and may optionally be produced by a process that involves secretion from a cell. Included are species homologs with the desired activity, and artificial mutants with additional beneficial properties.

Another embodiment of this invention is an antibody specific for a polypeptide of this invention. Preferred are antibodies that bind a TRRE modulator protein, but not other substances found in human tissue samples in comparable amounts.

Another embodiment of the invention is an assay method of determining altered TRRE activity in a cell or tissue sample, using a polynucleotide or antibody of this invention to detect the presence or absence of the corresponding TRRE modulator. The assay method can optionally be used for the diagnosis or evaluation of a clinical condition relating to abnormal TNF levels or TNF signal transduction.

Another embodiment of the invention is a method for increasing or decreasing signal transduction from a cytokine into a cell (including but not limited to TNF), comprising contacting the cell with a polynucleotide, polypeptide, or antibody of this invention.

A further embodiment of the invention is a method for screening polynucleotides for an ability to modulate TRRE activity. The method involves providing cells that express both TRRE and the TNF-receptor; genetically altering the cells with the polynucleotides to be screened; cloning the cells; and identifying clones with the desired activity.

Yet another embodiment of the invention is a method for screening substances for an ability to affect TRRE activity. This typically involves incubating cells expressing TNF receptor with a TRRE modulator of this invention in the presence or absence of the test substance; and measuring the effect on shedding of the TNF receptor.

The products of this invention can be used in the preparation of a medicament for treatment of the human or animal body. The medicament contains a clinically effective amount for treatment of a disease such as heart failure, cachexia, inflammation, endotoxic shock, arthritis, multiple sclerosis, sepsis, and cancer. These compositions can be used for administration to a subject suspected of having or being at risk for the disease, optionally in combination with other forms of treatment appropriate for their condition.

Results from the transformed cells, designated C75R (●, upward swooping line) is compared with that from the parental COS-1 cells (■, baseline). The receptor number was calculated by Scatchard analysis (inset).

Figure 3:
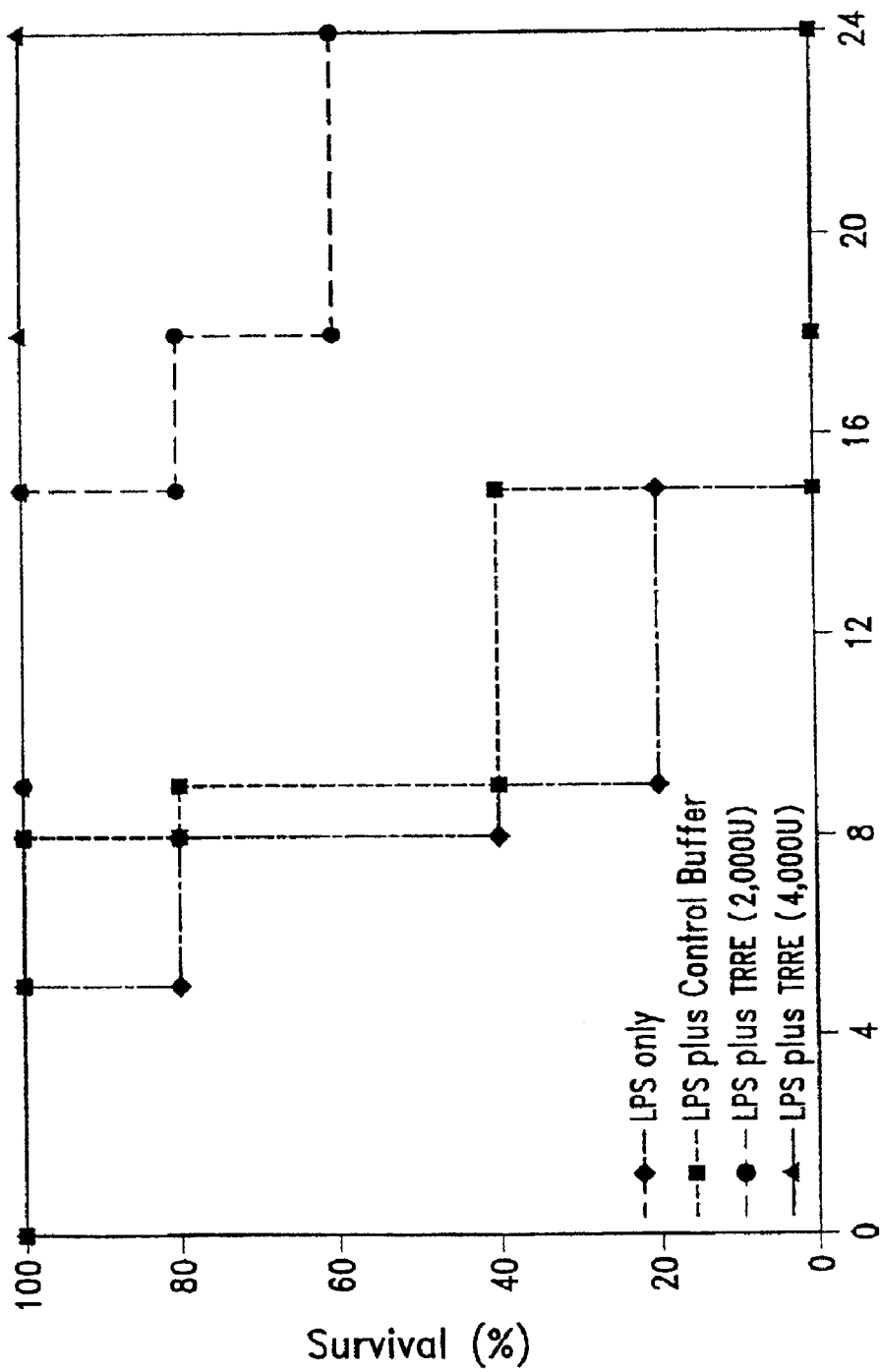

FIG. 3 is a survival graph, showing that TRRE decreases mortality in mice challenged with lipopolysaccharide (LPS) to induce septic peritonitis. (♦) LPS alone; (■) LPS plus control buffer; (●) LPS plus TRRE (2,000 U); (▲) LPS plus TRRE (4,000 U).

Figure 4:
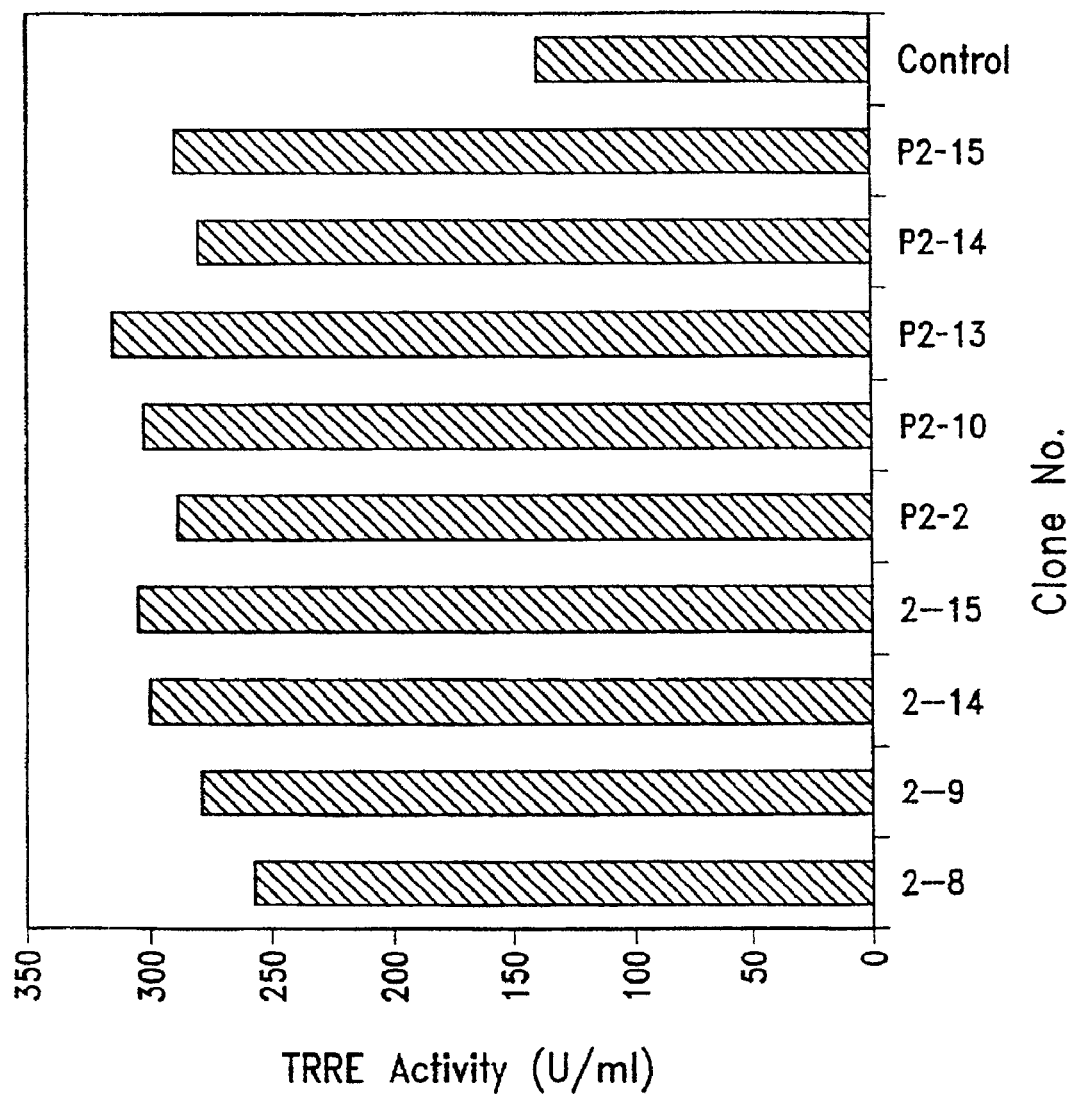

FIG. 4 is a half-tone reproduction of a bar graph, showing the effect of 9 new clones on TRRE activity on C75R cells (COS-1 cells transfected to express the TNF-receptor. Each of the 9 clones increases TRRE activity by over 2-fold.

Figure 5:
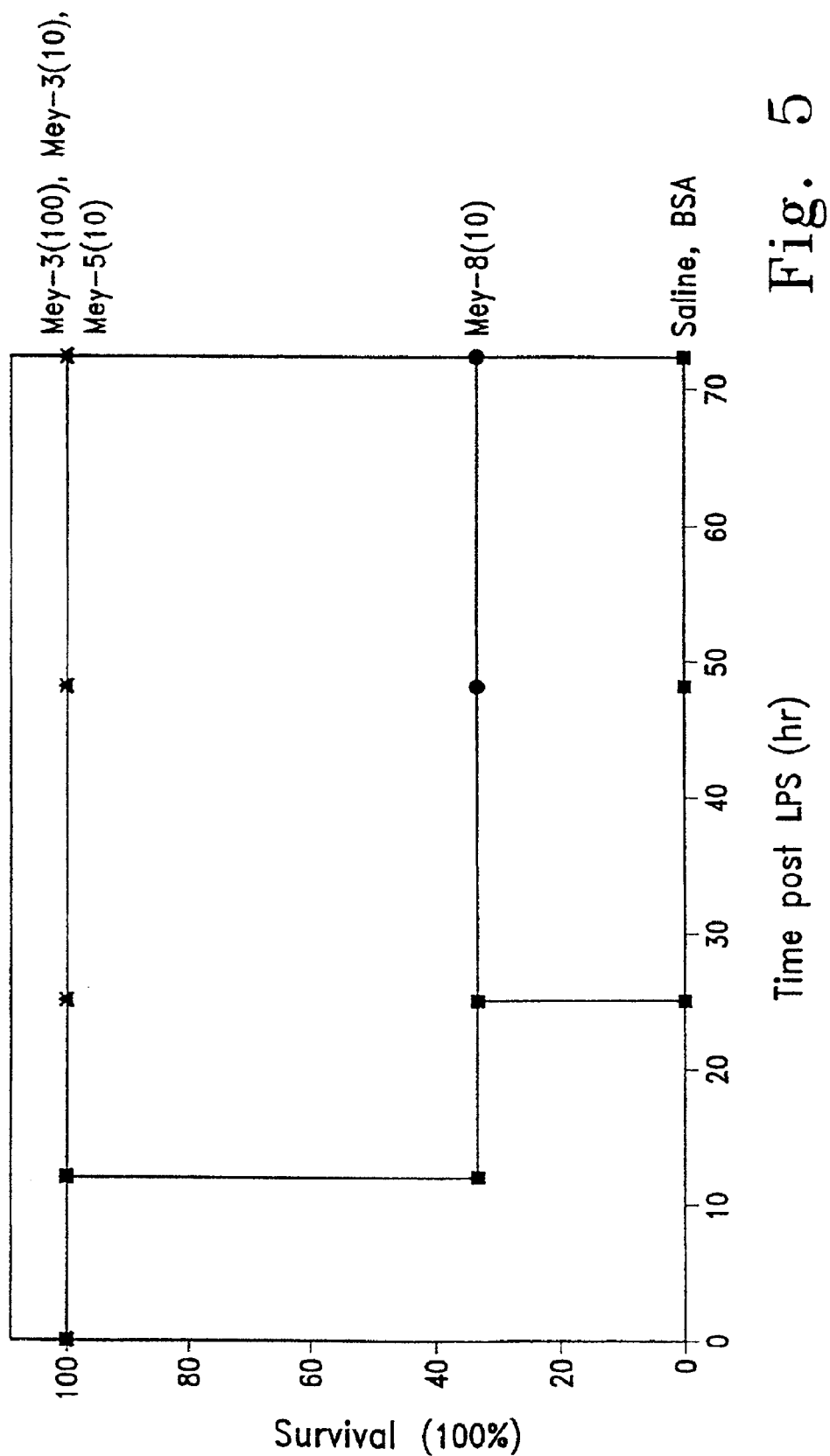

FIG. 5 is a survival graph, showing the ability of 4 new expressed to save mice challenged with LPS. (♦) saline; (■) BSA; (Δ) Mey-3 (100 µg); (X) Mey-3 (10 µg); (*) Mey-5 (10 µg); (●) Mey-8 (10 µg).

DETAILED DESCRIPTION OF THE INVENTION

It has been discovered that certain cells involved in the TNF transduction pathway express enzymatic activity that causes TNF receptors to be shed from the cell surface. Enzymatic activity for cleaving and releasing TNF receptors has been given the designation TRRE. Phorbol myristate acetate induces release of TRRE from cells into the culture medium. An exemplary TRRE protein had been purified from the supernatant of TNF-1 cells (Example 2). The protease bears certain hallmarks of the metalloprotease family, and is released rapidly from the cell upon activation.

In order to elucidate the nature of this protein, functional cloning was performed. Jurkat cells were selected as being a good source of TRRE. The cDNA from a Jurkat library was expressed, and cell supernatant was tested for an ability to release TNF receptors from cell surfaces. Cloning and testing of the expression product was conducted through several cycles, and nine clones were obtained that more than doubled TRRE activity in the assay (FIG. 4). At the DNA level, all 9 clones had different sequences.

Protein expression products from the clones have been tested in a lipopolysaccharide animal model for sepsis. Protein from three different clones successfully rescued animals from a lethal dose of LPS (FIG. 5). This points to an important role for these molecules in the management of pathological conditions mediated by TNF.

The number of new TRRE promoting clones obtained from the expression library was surprising. The substrate specificity of the TRRE isolated in Example 2 distinguishes the 75 kDa and 55 kDa TNF receptors from other cytokine receptors and cell surface proteins. There was little reason beforehand to suspect that cells might have nine different proteases for the TNF receptor. It is possible that one of the clones encodes the TRRE isolated in Example 2, or a related protein. It is possible that some of the other clones have proteolytic activity to cleave TNF receptors at the same site, or at another site that causes release of the soluble form from the cell. It is a hypothesis of this disclosure that some of the clones may not have proteolytic activity themselves, but play a role in promoting TRRE activity in a secondary fashion.

This possibility is consistent with the observations made, because there is an endogenous level of TRRE activity in the cells used in the assay. The cleavage assay involves monitoring TNF receptor release from C75 cells, which are COS-1 cells genetically altered to express p75 TNF-R. The standard assay is conducted by contacting the transformed cells with a fluid believed to contain TRRE. The level of endogenous TRRE activity is evident from the rate of spontaneous release of the receptor even when no exogenous TRRE is added (about 200 units). Accordingly, accessory proteins that promote TRRE activity would increase the activity measured in the assay. Many mechanisms of promotion are possible, including proteins that activate a zymogen form of TRRE, proteins that free TRRE from other cell surface components, or proteins that stimulate secretion of TRRE from inside the cell. It is not necessary to understand the mechanism in order to use the products of this invention in most of the embodiments described.

It is anticipated that several of the clones will have activity not just for promoting TNF receptor cleavage, but also having an effect on other surface proteins. To the extent that cleavage sequences or accessory proteins are shared between different receptors, certain clones would promote phenotypic change (such as receptor release) for the family of related substrates.

This disclosure provides polypeptides that promote TRRE activity, polynucleotides that encode such polypeptides, and antibodies that bind such peptides. The binding of TNF to its receptor mediates a number of biological effects. Cleavage of the TNF-receptor by TRRE diminishes signal transduction by TRRE. Potentiators of TRRE activity have the same effect. Thus, the products of this invention can be used to modulate signal transduction by cytokines, which is of considerable importance in the management of disease conditions that are affected by cytokine action. The products of this invention can also be used in diagnostic methods, to determine when signal transduction is being inappropriately affected by abnormal TRRE activity. The assay systems described in this disclosure provide a method for screening additional compounds that can influence TRRE activity, and thus the signal transduction from TNF.

Based on the summary of the invention, and guided by the illustrations in the example section, one skilled in the art will readily know what techniques to employ in the practice of the invention. The following detailed description is provided for the additional convenience of the reader.

Definitions and Basic Techniques

As used in this disclosure, "TRRE activity" refers to the ability of a composition to cleave and release TNF receptors from the surface of cells expressing them. A preferred assay is cleavage from transfected COS-1 cells, as described in Example 1. However, TRRE activity can be measured on any cells that bear TNF receptors of the 55 kDa or 75 kDa size. Other features of the TRRE enzyme obtained from PMA induction of THP-1 cells (exemplified in Example 2) need not be a property of the TRRE activity measured in the assay.

Unit activity of TRRE is defined as 1 pg of soluble p75 TNF-R released from cell surface in a standard assay, after correction for spontaneous release. The measurement of TRRE activity is explained further in Example 1.

A "TRRE modulator" is a compound that has the property of either increasing or decreasing TRRE activity for processing TNF on the surface of cells. Those that increase TRRE activity may be referred to as TRRE promoters, and those that decrease TRRE activity may be referred to as TRRE inhibitors. TRRE promoters include compounds that have proteolytic activity for TNF-R, and compounds that augment the activity of TNF-R proteases. The nine polynucleotide clones described in Example 5, and their protein products, are exemplary TRRE promoters. Inhibitors of TRRE activity can be obtained using the screening assays described below.

The term "polynucleotide" refers to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, (mRNA), ribozymes, cDNA, recombinant polynucleotides, branched polynucleotides, plasmids, vectors, nucleic acid probes, and primers. A polynucleotide may comprise modified nucleotides, such as methylated nucleotides and nucleotide analogs. If present, modifications to the nucleotide structure may be imparted before or after assembly of the polymer. The term polynucleotide refers interchangeably to double- and single-stranded molecules. Unless otherwise specified or required, any embodiment of the invention described herein that is a polynucleotide encompasses both the double-stranded form, and each of two complementary single-stranded forms known or predicted to make up the double-stranded form "Hybridization" refers to a reaction in which one or more polynucleotides react to form a complex that is stabilized via hydrogen bonding between the bases of the nucleotide residues. Hybridization reactions can be performed under conditions of different "stringency". Relevant conditions include temperature, ionic strength, and the presence of additional solutes in the reaction mixture such as formamide. Conditions of increasing stringency are 30° C. in 10×SSC (0.15M NaCl, 15 mM citrate buffer); 40° C. in 6×SSC; 50° C. in 6.×SSC 60° C. in 6×SSC, or at about 40° C. in 0.5×SSC, or at about 30° C. in 6.×SSC containing 50% formamide. SDS and a source of fragmented DNA (such as salmon sperm) are typically also present during hybridization. Higher stringency requires higher minimum complementarity between hybridizing elements for a stable hybridization complex to form. See "Molecular Cloning: A Laboratory Manual", Second Edition (Sambrook, Fritsch & Maniatis, 1989).

It is understood that purine and pyrimidine nitrogenous bases with similar structures can be functionally equivalent in terms of Watson-Crick base-pairing; and the inter-substitution of like nitrogenous bases, particularly uracil and thymine, or the modification of nitrogenous bases, such as by methylation, does not constitute a material substitution.

The percentage of sequence identity for polynucleotides or polypeptides is calculated by aligning the sequences being compared, and then counting the number of shared residues at each aligned position. No penalty is imposed for the presence of insertions or deletions, but are permitted only where required to accommodate an obviously increased number of amino acid residues in one of the sequences being aligned. When one of the sequences being compared is indicated as being "consecutive", then no gaps are permitted in that sequence during the comparison. The percentage identity is given in terms of residues in the test sequence that are identical to residues in the comparison or reference sequence.

As used herein, "expression" of a polynucleotide refers to the production of an RNA transcript. Subsequent translation into protein or other effector compounds may also occur, but is not required unless specified.

"Genetic alteration" refers to a process wherein a genetic element is introduced into a cell other than by mitosis or meiosis. The element may be heterologous to the cell, or it may be an additional copy or improved version of an element already present in the cell. Genetic alternation may be effected, for example, by transducing a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. It is preferable that the genetic alteration is inheritable by progeny of the cell, but this is not generally required unless specified.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component.

A "fusion polypeptide" is a polypeptide comprising regions in a different position in the sequence than occurs in nature. The regions can normally exist in separate proteins and are brought together in the fusion polypeptide; they can normally exist in the same protein but are placed in a new arrangement in the fusion polypeptide; or they can be synthetically arranged. A "functionally equivalent fragment" of a polypeptide varies from the native sequence by addition, deletion, or substitution of amino acid residues, or any combination thereof, while preserving a functional property of the fragment relevant to the context in which it is being used. Fusion peptides and functionally equivalent fragments are included in the definition of polypeptides used in this disclosure.

It is understood that the folding and the biological function of proteins can accommodate insertions, deletions, and substitutions in the amino acid sequence. Some amino acid substitutions are more easily tolerated. For example, substitution of an amino acid with hydrophobic side chains, aromatic side chains, polar side chains, side chains with a positive or negative charge, or side chains comprising two or fewer carbon atoms, by another amino acid with a side chain of like properties can occur without disturbing the essential identity of the two sequences. Methods for determining homologous regions and scoring the degree of homology are described in Altschul et al. *Bull. Math. Bio.* 48:603–616, 1986; and Henikoff et al. *Proc. Natl. Acad. Sci. USA* 89:10915–10919, 1992. Substitutions that preserve the functionality of the polypeptide, or confer a new and beneficial property (such as enhanced activity, stability, or decreased immunogenicity) are especially preferred.

An "antibody" (interchangeably used in plural form) is an immunoglobulin molecule capable of specific binding to a target, such as a polypeptide, through at least one antigen recognition site, located in the variable region of the immunoglobulin molecule. As used herein, the term encompasses not only intact antibodies, but also antibody equivalents that include at least one antigen combining site of the desired specificity. These include but are not limited to enzymatic or recombinantly produced fragments antibody, fusion proteins, humanized antibodies, single chain variable regions, diabodies, and antibody chains that undergo antigen-induced assembly.

An "isolated" polynucleotide, polypeptide, protein, antibody, or other substance refers to a preparation of the substance devoid of at least some of the other components that may also be present where the substance or a similar substance naturally occurs or is initially obtained from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred. A substance can also be provided in an isolated state by a process of artificial assembly, such as by chemical synthesis or recombinant expression.

A "host cell" is a cell which has been genetically altered, or is capable of being transformed, by administration of an exogenous polynucleotide.

The term "clinical sample" encompasses a variety of sample types obtained from a subject and useful in an in vitro procedure, such as a diagnostic test. The definition encompasses solid tissue samples obtained as a surgical removal, a pathology specimen, or a biopsy specimen, cells obtained from a clinical subject or their progeny obtained from culture, liquid samples such as blood, serum, plasma, spinal fluid, and urine, and any fractions or extracts of such samples that contain a potential indication of the disease.

Unless otherwise indicated, the practice of the invention will employ conventional techniques of molecular biology, microbiology, recombinant DNA, and immunology, within the skill of the art. Such techniques are explained in the standard literature, such as: "Molecular Cloning: A Laboratory Manual", Second Edition (Sambrook, Fritsch & Maniatis, 1989), "Oligonucleotide Synthesis" (M. J. Gait, ed., 1984), "Animal Cell Culture" (R. I. Freshney, ed., 1987); the series "Methods in Enzymology" (Academic Press, Inc.); "Handbook of Experimental Immunology" (D. M. Weir & C. C. Blackwell, Eds.), "Gene Transfer Vectors for Mammalian Cells" (J. M. Miller & M. P. Calos, eds., 1987), "Current Protocols in Molecular Biology" (F. M. Ausubel et al., eds., 1987); and "Current Protocols in Immunology" (J. E. Coligan et al., eds., 1991). The reader may also choose to refer to a previous patent application relating to TRRE, International Patent Application WO 98020140.

For purposes of prosecution in the U.S., and in other jurisdictions where allowed, all patents, patent applications, articles and publications indicated anywhere in this disclosure are hereby incorporated herein by reference in their entirety.

Polynucleotides

Polynucleotides of this invention can be prepared by any suitable technique in the art. Using the data provided in this disclosure, sequences of less than ~50 base pairs are conveniently prepared by chemical synthesis, either through a commercial service or by a known synthetic method, such as the triester method or the phosphite method. A preferred method is solid phase synthesis using mononucleoside phosphoramidite coupling units (Hirose et al., Tetra. Lett. 19:2449–2452, 1978; U.S. Pat. No. 4,415,732).

For use in antisense therapy, polynucleotides can be prepared by chemistry that produce more stable in pharmaceutical preparations. Non-limiting examples include thiol-derivatized nucleosides (U.S. Pat. No. 5,578,718), and oligonucleotides with modified backbones (U.S. Pat. Nos. 5,541,307 and 5,378,825).

Polynucleotides of this invention can also be obtained by PCR amplification of a template with the desired sequence. Oligonucleotide primers spanning the desired sequence are annealed to the template, elongated by a DNA polymerase, and then melted at higher temperature so that the template and elongated oligonucleotides dissociate. The cycle is repeated until the desired amount of amplified polynucleotide is obtained (U.S. Pat. Nos. 4,683,195 and 4,683,202). Suitable templates include the Jurkat T cell library and other human or animal expression libraries that contain TRRE modulator encoding sequences. The Jurkat T cell library is available from the American Type Culture Collection, 10801 University Blvd., Manassas Va. 20110, U.S.A. (ATCC #TIB-152). Mutations and other adaptations can be performed during amplification by designing suitable primers, or can be incorporated afterwards by genetic splicing.

Production scale amounts of large polynucleotides are most conveniently obtained by inserting the desired sequence into a suitable cloning vector and reproducing the clone. Techniques for nucleotide cloning are given in Sambrook, Fritsch & Maniatis (supra) and in U.S. Pat. No. 5,552,524. Exemplary cloning and expression methods are illustrated in Example 6.

Preferred polynucleotide sequences are 50%, 70%, 80%, 90%, or 100% identical to one of the sequences exemplified in this disclosure; in order if increasing preference. The length of consecutive residues in the identical or homologous sequence compared with the exemplary sequence can be about 15, 30, 50, 75, 100, 200 or 500 residues in order of increasing preference, up to the length of the entire clone. Nucleotide changes that cause a conservative substitution or retain the function of the encoded polypeptide (in terms of hybridization properties or what is encoded) are especially preferred substitutions.

The polynucleotides of this can be used to measure altered TRRE activity in a cell or tissue sample. This involves contacting the sample with the polynucleotide under conditions that permit the polynucleotide to hybridize specifically with nucleic acid that encodes a modulator of TRRE activity, if present in the sample, and determining polynucleotide that has hybridized as a result of step a). Specificity of the test can be provided in one of several ways. One method involves the use of a specific probe—a polynucleotide of this invention with a sequence long enough and of sufficient identity to the sequence being detected, so that it binds the target and not other nucleic acid that might be present in the sample. The probe is typically labeled (either directly or through a secondary reagent) so that it can be subsequently detected. Suitable labels include $^{32}P$ and $^{33}P$, chemiluminescent and fluorescent reagents. After the hybridization reaction, unreacted probe is washed away so that the amount of hybridized probe can be determined. Signal can be amplified using branched probes (U.S. Pat. No. 5,124,246). In another method, the polynucleotide is a primer for a PCR reaction. Specificity is provided by the ability of the paired probes to amplify the sequence of interest. After a suitable number of PCR cycles, the amount of amplification product present correlates with the amount of target sequence originally present in the sample.

Such tests are useful both in research, and in the diagnosis or assessment of a disease condition. For example, TNF activity plays a role in eliminating tumor cells (Example 4), and a cancer may evade the elimination process by activating TRRE activity in the diseased tissue. Hence, under some conditions, high expression of TRRE modulators may correlate with progression of cancer. Diagnostic tests are also of use in monitoring therapy, such as when gene therapy is performed to increase TRRE activity.

Polynucleotides of this invention can also be used for production of polypeptides and the preparation of medicaments, as explained below.

Polypeptides

Short polypeptides of this invention can be prepared by solid-phase chemical synthesis. The principles of solid phase chemical synthesis can be found in Dugas & Penney, Bioorganic Chemistry, Springer-Verlag NY pp 54–92 (1981), and U.S. Pat. No. 4,493,795. Automated solid-phase peptide synthesis can be performed using devices such as a PE-Applied Biosystems 430A peptide synthesizer (commercially available from Applied Biosystems, Foster City, Calif.).

Longer polypeptides are conveniently obtained by expression cloning. A polynucleotide encoding the desired polypeptide is operably linked to control elements for transcription and translation, and then transfected into a suitable host cell. Expression may be effected in procaryotes such as E. coli (ATCC Accession No. 31446 or 27325), eukaryotic microorganisms such as the yeast Saccharomyces cerevisiae, or higher eukaryotes, such as insect or mammalian cells. A number of expression systems are described in U.S. Pat. No. 5,552,524. Expression cloning is available from such commercial services as Lark Technologies, Houston Tex. The production of protein from 4 exemplary clones of this invention in insect cells is illustrated in Example 6. The protein is purified from the producing host cell by standard methods in protein chemistry, such as affinity chromatography and HPLC. Expression products are optionally produced with a sequence tag to facilitate affinity purification, which can subsequently be removed.

Preferred sequences are 40%, 60%, 80%, 90%, or 100% identical to one of the sequences exemplified in this disclosure; in order if increasing preference. The length of the identical or homologous sequence compared with the native human polynucleotide can be about 7, 10, 15, 20, 30, 50 or 100 residues in order of increasing preference, up to the length of the entire encoding region.

Polypeptides can be tested for an ability to modulate TRRE in a TNF-R cleavage assay. The polypeptide is contacted with the receptor (preferably expressed on the surface of a cell, such as a C75 cell), and the ability of the polypeptide to increase or decrease receptor cleavage and release is determined. Cleavage of TNF-R by exemplary polypeptides of this invention is illustrated in Example 7.

Polypeptides of this invention can be used as immunogens for raising antibody. Large proteins will raise a cocktail of antibodies, while short peptide fragments will raise antibodies against small region of the intact protein. Antibody clones can be mapped for protein binding site by producing short overlapping peptides of about 10 amino acids in length. Overlapping peptides can be prepared on a nylon membrane support by standard F-Moc chemistry, using a SPOTS™ kit from Genosys according to manufacturer's directions.

Polypeptides of this invention can also be used to affect TNF signal transduction, as explained below.

Antibodies

Polyclonal antibodies can be prepared by injecting a vertebrate with a polypeptide of this invention in an immunogenic form. Immunogenicity of a polypeptide can be enhanced by linking to a carrier such as KLH, or combining with an adjuvant, such as Freund's adjuvant. Typically, a priming injection is followed by a booster injection is after about 4 weeks, and antiserum is harvested a week later. Unwanted activity cross-reacting with other antigens, if present, can be removed, for example, by running the preparation over adsorbants made of those antigens attached to a solid phase, and collecting the unbound fraction. If desired, the specific antibody activity can be further purified by a combination of techniques, which may include protein A chromatography, ammonium sulfate precipitation, ion exchange chromatography, HPLC, and immunoaffinity chromatography using the immunizing polypeptide coupled to a solid support. Antibody fragments and other derivatives can be prepared by standard immunochemical methods, such as subjecting the antibody to cleavage with enzymes such as papain or pepsin.

Production of monoclonal antibodies is described in such standard references as Harrow & Lane (1988), U.S. Pat. Nos. 4,491,632, 4,472,500 and 4,444,887, and Methods in Enzymology 73B:3 (1981). Briefly, a mammal is immunized, and antibody-producing cells (usually splenocytes) are harvested. Cells are immortalized by fusion with a non-producing myeloma, transfecting with Epstein Barr Virus, or transforming with oncogenic DNA. The treated cells are cloned and cultured, and the clones are selected that produce antibody of the desired specificity.

Other methods of obtaining specific antibody molecules (optimally in the form of single-chain variable regions) involve contacting a library of immunocompetent cells or viral particles with the target antigen, and growing out positively selected clones. Immunocompetent phage can be constructed to express immunoglobulin variable region segments on their surface. See Marks et al., New Eng. J. Med. 335:730, 1996, International Patent Applications WO 9413804, WO 9201047, WO 90 02809, and McGuiness et al., Nature Biotechnol. 14:1449, 1996.

The antibodies of this invention are can be used in immunoassays for TRRE modulators. General techniques of immunoassay can be found in "The Immunoassay Handbook", Stockton Press NY, 1994; and "Methods of Immunological Analysis", Weinheim: VCH Verlags gesellschaft mbH, 1993). The antibody is combined with a test sample under conditions where the antibody will bind specifically to any modulator that might be present, but not any other proteins liable to be in the sample. The complex formed can be measured in situ (U.S. Pat. Nos. 4,208,479 and 4,708,929), or by physically separating it from unreacted reagents (U.S. Pat. No. 3,646,346). Separation assays typically involve labeled TRRE reagent (competition assay), or labeled antibody (sandwich assay) to facilitate detection and quantitation of the complex. Suitable labels are radio-isotopes such as $^{125}I$, enzymes such as β-galactosidase, and fluorescent labels such as fluorescein. Antibodies of this invention can also be used to detect TRRE modulators in fixed tissue sections by immunohistology. The antibody is contacted with the tissue, unreacted antibody is washed away, and then bound antibody is detected—typically using a labeled anti-immunoglobulin reagent. Immunohistology will show not only whether the modulator is present, but where it is located in the tissue.

Detection of TRRE modulators is of interest for research purposes, and for clinical use. As indicated earlier, high expression of TRRE modulators may correlate with progression of cancer. Diagnostic tests are also of use in monitoring TRRE modulators that are administered in the course of therapy.

Antibodies of this invention can also be used for preparation of medicaments. Antibodies with therapeutic potential include those that affect TRRE activity—either by promoting clearance of a TRRE modulator, or by blocking its physiological action. Antibodies can be screened for desirable activity according to assays described in the next section.

Screening Assays

This invention provides a number of screening methods for selecting and developing products that modulate TRRE, and thus affect TNF signal transduction.

One screening method is for polynucleotides that have an ability to modulate TRRE activity. To do this screening, cells are obtained that express both TRRE and the TNF receptor. Suitable cell lines can be constructed from any cell that expresses a level of functional TRRE activity. These cells are identifiable by testing culture supernatant for an ability to release membrane-bound TNF-R. The level of TRRE expression should be moderate, so that an increase in activity can be detected. The cells can then be genetically altered to express either p55 or p75 TNF-R, illustrated in Example 1. Exemplary is the C75R line: COS-1 cells genetically altered to express the 75 kDa form of the TNF-R. Release of TNF-R from the cell can be measured either by testing residual binding of labeled TNF ligand to the cell, or by immunoassay of the supernatant for released receptor (Example 1).

The screening assay is conducted by contacting the cells expressing TRRE and TNF-R with the polynucleotides to be screened. The effect of the polynucleotide on the enzymatic release of TNF-R from the cell is determined, and polynucleotides with desirable activity (either promoting or inhibiting TRRE activity) are selected. In a variation of this method, cells expressing TRRE activity but not TNF-R (such as untransfected COS-1 cells) are contacted with the test polynucleotide. Then the culture medium is collected, and used to assay for TRRE activity using a second cell expressing TNF-R (such as C75 cells).

This type of screening assay is useful for the selection of polynucleotides from an expression library believed to contain encoding sequences for TRRE modulators. The Jurkat cell expression library (ATCC Accession No. TIB-152) is exemplary. Other cells from which suitable libraries can be constructed are those known to express high levels of TRRE, especially after PMA stimulation, such as THP-1, U-937, HL-60, ME-180, MRC-5, Raji, K-562, and normal human monocytes. The screening involves expressing DNA from the library in the selected cell line being used for screening. Wells with the desired activity are selected, and the DNA is recovered, optionally after replication or cloning of the cells. Repeat cycles of functional screening and selection can lead to identification of new polynucleotide clones that promote or inhibit TRRE activity. This is illustrated below in Example 5. Further experiments can be performed on the selected polynucleotides to determine it modulates TRRE activity inside the cell, or through the action of a protein product. A long open reading frame suggests a role for a protein product, and examination of the amino acid sequence for a signal peptide and a membrane spanning region can help determine whether the protein is secreted from the cell or expressed in the surface membrane.

This type of screening is also useful for further development of the polynucleotides of this invention. For example, expression constructs can be developed that encode functional peptide fragments, fusion proteins, and other variants. The minimum size of polynucleotide sequence that still encodes TRRE modulation activity can be determined by removing part of the sequence and then using the screening assay to determine whether the activity is still present. Mutated and extended sequences can be tested in the same way.

This type of screening assay is also useful for developing compounds that affect TRRE activity by interfering with mRNA that encode a TRRE modulator. Of particular interest are ribozymes and antisense oligonucleotides. Ribozymes are endoribonucleases that catalyze cleavage of RNA at a specific site. They comprise a polynucleotide sequence that is complementary to the cleavage site on the target, and additional sequence that provide the tertiary structure to effect the cleavage. Construction of ribozymes is described in U.S. Pat. Nos. 4,987,071 and 5,591,610. Antisense oligonucleotides that bind mRNA comprise a short sequence complementary to the mRNA (typically 8–25 bases in length). Preferred chemistry for constructing antisense oligonucleotides is outlined in an earlier section. Specificity is provided both by the complementary sequence, and by features of the chemical structure. Antisense molecules that inhibit expression of cell surface receptors are described in U.S. Pat. Nos. 5,135,917 and 5,789,573. Screening involves contacting the cell expressing TRRE activity and TNF-R with the compound and determining the effect on receptor release. Ribozymes and antisense molecules effective in altering expression of a TRRE promoter would decrease TNF-R release. Ribozymes and antisense molecules effective in altering expression of a TRRE inhibitor would increase TNF-R release.

Another screening method described in this disclosure is for testing the ability of polypeptides to modulate TRRE activity (Example 7). Cells expressing both TNF-R and a moderate level of TRRE activity are contacted with the test polypeptides, and the rate of receptor release is compared with the rate of spontaneous release. An increased rate of release indicates that the polypeptide is a TRRE promoter, while a decreased rate indicates that the polypeptide is a TRRE inhibitor. This assay can be used to test the activity of new polypeptides, and develop variants of polypeptides already known to modulate TRRE. The minimum size of polypeptide sequence that still encodes TRRE modulation activity can be determined by making a smaller fragment of the polypeptide and then using the screening assay to determine whether the activity is still present. Mutated and extended sequences can be tested in the same way.

Another screening method embodied in this invention is a method for screening substances that interfere with the action of a TRRE modulator at the protein level. The method involves incubating cells expressing TNF receptor (such as C75R cells) with a polypeptide of this invention having TNF promoting activity. There are two options for supplying the TRRE modulator in this assay. In one option, the polypeptide is added to the medium of the cells as a reagent, along with the substance to be tested. In another option, the cells are genetically altered to express the TRRE modulator at a high level, and the assay requires only that the test substance be contacted with the cells. This option allows for high throughput screening of a number of test compounds.

Either way, the rate of receptor release is compared in the presence and absence of the test substance, to identify compounds that enhance or diminish TRRE activity. Parallel experiments should be conducted in which the activity of the substance on receptor shedding is tested in the absence of added polypeptide (using cells that don't express the polypeptide). This will determine whether the activity of the test substance occurs via an effect on the TRRE promoter being added, or through some other mechanism.

This type of screening assay is useful for identifying antibodies that affect the activity of a TRRE modulator. Antibodies are raised against a TRRE modulator as described in the previous section. If the antibody decreases TRRE activity in the screening assay, then it has therapeutic potential to lower TRRE activity in vivo. Screening of monoclonal antibodies using this assay can also help identify binding or catalytic sites in the polypeptide.

This type of screening assay is also useful for high throughput screening of small molecule compounds that have the ability to affect the level of TNF receptors on a cell, by way of its influence on a TRRE modulator. Small molecule compounds that have the desired activity are often preferred for pharmaceutical compositions, because they are often more stable and less expensive to produce.

Medicaments and Their Use

As described earlier, a utility of certain products embodied in this invention is to affect signal transduction from cytokines (particularly TNF). Products that promote TRRE activity have the effect of decreasing TNF receptors on the surface of cells, which would decrease signal transduction from TNF. Conversely, products that inhibit TRRE activity prevent cleavage of TNF receptors, increasing signal transduction.

The ability to affect TNF signal transduction is of considerable interest in the management of clinical conditions in which TNF signaling contributes to the pathology of the condition. Such conditions include:

Heart failure. IL-1β and TNF are believed to be central mediators for perpetuating the inflammatory process, recruiting and activating inflammatory cells. The inflammation depress cardiac function in congestive heart failure, transplant rejection, myocarditis, sepsis, and burn shock.

Cachexia. The general weight loss and wasting occurring in the course of chronic diseases, such as cancer. TNF is believed to affect appetite, energy expenditure, and metabolic rate.

Crohn's disease. The inflammatory process mediated by TNF leads to thickening of the intestinal wall, ensuing from lymphedema and lymphocytic infiltration.

Endotoxic shock. The shock induced by release of endotoxins from gram-negative bacteria, such as *E. coli*, involves TNF-mediated inflammation.

Arthritis. TNF promotes expression of nitric oxide synthetase, believed to be involved in disease pathogenesis.

Other conditions of interest are multiple sclerosis, sepsis, inflammation brought on by microbe infection, and diseases that have an autoimmune etiology, such as Type I Diabetes.

Polypeptides of this invention that promote TRRE activity can be administered with the objective of decreasing or normalizing TNF signal transduction. For example, in congestive heart failure or Crohn's disease, the polypeptide is given at regular intervals to lessen the inflammatory sequelae. The treatment is optionally in combination with other agents that affect TNF signal transduction (such as antibodies to TNF or receptor antagonists) or that lessen the extent of inflammation in other ways.

Polynucleotides of this invention can also be used to promote TRRE activity by gene therapy. The encoding sequence is operably linked to control elements for transcription and translation in human cells. It is then provided in a form that will promote entry and expression of the encoding sequence in cells at the disease site. Forms suitable for local injection include naked DNA, polynucleotides packaged with cationic lipids, and polynucleotides in the form of viral vectors (such as adenovirus and AAV constructs). Methods of gene therapy known to the practitioner skilled in the art will include those outlined in U.S. Pat. Nos. 5,399,346, 5,827,703, and 5,866,696.

The ability to affect TNF signal transduction is also of interest where TNF is thought to play a beneficial role in resolving the disease. In particular, TNF plays a beneficial role in the necrotizing of solid tumors. Accordingly, products of this invention can be administered to cancer patients to inhibit TRRE activity, thereby increasing TNF signal transduction and improve the beneficial effect.

Embodiments of the invention that inhibit TRRE activity include antisense polynucleotides. A method of conferring long-standing inhibitory activity is to administer antisense gene therapy. A genetic construct is designed that will express RNA inside the cell which in turn will decrease the transcription of the target gene (U.S. Pat. No. 5,759,829). In humans, a more frequent form of antisense therapy is to administer the effector antisense molecule directly, in the form of a short stable polynucleotide fragment that is complementary to a segment of the target mRNA (U.S. Pat. Nos. 5,135,917 and 5,789,573)—in this case, the transcript that encodes the TRRE modulator. Another embodiment of the invention that inhibits TRRE are ribozymes, constructed as described in an earlier section. The function of ribozymes in inhibiting mRNA translation is described in U.S. Pat. Nos. 4,987,071 and 5,591,610.

Once a product of this invention is found to have suitable TRRE modulation activity in the in vitro assays described in this disclosure, it is preferable to also test its effectiveness in an animal model of a TNF mediated disease process. Example 3 describes an LPS model for sepsis that can be used to test promoters of TRRE activity. Example 4 describes a tumor necrosis model, in which TRRE inhibitors could be tested for an ability to enhance necrotizing activity. Those skilled in the art will know of other animal models suitable for testing effects on TNF signal transduction or inflammation. Other illustrations are the cardiac ischemia reperfusion models of Weyrich et al. (*J. Clin. Invest.* 91:2620, 1993) and Garcia-Criado et al. (*J. Am. Coll. Surg.* 181:327, 1995); the pulmonary ischemia reperfusion model of Steinberg et al. (*J. Heart Lung Transplant.* 13:306, 1994), the lung inflammation model of International Patent Application WO 9635418; the bacterial peritonitis model of Sharar et al. (*J. Immunol.* 151:4982, 1993), the colitis model of Meenan et al. (*Scand. J. Gastroenterol.* 31:786, 1996), and the diabetes model of von Herrath et al. (*J. Clin. Invest.* 98:1324, 1996). Models for septic shock are described in Mack et al. *J. Surg. Res.* 69:399, 1997; and Seljelid et al. *Scand. J. Immunol.* 45:683–7.

For use as an active ingredient in a pharmaceutical preparation, a polypeptide, polynucleotide, or antibody of this invention is generally purified away from other reactive or potentially immunogenic components present in the mixture in which they are prepared. Typically, each active ingredient is provided in at least about 90% homogeneity, and more preferably 95% or 99% homogeneity, as determined by functional assay, chromatography, or SDS polyacrylamide gel electrophoresis. The active ingredient is then compounded into a medicament in accordance with generally accepted procedures for the preparation of pharmaceutical preparations, such as described in *Remington's Pharmaceutical Sciences* 18*th Edition* (1990), E. W. Martin ed., Mack Publishing Co., PA. Steps in the compounding of the medicament depend in part on the intended use and mode of administration, and may include sterilizing, mixing with appropriate non-toxic and non-interfering excipients and carriers, dividing into dose units, and enclosing in a delivery device. The medicament will typically be packaged with information about its intended use.

Mode of administration will depend on the nature of the condition being treated. For conditions that are expected to require moderate dosing and that are at well perfused sites (such as cardiac failure), systemic administration is acceptable. For example, the medicament may be formulated for intravenous administration, intramuscular injection, or absorption sublingually or intranasally. Where it is possible to administer the active ingredient locally, this is usually preferred. Local administration will both enhance the concentration of the active ingredient at the disease site, and minimize effects on TNF receptors on other tissues not involved in the disease process. Conditions that lend themselves to administration directly at the disease site include cancer and rheumatoid arthritis. Solid tumors can be injected directly when close to the skin, or when they can be reached by an endoscopic procedure. Active ingredients can also be administered to a tumor site during surgical resection, being implanted in a gelatinous matrix or in a suitable membrane such as Gliadel® (Guilford Sciences). Where direct administration is not possible, the administration may be given through an arteriole leading to the disease site. Alternatively, the pharmaceutical composition may be formulated to enhance accumulation of the active ingredient at the disease site. For example, the active ingredient can be encapsulated in a liposome or other matrix structure that displays an antibody or ligand capable of binding a cell surface protein on the target cell. Suitable targeting agents include antibodies against cancer antigens, ligands for tissue-specific receptors (e.g., serotonin for pulmonary targeting). For compositions that decrease TNF signal transduction, an appropriate targeting molecule may be the TNF ligand, since the target tissue may likely display an unusually high density of the TNF receptor.

Effective amounts of the compositions of the present invention are those that alter TRRE activity by at least about 10%, typically by at least about 25%, more preferably by about 50% or 75%. Where near complete ablation of TRRE activity is desirable, preferred compositions decrease TRRE activity by at least 90%. Where increase of TRRE activity is desirable, preferred compositions increase TRRE activity by at least 2-fold. A minimum effective amount of the active compound will depend on the disease being treated, which of the TRRE modulators is selected for use, and whether the administration will be systemic or local. For systemic administration, an effective amount of activity will generally be an amount of the TRRE modulator that can cause a change in the enzyme activity by 100 to 50,000 Units—typically about 10,000 Units. The mass amount of protein, nucleic acid, or antibody is chosen accordingly, based on the specific activity of the active compound in Units per gram.

The following examples provided as a further guide to the practitioner, and are not intended to limit the invention in any way.

EXAMPLES

Example 1

Assay System for TRRE Activity

This Example illustrates an assay system that measures TRRE activity on the human TNF-R in its native conformation in the cell surface membrane Membrane-associated TNF-R was chosen as the substrate, as having microenvironment similar to that of the substrate for TRRE in vivo. Membrane-associated TNF-R also requires more specific activity, which would differentiate less-specific proteases. Cells expressing an elevated level of the p75 form of TNF-R were constructed by cDNA transfection into monkey COS-1 cells which express little TNF-R of either the 75 kDa or 55 kDa size.

The procedure for constructing these cells was as follows: cDNA of human p75 TNF-R was cloned from a λgt10 cDNA library derived from human monocytic U-937 cells (Clontech Laboratories, Palo Alto, Calif.). The first 300 bp on both 5' and 3' ends of the cloned fragment was sequenced and compared to the reported cDNA sequence of human p75 TNF-R. The cloned sequence was a 2.3 kb fragment covering positions 58–2380 of the reported p75 TNF-R sequence, which encompasses the full length of the p75 TNF-R-coding sequence from positions 90–1475. The 2.3 kb p75 TNF-R cDNA was then subcloned into the multiple cloning site of the pCDNA3 eukaryotic expression vector. The orientation of the p75 TNF-R cDNA was verified by restriction endonuclease mapping.

Figure 1:
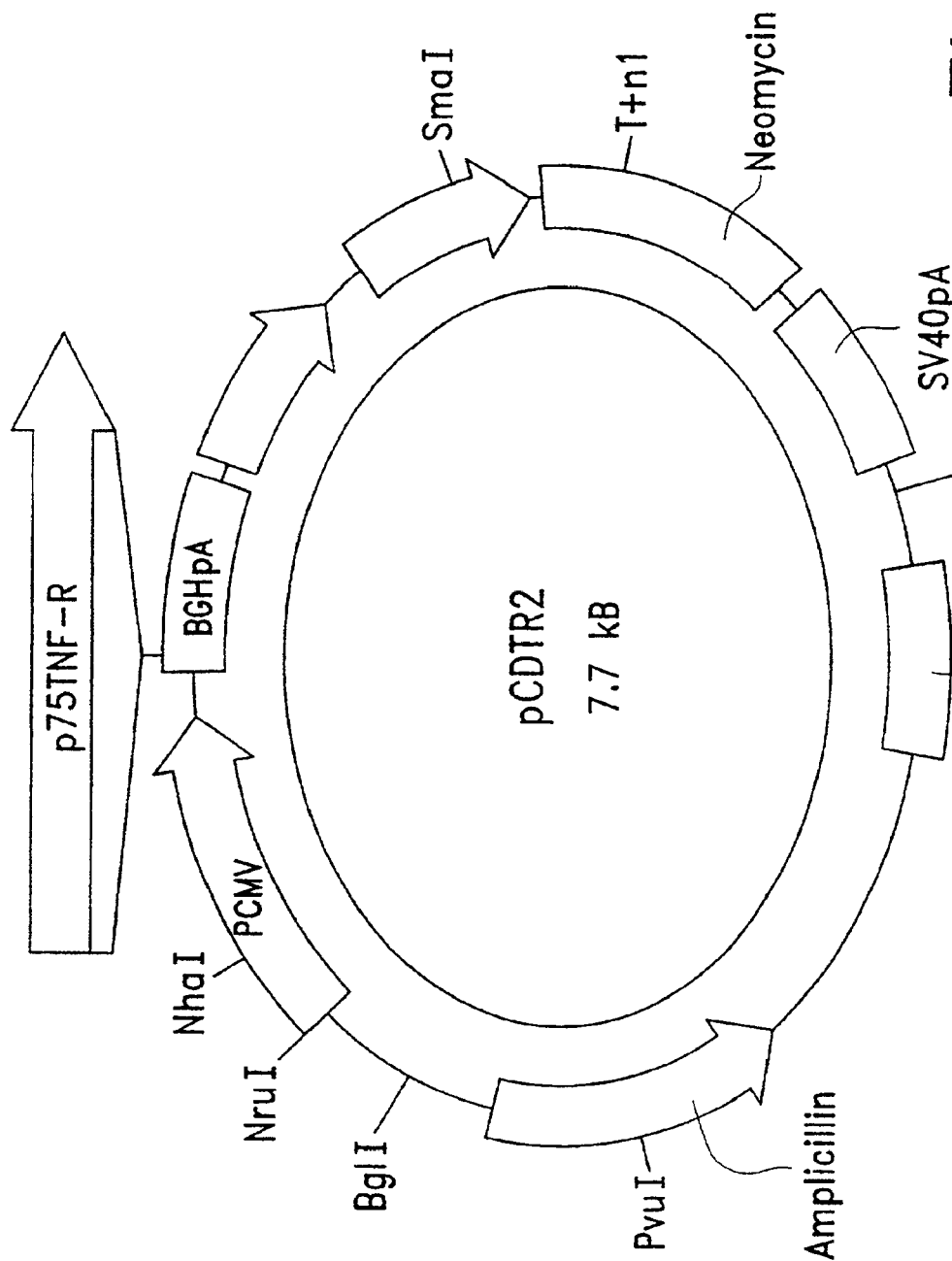
FIG. 1 is a schematic representation of plasmid pCDTR2. This plasmid expresses p75 TNF-R, the ~75 kDa form of the TNF receptor. PCMV stands for cytomegalovirus; BGHpA stands for bovine growth hormone polyadenylation signal.

FIG. 1 illustrates the final 7.7 kb construct, pCDTR2. It carries the neomycin-resistance gene for the selection of transfected cells in G418, and the expression of the p75 TNF-R is driven by the cytomegalovirus promoter. The pCDTR2 was then transfected into monkey kidney COS-1 cells (ATCC CRL-1650) using the calcium phosphate-DNA precipitation method. The selected clone in G418 medium was identified and subcultured. This clone was given the designation C75R.

To determine the level of p75 TNF-R expression on C75R cells, $2 \times 10^5$ cells/well were plated into a 24-well culture plate and incubated for 12 to 16 hours in 5% $CO_2$ at 37° C. They were then incubated with 2–30 ng $^{125}I$ human recombinant TNF (radiolabeled using the chloramine T method) in the presence or absence of 100-fold excess of unlabeled human TNF at 4° C. for 2 h. After three washes with ice-cold PBS, cells were lysed with 0.1N NaOH and bound radioactivity was determined in a Pharmacia Clinigamma counter (Uppsala, Sweden).

Figure 2:
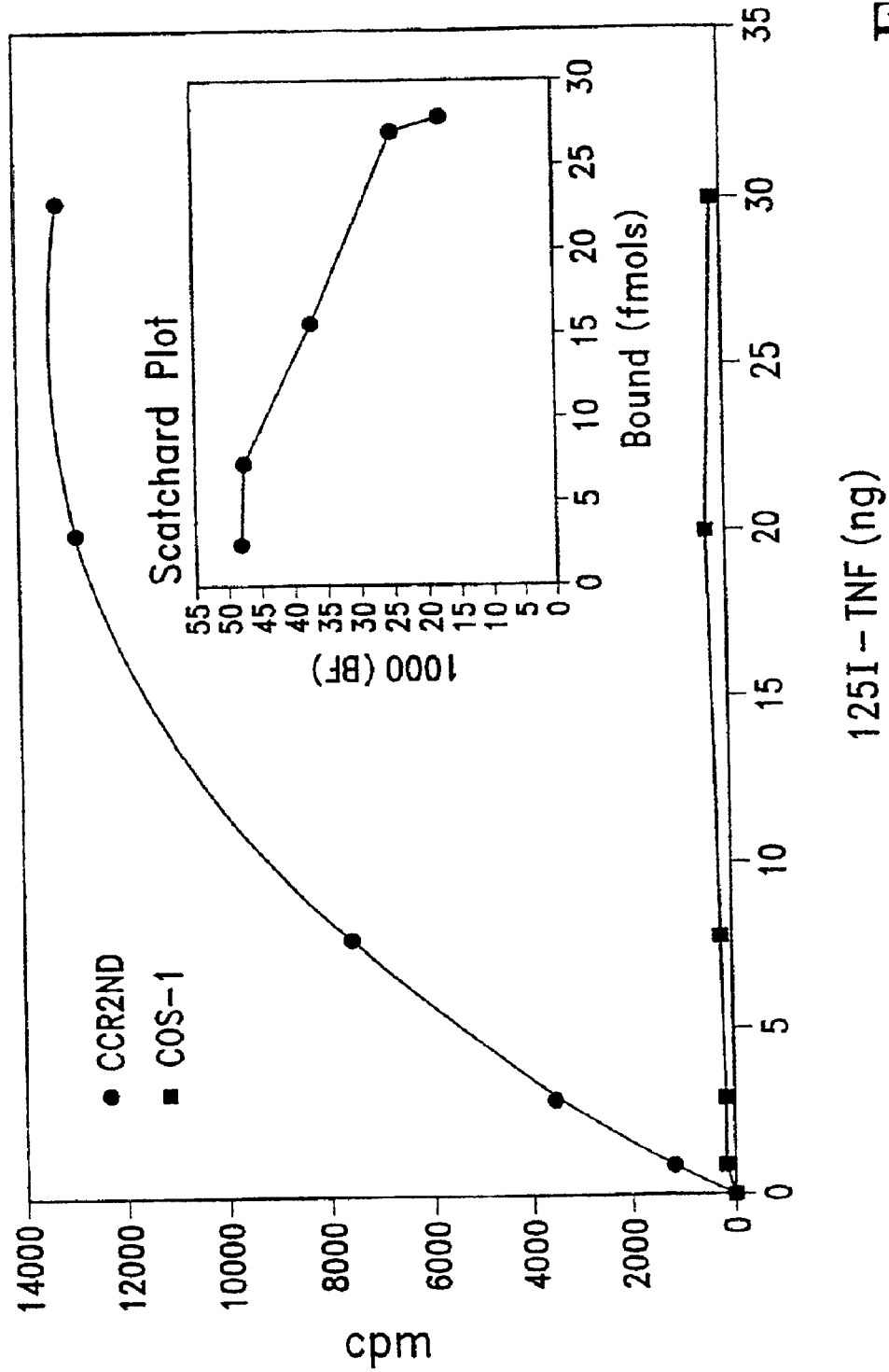
FIG. 2 is a line depicting the levels of p75 TNF-R detected on COS-1 cells genetically altered to express the receptor.

FIG. 2 shows the results obtained. C75R had a very high level of specific binding of radiolabeled $^{125}I$-TNF, while parental COS-1 cells did not. The number of TNF-R expressed on C75R was determined to be 60,000–70,000 receptors per cell by Scatchard analysis (FIG. 2, inset). The Kd value calculated was $5.6 \times 10^{-10}$ M. This Kd value was in close agreement to the values previously reported for native p75 TNF-R.

TRRE was obtained by PHA stimulation of THP-1 cells (WO 9802140). THP-1 cells (ATCC 45503) growing in logarithmic phase were collected and resuspended to $1 \times 10^6$ cells/ml of RPMI-1640 supplemented with 1% FCS and incubated with $10^{-6}$ M PMA for 30 min in 5% $CO_2$ at 37° C. The cells were collected and washed once with serum-free medium to remove PMA and resuspended in the same volume of RPMI-1640 with 1% FCS. After 2 hours incubation in 5% $CO_2$ at 37° C., the cell suspension was collected, centrifuged, and the cell-free supernatant was collected as the source of TRRE.

In order to measure the effect of TRRE on membrane-bound TNF-R in the COS-1 cell constructs, the following experiment was performed. C75R cells were seeded at a density of $2 \times 10^5$ cells/well in a 24-well cell culture plate and incubated for 12 to 16 hours at 37° C. in 5% $CO_2$. The medium in the wells was aspirated, replaced with fresh medium alone or with TRRE medium, and incubated for 30 min at 37° C., The medium was then replaced with fresh medium containing 30 ng/ml $^{125}I$-labeled TNF. After 2 hours at 4° C., the cells were lysed with 0.1 N NaOH and the level of bound radioactivity was measured. The level of specific binding of C75R by $^{125}I$-TNF was significantly decreased after incubation with TRRE. The radioactive count was 1,393 cpm on the cells incubated with TRRE compared to 10,567 cpm on the cells not treated with TRRE, a loss of 87% of binding capacity.

In order to determine the size of the p75 TNF-R cleared from C75R by TRRE, the following experiment was performed. $15 \times 10^6$ C75R cells were seeded in a 150 mm cell culture plate and incubated at 37° C. in 5% $CO_2$ for 12 to 16 hours. TRRE medium was incubated with C75R cells in the 150 mm plate for 30 min and the resulting supernatant was collected and centrifuged. The concentrated sample was applied to 10% acrylamide SDS-PAGE and electrophoretically transferred to a polyvinylidene difluoride membrane (Immobilon). Immunostaining resulted in a single band of 40 kDa, similar to the size found in biological fluids. Thus, transfected COS-1 cells expressed high levels of human p75 TNF-R in a form similar to native TNF-R.

The following assay method was adopted for routine measurement of TRRE activity. C75R cells and COS-1 cells were seeded into 24-well culture plates at a density of $2.5 \times 10^5$ cells/ml/well and incubated overnight (for 12 to 16 hours) in 5% $CO_2$ at 37° C. After aspirating the medium in the well, 300 µl of TRRE medium was incubated in each well of both the C75R and COS-1 plates for 30 min in 5% $CO_2$ at 37° C. (corresponding to A and C mentioned below, respectively). Simultaneously, C75R cells in 24-well plates were also incubated with 300 µl of fresh medium or buffer. The supernatants were collected, centrifuged, and then assayed for the concentration of soluble p75 TNF-R by ELISA.

ELISA assay for released TNF-R (WO 9802140) was performed as follows: Polyclonal antibodies to human p75 TNF-R were generated by immunization of New Zealand white female rabbits (Yamamoto et al. *Cell. Immunol.* 38:403–416, 1978). The IgG fraction of the immunized rabbit serum was purified using a protein G (Pharmacia Fine Chemicals, Uppsala, Sweden) affinity column (Ey et al. (1978) *Immunochemistry* 15:429–436, 1978). The IgG fraction was then labeled with horseradish peroxidase (Sigma Chemical Co., St. Louis, Mo.) (Tijssen and Kurstok, *Anal. Biochem.* 136:451–457, 1984). In the first step of the assay, 5 µg of unlabeled IgG in 100 µl of 0.05 M carbonate buffer (pH 9.6) was bound to a 96-well ELISA microplate (Corning, Corning, N.Y.) by overnight incubation at 4° C. Individual wells were washed three times with 300 µl of 0.2% Tween-20 in phosphate buffered saline (PBS). The 100 µl of samples and recombinant receptor standards were added to each well and incubated at 37° C. for 1 to 2 hours. The wells were then washed in the same manner, 100 µl of horseradish peroxidase-labeled IgG added and incubated for 1 hour at 37° C. The wells were washed once more and the color was developed for 20 minutes (min) at room temperature with the substrates ABTS (Pierce, Rockford, Ill.) and 30% $H_2O_2$ (Fisher Scientific, Fair Lawn, N.J.). Color development was measured at 405 nm.

When C75R cells were incubated with TRRE medium, soluble p75 TNF-R was released into the supernatant which was measurable by ELISA. The amount of receptors released corresponded to the amount of TRRE added. There was also a level of spontaneous TNF-R release in C75R cells incubated with just medium alone. It is hypothesized that this is due to an endogenous source of proteolytic enzyme, a homolog of the human TRRE of monkey origin.

The following calculations were performed. A=(amount of soluble p75 TNF-R in a C75R plate treated with the TRRE containing sample); i.e. the total amount of sTNF-R in a C75R plate. B=(amount of soluble p75 TNF-R spontaneously released in a C75R plate treated with only medium or buffer containing the same reagent as the corresponding samples but without exogenous TRRE); i.e. the spontaneous release of sTNF-R from C75R cells. C =(amount of soluble p75 TNF-R in a COS-1 plate treated with the TRRE sample or the background level of soluble p75 TNF-R released by THP-1.); i.e. the degraded value of transferred (pre-existing) sTNF-R in the TRRE sample during 30 min incubation in a COS-1 plate. This corresponds to the background level of sTNF-R degraded in a C75R plate. The net release of soluble p75 TNF-R produced only by TRRE activity existing in the initial sample is calculated as follows: (Net release of soluble p75 TNF-R only by TRRE)=A–B–C.

Unit activity of TRRE was defined as follows: 1 pg of soluble p75 TNF-R net release (A–B–C) in the course of the assay is one unit (U) of TRRE activity.

Using this assay, the time course of receptor shedding by TRRE was measured in the following experiment. TRRE-medium was incubated with C75R and COS-1 cells for varying lengths of time. The supernatants were then collected and assayed for the level of soluble p75 TNF-R by ELISA and the net TRRE activity was calculated. Detectable levels of soluble receptor were released by TRRE within 5 min and increased up to 30 min. Longer incubation times showed that the level of TRRE remained relatively constant after 30 min, presumably from the depletion of substrates. Therefore, 30 min was determined to be the optimal incubation time.

The induction patterns of TRRE and known MMPs by PMA stimulation are quite different. In order to induce MMPs, monocytic U-937 cells, fibrosarcoma HT-1080 cells, or peritoneal exudate macrophages (PEM) usually have to be stimulated for one to three days with LPS or PMA. On the other hand, as compared with this prolonged induction, TRRE is released very quickly in culture supernatant following 30 min of PMA-stimulation. The hypothesis that TRRE and sTNF-R form a complex in vitro was confirmed by the experiment that 25% TRRE activity was recovered from soluble p75 TNF-R affinity column. This means that free TRRE has the ability to bind to its catalytic product, sTNF-R. The remaining 75% which did not combine to the affinity column may already be bound to sTNF-R or may not have enough affinity to bind to sTNF-R even though it is in a free form.

Example 2

Characterization of TRRE Obtained from THP-1 Cells

TRRE obtained by PHA stimulation of THP-1 cells was partially purified from the culture medium (WO 9802140). First, protein from the medium was concentrated by 100% saturated ammonium sulfate precipitation at 4° C. The precipitate was pelleted by centrifugation at 10,000×g for 30 min and resuspended in PBS in approximately twice the volume of the pellet. This solution was then dialyzed at 4° C. against 10 mM Tris-HCl, 60 mM NaCl, pH 7.0. This sample was loaded on an anion-exchange chromatography, Diethylaminoethyl (DEAE)-Sephadex A-25 column (Pharmacia Biotech) (2.5×10 cm) previously equilibrated with 50 mM Tris-HCl, 60 mM NaCl, pH 8.0. TRRE was then eluted with an ionic strength linear gradient of 60 to 250 mM NaCl, 50 mM Tris-HCl, pH 8.0. Each fraction was measured for absorbance at 280 nm and assayed for TRRE activity. The DEAE fraction with the highest specific activity (the highest value of TRRE units/A280) was pooled and used in the characterizations of TRRE described in this example.

In the next experiment, the substrate specificity of the enzyme was elucidated using immunohistochemical techniques. Fluorescein isothiocyanate (FITC)-conjugated anti-CD54, FITC-conjugated goat anti-rabbit and mouse antibodies, mouse monoclonal anti-CD30, anti-CD11b and anti-IL-1R (Serotec, Washington D.C.) were used. Rabbit polyclonal anti-p55 and p75 TNF-R were obtained according to Yamamoto et al. (1978) *Cell Immunol.* 38:403–416. THP-1 cells were treated for 30 min with 1,000 and/or 5,000 U/ml of TRRE eluted from the DEAE-Sephadex column, and then transferred to 12×75 mm polystyrene tubes (Fischer Scientific, Pittsburgh, Pa.) at 1×10$^5$ cells/100 µl/tube. The cells were then pelleted by centrifugation at 350×g for 5 min at 4° C. and stained directly with 10 µl FITC-conjugated anti-CD54 (diluted in cold PBS/0.5% sodium aside), indirectly with FITC-conjugated anti-mouse antibody after treatment of mouse monoclonal anti-CD11b, IL-1R and CD30 and also indirectly with FITC-conjugated anti-rabbit antibody after treatment of rabbit polyclonal anti-p55 and p75 TNF-R.

THP-1 cells stained with each of the antibodies without treatment of TRRE were used as negative controls. The tubes were incubated for 45 min at 4° C., agitated every 15 min, washed twice with PBS/2% FCS, repelleted and then resuspended in 200 µl of 1% paraformaldehyde. These labeled THP-1 cells were analyzed using a fluorescence activated cell sorter (FACS) (Becton-Dickinson, San Jose, Calif.) with a 15 mW argon laser with an excitation of 488 nm. Fluorescent signals were gated on the basis of forward and right angle light scattering to eliminate dead cells and aggregates from analysis. Gated signals (10$^4$) were detected at 585 BP filter and analyzed using Lysis II software. Values were expressed as percentage of positive cells, which was calculated by dividing mean channel fluorescence intensity (MFI) of stained THP-1 cells treated with TRRE by the MFI of the cells without TRRE treatment (negative control cells).

To test the in vitro TNF cytolytic assay by TRRE treatment the L929 cytolytic assay was performed according to the method described by Gatanaga et al. (1990b). Briefly, L929 cells, an adherent murine fibroblast cell line, were plated (70,000 cells/0.1 ml/well in a 96-well plate) overnight. Monolayered L929 cells were pretreated for 30 min with 100, 500 or 2,500 U/ml of partially-purified TRRE and then exposed to serial dilutions of recombinant human TNF for 1 hour. After washing the plate with RPMI-1640 with 10% FCS to remove the TRRE and TNF, the cells were incubated for 18 hours in RPMI-1640 with 10% FCS containing 1 µg/ml actinomycin D at 37° C. in 5% CO$_2$. Culture supernatants were then aspirated and 50 µl of 1% crystal violet solution was added to each well. The plates were incubated for 15 min at room temperature. After the plates were washed with tap water and air-dried, the cells stained with crystal violet were lysed by 100 µl per well of 100 mM HCl in methanol. The absorbance at 550 nm was measured using an EAR 400 AT plate reader (SLT-Labinstruments, Salzburg, Austria).

To investigate whether TRRE also truncates the ~55 kDa size of TNF-R, partially-purified TRRE was applied to THP-1 cells which express low levels of both p55 and p75 TNF-R (approximately 1,500 receptors/cell by Scatchard analysis). TRRE eluate from the DEAE-Sephadex column was added to THP-1 cells (5×10$^6$ cells/ml) at a final TRRE concentration of 1,000 U/ml for 30 min. The concentration of soluble p55 and p75 TNF-R in that supernatant was measured by soluble p55 and p75 TNF-R ELISA. TRRE was found to truncate both human p55 and p75 TNF-R on THP-1 cells and released 2,382 and 1,662 pg/ml soluble p55 and p75 TNF-R, respectively.

Therefore, TRRE obtained by PHA stimulation of THP-1 cells is capable of enzymatically cleaving and releasing human p75 TNF-R on C75R cells, and both human p55 and p75 TNF-R on THP-1 cells.

Partial inhibition of TRRE activity was obtained by chelating agents such as 1,10-phenanthroline, EDTA and EGTA (% TRRE activity remaining were 41%, 67% and 73%, respectively, at 2 mM concentration). On the other hand, serine protease inhibitors such as PMSF, AEBSF and 3,4-DCI, and serine and cysteine protease inhibitors such as TLCK and TPCK had no effect on the inhibition of TRRE. TRRE was slightly activated in the presence of $Mn^{2+}$, $Ca^{2+}$, $Mg^{2+}$, and $Co^{2+}$ (% TRRE activities remaining were 157%, 151%, 127%, and 123%, respectively), whereas partial inhibition occurred in the presence of $Zn^{2+}$ and $Cu^{2+}$ (% TRRE activities remaining were 23% and 47%, respectively) (WO 9802140).

TRRE fractions from the most active DEAE fraction (60 mM to 250 mM NaCl) can be purified further. In one method (WO 9802140), the fractions were concentrated to 500 µL with a Centriprep-10 filter (10,000 MW cut-off membrane) (Amicon). This concentrated sample was applied to 6% PAGE under non-denaturing native conditions. The gel was sliced horizontally into 5 mm strips and each was eluted into 1 ml PBS. The eluates were then tested according to the assay (Example 1) for TRRE activity, Example 3

TRRE Activity Alleviates Septic Shock

The following protocol was used to test the effects of TRRE in preventing mortality in a model for septic shock. Mice were injected with lethal or sublethal levels of LPS, and then with a control buffer or TRRE. Samples of peripheral blood were then collected at intervals to establish if TRRE blocked TNF-induced production of other cytokines in the bloodstream. Animals were assessed for the ability of TRRE to block the clinical effects of shock, and then euthanized and tissues examined by histopathological methods.

Details were as follows: adult Balb/c mice, were placed in a restraining device and injected intravenously via the tail vein with a 0.1 ml solution containing 10 ng to 10 mg of LPS in phosphate buffer saline (PBS). These levels of LPS induce mild to lethal levels of shock in this strain of mice. Shock results from changes in vascular permeability, fluid loss, and dehydration, and is often accompanied by symptoms including lethargy, a hunched, stationary position, rumpled fur, cessation of eating, cyanosis, and, in serious cases, death within 12 to 24 hours. Control mice received an injection of PBS. Different amounts (2,000 or 4,000 U) of purified human TRRE were injected IV in a 0.1 ml volume within an hour prior to or after LPS injection. Serum (0.1 ml) was collected with a 27 gauge needle and 1 ml syringe IV from the tail vein at 30, 60 and 90 minutes after LPS injection. This serum was heparinized and stored frozen at −20° C. Samples from multiple experiments were tested by ELISA for the presence of sTNF-R, TNF, IL-8 and IL-6. Animals were monitored over the next 12 hours for the clinical effects of shock. Selected animals were euthanized at periods from 3 to 12 hours after treatment, autopsied and various organs and tissues fixed in formalin, imbedded in paraffin, sectioned and stained by hematoxalin-eosin (H and E). Tissue sections were subjected to histopathologic and immunopathologic examination.

FIG. 3 shows the results obtained. (♦) LPS alone; (■) LPS plus control buffer; ( ) LPS plus TRRE (2,000 U); (▲) LPS plus TRRE (4,000 U).

Mice injected with LPS alone or LPS and a control buffer died shortly after injection. 50% of the test animals were dead after 8 hours (LPS) or 9 hours (LPS plus control buffer), and 100% of the animals were dead at 15 hours. In contrast, animals treated with TRRE obtained as described in Example 1 did much better. When injections of LPS were accompanied by injections of a 2,000 U of TRRE, death was delayed and death rates were lower. Only 40% of the animals were dead at 24 hours. When 4,000 U of TRRE was injected along with LPS, all of the animals had survived at 24 hours. Thus, TRRE is able to counteract the mortality induced by LPS in test animals.

Example 4

TRRE Activity Decreases Tumor Necrotizing Activity

The following protocol was followed to test the effects of TRRE on tumor necrosis in test animals in which tumors were produced, and in which TNF was subsequently injected.

On Day 0, cutaneous Meth A tumors were produced on the abdominal wall of fifteen BALB/c mice by intradermal injection of $2\times20^5$ Meth A tumor cells. On Day 7, the mice were divided into three groups of five mice each and treated as follows:

Group 1: Injected intravenously with TNF (1 µg/mouse).
Group 2: Injected intravenously with TNF (1 µg/mouse) and injected intratumorally with TRRE obtained as in Example 1 (400 units/mouse, 6, 12 hours after TNF injection).
Group 3: Injected intravenously with TNF (1 µg/mouse) and injected intratumorally with control medium (6, 12 hours after TNF injection).

On Day 8, tumor necrosis was measured with the following results: Group 1: 100% of necrosis (5/5); Group 2:20% (1/5); Group 3:80% (4/5). Injections of TRRE greatly reduced the ability of TNF to induce necrosis in Meth A tumors in BALB/c mice.

Since adding TRRE activity ablates the beneficial necrotizing activity of TNF, blocking endogenous TRRE activity would promote the beneficial effects of TNF.

Example 5

Nine New Polynucleotide Clones that Affect TRRE Activity

A number of cells have been found to express high levels of TRRE activity, especially after PMA stimulation. These include the cell lines designated THP-1, U-937, HL-60, ME-180, MRC-5, Raji, K-562. Jurkat cells have a high TRRE activity (850 TRRE U/mL at $10^{-2}$ PMA). In this experiment, the expression library of the Jurkat T cell (ATCC #TIB-152) was obtained and used to obtain 9 polynucleotide clones that augment TRRE activity.

Selection of expression sequences in the library was done by repeated cycles of transfection into COS-1 cells, followed by assaying of the supernatant as in Example 1 for the presence of activity cleaving and releasing the TNF receptor. Standard techniques were used in the genetic manipulation. Briefly, the DNA of $10^6$ Jurkat cells was extracted using an InVitrogen plasmid extraction kit according to manufacturer's directions. cDNA was inserted in the ZAP Express™/ EcoRI vector (cat. no. 938201, Stratagene, La Jolla Calif. The library was divided into 48 groups of DNA and transformed into COS-1 cells using the CaCl transfection method. Once the cells were grown out, the TRRE assay was performed, and five positive groups were selected. DNA from each of these five groups was obtained, and transfected into E. coli, with 15 plates per group. DNA was prepared from these cells and then transfected into COS-1 cells once more. The cells were grown out, and TRRE activity was tested again. Two positive groups were selected and transfected into E. coli, yielding 98 colonies. DNA was prepared from 96 of these colonies and transfected into COS-1 cells. The TRRE activity was performed again, and nine clones were found to substantially increase TRRE activity in the assay. These clones were designated 2-8, 2-9, 2-14, 2-15, P2-2, P2-10, P2-13, P2-14, and P2-15.

FIG. 4 is a bar graph showing the TRRE activity observed when the 9 clones were tested with C75 cells in the standard assay (Example 1).

These nine clones were then sequenced according to the following procedure:

1. Plasmid DNA was prepared using a modified alkaline lysis procedure.
2. DNA sequencing was performed using DyeDeoxy termination reactions (ABI). Base-specific fluorescent dyes were used as labels.
3. Sequencing reactions were analyzed on 5.75% Long Ranger™ gels by an ABI 373A-S or on 5.0% Long Ranger™ gels by an ABI 377 automated sequencer.
4. Subsequent data analysis was performed using Sequencher™ 3.0 software.

Standard primers T7X, T3X, −40, −48 Reverse, and BK Reverse (BKR) were used in sequencing reactions. For each clone, several additional internal sequencing primers (listed below) were synthesized.

NCBI BLAST (Basic Local Alignment Search Tool) sequence analysis (Altschul et al. (1990) *J. Mol. Biol.* 215:403–410) was performed to determine if other sequences were significantly similar to these sequences. Both the DNA sequences of the clones and the corresponding ORFs (if any) were compared to sequences available in databases.

The following clones were obtained and sequenced:

TABLE 1

DNA sequences affecting TRRE activity

| Clone | Sequence Designation | SEQ ID NO: | Approx. Length (bp) | Expression Designation | Related sequences (potential homology) |
|---|---|---|---|---|---|
| 2-9 | AIM2 | 1 | 4,047 | | — |
| 2-8 | AIM3T3 (partial sequence) | 2 | 739 | | *M. musculus* 45S pre-rRNA gene |
| | AIM3T7 (partial sequence) | 3 | 233 | | |
| 2-14 | AIM4 | 4 | 2,998 | Mey3 | human arfaptin 2 and others (see below) |
| 2-15 | AIM5 | 5 | 4,152 | | — |
| P2-2 | AIM6 | 6 | 3,117 | Mey5 | — |
| P2-10 | AIM7 | 7 | 3,306 | Mey6 | Human Insulin-like Growth factor II Receptor |
| P1-13 | AIM8 | 8 | 4,218 | | — |
| P2-14 | AIM9 | 9 | 1,187 | Mey8 | — |
| P2-15 | AIM10 | 10 | 3,306 | | E1b-55kDa-associated protein |

Clone 2-9 (AIM2): The internal primers used for sequencing are shown in SEQ. ID NOS:11–38. The sequence of AIM2 is presented in SEQ ID NO:1. The complementary strand of the AIM2 sequence is SEQ ID NO:147. The longest open reading frame (ORF) in the AIM2 sequence is 474 AA long and represented in SEQ ID NO:148.

Clone 2-8 (AIM3): Two partial sequences of length 739 and 233 were obtained and designated AIM3T3 and AIM3T7. The internal primers used for sequencing are shown in SEQ. ID NOS:39–46. The sequences of AIM3T3 and AIM3T7 are presented in SEQ ID NOs:2 and 3, respectively. The BLAST search revealed that the AIM3T3 sequence may be homologous to the mouse (*M. musculus*) 28S ribosomal RNA (Hassouna et al. *Nucleic Acids Res.* 12:3563–3583, 1984) and the *M. musculus* 45S pre-rRNA genes (Accession No. X82564. The complementary sequence of the AIM3T3 sequence showed 99% similarity over 408 bp beginning with nt 221 of SEQ ID NO:2 to the former and 97% similarity over the same span to the latter.

Clone 2-14 (AIM4). The internal primers used for sequencing are shown in SEQ. ID NOS:14–65. The sequence of AIM4 is presented in SEQ ID NO:4. The complementary strand of the AIM4 sequence is SEQ ID NO:149. The longest ORF in the AIM4 sequence is 236 AA long and represented in SEQ ID NO:150. AIM4 has significant alignments to human sequences arfaptin 2, ADE2H1 mRNA showing homologies to SAICAR synthetase, polypyrimidine tract binding protein (heterogeneous nuclear ribonucleoprotein I) mRNA, several PTB genes for polypyrimidine tract binding proteins, mRNA for por1 protein. Human arfaptin 2 is a putative target protein of ADP-ribosylation factor that interacts with RAC1 by binding directly to it. RAC1 is involved in membrane ruffling. Arfaptin 2 has possible transmembrane segments, potential CK2 phosphorylation sites, PKC phosphorylation site and RGD cell attachment sequence.

Clone 2-15 (AIM5): The internal primers used for sequencing are shown in SEQ. ID NOS:66–80. The sequence of AIM5 is presented in SEQ ID NO:5. The BLAST search revealed that the AIM5 sequence displays some similarity to Human Initiation Factor 5A (elF-5A) Koettnitz et al. (1995) *Gene* 159:283–284, 1995 and Human Initiation Factor 4D (elF 4D) Smit-McBride et al. (1989) *J. Biol. Chem.* 264:1578–1583, 1989.

Clone P2-2 (AIM6): The internal primers used for sequencing are shown in SEQ. ID NOS:81–93. The sequence of AIM6 is presented in SEQ ID NO:6. The longest ORF in the AIM6 sequence is 1038 AA long and represented in SEQ ID NO:151.

Clone P2-10 (AIM7): The internal primers used for sequencing are shown in SEQ. ID NOS:94–106. The sequence of AIM7 is presented as SEQ ID NO:7. The longest ORF in the AIM7 sequence is 849 AA long and represented in SEQ ID NO:152. The BLAST search revealed that this clone may be related to the Human Insulin-like Growth Factor II Receptor (Morgan et al. *Nature* 329:301–307, 1987 or the Human Cation-independent Mannose 6-Phosphate Receptor mRNA (Oshima et al. *J. Biol. Chem.* 263:2553–2562, 1988). The AIM7 sequence showed roughly 99% identity to both sequences over 2520 nucleotides beginning with nt 12 of SEQ ID NO:7 and 99% similarity to the latter over the same span.

Clone P2-13 (AIM8): The internal primers used for sequencing are shown in SEQ. ID NOS:107–118. The sequence of AIM8 is presented as SEQ ID NO:8. The longest ORF in the AIM8 sequence is 852 AA long and represented in SEQ ID NO:153.

Clone P2-14 (AIM9): The internal primers used for sequencing are shown in SEQ. ID NOS:119–124. The sequence of AIM9 is presented as SEQ ID NO:9. The longest ORF was about 149 amino acids in length.

Clone P2-15 (AIM10): The internal primers used for sequencing are shown in SEQ. ID NOS:125–146. The sequence of AIM10 is presented as SEQ ID NO:10. The longest ORF in the AIM10 sequence is 693 AA long and represented in SEQ ID NO:154. Sequence 10 on BLASTN search of non-redundant databases at NCBI aligns with Human mRNA for E1b-55 kDa-associated protein, locus HSA7509 (Accession AJ007509, NID g3319955).

Clonal DNA may be directly injected into test animals in order to test the ability of these nucleic acids to induce TRRE activity, counteract septic shock and/or affect tumor necrosis, as is described in detail in Examples 3 and 4. Alternatively, proteins or RNA can be generated from the clonal DNA for similar testing.

Example 6

Expression of Newly Obtained Clones

Example 5 describes 9 new clones which enhance TRRE activity in a cell surface assay system. The clones were obtained in the pBK-CMB Phagmid vector.

The following work was done on contract through the commercial laboratory Lark Technologies, Houston, Tex. The clones were removed from shuttle vectors and inserted into expression vectors in the following manner. Recombinant plasmid (pBK-CMV containing insert) was digested with appropriate restriction enzyme(s) such as Spe I, Xba I, EcoR I or others, as appropriate. The Baculovirus Transfer Vector (pAcGHLT-A Baculovirus Transfer Vector, PharMingen, San Diego, Calif., Cat. No. 21460P) was also cut with appropriate restriction enzyme(s) within or near the multiple cloning site to receive the insert removed from the shuttle vector.

The fragment of interest being subcloned was isolated from the digest using Low-Melting agarose electrophoresis and purified from the gel using a Qiaquick Gel Extraction Kit following Lark SOP MB 020602. If necessary, the receiving vector was treated with alkaline phosphatase according to Lark SOP MB 090201. The fragment was ligated into the chosen site of the vector pAcGHLT-A. The recombinant plasmid was transformed into *E. coli* XL1 Blue MRF' cells and the transformed bacterial cells were selected on LB agar plates containing ampicillin (100 µg/ml). Ampicillin resistant colonies were picked and grown on LB broth containing ampicillin for plasmid preparation.

Plasmid DNA was prepared using Alkaline Minilysate Procedure (Lark SOP MB 010802 and digested with appropriate restriction enzyme(s). Selected subclones were confirmed to be of the correct size. Subclones were digested with other appropriate restriction enzyme(s) to ascertain correct orientation of the insert by confirming presence of fragments of proper size(s). A subclone was grown in 100 ml of LB broth containing ampicillin (100 µg/ml) and the plasmid DNA prepared using Qiagen Midi Plasmid Preparation Kit (Lark SOP MB 011001). The DNA concentration was determined by measuring the absorbance at 260 nm and the DNA sample was verified to be originated from correct subclone by restriction digestion.

Thus were produced the expression constructs for Mey3, Mey5, Mey6, Mey8 now with the coding sequence of interest fused to GST gene with polyhistitidine tag, protein kinase A site and thrombin cleavage site. The GST gene and now the fusion protein are under the polyhedrin promotor. PharMingen (San Diego, Calif.) incorporated the vector with insert into functional baculovirus particles by co-inserting the transfer vector (pAcGHLT) into susceptible insect cell line S along with linearized virus DNA (PharMingen, San Diego, Calif., BaculoGold viral DNA, Cat. No. 21100D). The functional virus particles were grown again on the insect cells to generate a high titer stock. Protein production was then done by infecting a large culture of cells in Tini cell. The cells were harvested when the protein yield reached a maximum and before the virus killed the cells. Fusion proteins were collected on a glutatione-agarose column, washed and released with glutathionine.

Proteins collected from the affinity column were quantified by measuring $OD_{280}$ and were assayed on gels using SDS-PAGE and Western blotting with labeled anti-GST (PharMingen, San Diego, Calif., mAbGST Cat. No. 21441A) to confirm that all the bands present included the GST portion.

Four of the ten sequences have been cloned, expressed in bacculovirus infected insect cells, and then purified.

TABLE 2

Expressed protein from Jurkat library clones

| Name | Sequence in insert | Amount of protein (mg/mL) |
| --- | --- | --- |
| Mey3 | AIM4 | 4.7, 5.0 |
| Mey5 | AIM6 | 1.36, 1.50 |
| Mey6 | AIM7 | 0.33 |
| Mey8 | AIM9 | 1.53 |

Gels indicated the presence of the GST protein in addition to larger proteins that were also positive with the anti-GST antibody in Western analyses. Mey3 repeatedly exhibited the presence of proteins around 32 kDa, 56 kDa, bands around 60–70 kDa and another larger than 70 kDa. Mey5 consistently had proteins migrating as approximately 34 kDa, 38 kDa, 58 kDa, around 60–70 kDa, and others larger than 70 kDa. Mey6 had protein bands around 34 kDa, 56 kDa, 58 kDa, and bands around 60–70 kDa. Mey8 had protein bands around 36 kDa, 58 kDa and bands around 60–70 kDa. All of the indicated bands were positive for GST. The bands may represent the desired fusion protein or degradation/cleavage product generated during growth and purification.

Example 7

Assay of Expression Products for Effect on TNF-R Cleaving Activity

The following method was used to measure TRRE activity of Mey 3, 5, 6 and 8. C75R cells and COS-1 cells were seeded into 24-well culture plates at a density of $2.5 \times 10^5$ cells/ml/well and incubated overnight (for 12 to 16 hours) in 5% $CO_2$ at 37° C. After aspirating the medium in the well, 300 μl of 1 ug of Mey 3, 5 and 8 were incubated in each well of both the C75R and COS-1 plates for 30 min in 5% $CO_2$ at 37° C. (corresponding to A and C mentioned below, respectively). Simultaneously, C75R cells in 24-well plates were also incubated with 300 μl of fresh medium or buffer (corresponding to B mentioned below). The supernatants were collected, centrifuged, and then assayed for the concentration of soluble p75 TNF-R by ELISA as described in Example 1.

The following results were obtained:

TABLE 3

Enzymatic activity of expressed clones

| Clone No. | TNF-receptor releasing activity U/mg |
| --- | --- |
| Mey-3 | 341 |
| Mey-5 | 671 |
| Mey-6 | 452 |
| Mey-8 | 191 |

Example 8

Effectiveness of Expression Products in Treating Septic Shock

The protocol outlined in Example 3 was used to test the effects of the expression products from the new clones in preventing mortality in the septic shock model.

Different amounts of recombinant Mey 3, 5, and 8 (10–100 ug/mouse) were injected i.v. in a 0.05 ml volume within an hour prior to or after injection of a lethal dose of LPS. Serum (0.1 ml) was collected using a 27 gauge needle and 1 ml syringe from the tail vein at 30, 60 and 90 minutes after LPS injection. This serum was heparinized and stored frozen at −20° C. Samples from multiple experiments were tested by ELISA for the presence of solubilized TNR-R, the TNR ligand, IL-8, and IL-6. Animals were monitored over the next 12 hours for the clinical effects of shock. Selected animals were euthanized from 3 to 12 hours after treatment, autopsied and various organs and tissues fixed in formalin, imbedded in paraffin, sectioned and stained by hematoxalin-eosin (H and E). Tissue sections were subjected to histopathologic and immunopathologic examination.

FIG. 5 shows the results obtained. (♦) saline; (■) BSA; (Δ) Mey-3 (100 μg); (X) Mey-3 (10 μg); (*) Mey-5 (10 μg); (●) Mey-8 (10 μg).

Mice injected with LPS alone or LPS, a control buffer or control protein (BSA) died rapidly. All of the animals in this group were dead at 24 hours. In contrast, when injections of LPS were accompanied by injections of a 10–100 ug of Mey 3, 5 and 8, death was delayed and death rates were lower. None of the animal were dead at 24 hours that had been treated with Mey 3 and Mey 5. Only 66% of the animals were dead at 24 hours that had been treated with Mey 8. Thus, Mey 3, 5 and 8 were able to counteract the mortality induced by LPS in test animals.

What is claimed as the invention is:

1. A method of screening a substance for an ability to affect TNF receptor releasing activity, comprising:
   a) incubating TNF receptor or cells expressing TNF receptor with the substance and with an isolated polypeptide that causes TNF receptor to be cleaved in the absence of the substance;
   b) measuring any TNF receptor cleaved; and
   c) correlating any increase or decrease of the receptor cleaved by the polypeptide with an ability of the substance to enhance or diminish TNF receptor releasing activity; wherein the polypeptide has at least one of the following properties:
   i) it comprises an amino acid sequence selected from SEQ. ID NOs: 151, 153, and 154;
   ii) it comprises a fragment of any one of SEQ. ID NOs: 151, 153, or 154 that causes increased release of TNF receptor from human cells in which TNF receptor is expressed;
   iii) it comprises an amino acid sequence encoded in any one of SEQ. ID NOs: 1, 5, 6, 8, 9, or 10; or
   iv) it comprises an amino acid sequence that causes increased release of TNF receptor from human cells in which TNF receptor is expressed, and is encoded by a polynucleotide that hybridizes-at 30° C. in 6×SSC containing 50% formamide to a polynucleotide having a sequence selected from SEQ. ID NOs : 1, 5, 6, 8, 9, or 10.

2. The screening method of claim 1, wherein the polypeptide contains SEQ. ID NOs: 147–149, 151, or 153–154, or fragment thereof which causes increased release of TNF receptor from human cells in which TNF receptor is expressed.

3. The screening method of claim 1, wherein the polypeptide has at least one of the following properties:
   i) it comprises a sequence encoded in the longest open reading frame of SEQ. ID NOs: 1, 5, 6, 8, 9, or 10 or fragment of any of these sequences; or
   ii) it is encoded by a polynucleotide that hybridizes at 30° C. in 6×SSC containing 50% forniamide to a polynucleotide having a sequence selected from SEQ. ID NOs: 1, 5, 6, 8, 9, or 10.

wherein the polypeptide causes increased release of TNF receptor from human cells in which TNF receptor is expressed.

4. The screening method of claim 1, wherein the polypeptide has been obtained by purifying TRRE from human cells that express it endogenously.

5. The screening method of claim 1, wherein the polypeptide has been obtained by expressing a recombinant polynucleotide.

6. The screening method of claim 1, wherein the polypeptide has metalloprotease activity.

7. The screening method of claim 3, wherein the polynucleotide comprises a sequence selected from the longest open reading frame of SEQ. ID NOs: 1, 5, 6, 8, 9, or 10, or a fragment of any of these sequences.

8. The screening method of claim 3, wherein the polynucleotide hybridizes at 30° C. in 6×SSC containing 50% formamide to a polynucleotide having a sequence selected from SEQ. ID NOs: 1, 5, 6, 8, 9, or 10, or a fragment of any of these sequences.

9. The screening method of claim 3, wherein the polynucleotide comprises the sequence of the longest open reading frame of SEQ. ID NO:1 or fragment thereof.

10. The screening method of claim 3, wherein the polynucleotide comprises the sequence of the longest open reading frame of SEQ. ID NO:5 or fragment thereof.

11. The screening method of claim 3, wherein the polynucleotide comprises the sequence of the longest open reading frame of SEQ. ID NO:6 or fragment thereof.

12. The screening method of claim 3, wherein the polynucleotide comprises the sequence of the longest open reading frame of SEQ. ID NO:8 or fragment thereof.

13. The screening method of claim 3, wherein the polynucleotide comprises the sequence of the longest open reading frame of SEQ. ID NO:9 or fragment thereof.

14. The screening method of claim 3, wherein the polynucleotide comprises the sequence of the longest open reading frame of SEQ. ID NO:10 or fragment thereof.

15. The screening method of claim 1, wherein the polynucleotide hybridizes at 30° C. in 6×SSC containing 50% formamide to a polynucleotide having the sequence of SEQ. ID NO:1.

16. The screening method of claim 1, wherein the polynucleotide hybridizes at 30° C. in 6×SSC containing 50% formamide to a polynucleotide having the sequence of SEQ. ID NO:5.

17. The screening method of claim 1, wherein the polynucleotide hybridizes at 30° C. in 6×SSC containing 50% formamide to a polynucleotide having the sequence of SEQ. ID NO:6.

18. The screening method of claim 1, wherein the polynucleotide hybridizes at 30° C. in 6×SSC containing 50% formamide to a polynucleotide having the sequence of SEQ. ID NO:8.

19. The screening method of claim 1, wherein the polynucleotide hybridizes at 30° C. in 6×SSC containing 50% formamide to a polynucleotide having the sequence of SEQ. ID NO:9.

20. The screening method of claim 1, wherein the polynucleotide hybridizes at 30° C. in 6×SSC containing 50% formamide to a polynucleotide having the sequence of SEQ. ID NO: 10.

21. The screening method of claim 1, wherein the substance is incubated with p55 TNF receptor in step a).

22. The screening method of claim 1, wherein the substance is incubated with p75 TNF receptor in step a).

23. The screening method of claim 1, wherein the substance is incubated with a cell expressing p55 TNF receptor in step a).

24. The screening method of claim 1, wherein the substance is incubated with a cell expressing p75 TNF receptor in step a).

25. The screening method of claim 1, wherein the measuring of TNF receptor cleaved in step b) comprises measuring binding capacity for TNF on the surface of the treated cell.

26. The screening method of claim 1, wherein the measuring of TNF receptor cleaved in step b) comprises measuring the concentration of soluble TNF receptor in culture medium from the treated cell.

27. The screening method of claim 1, wherein the polypeptide comprises SEQ. ID NO:151 or fragment thereof.

28. The screening method of claim 1, wherein the polypeptide comprises SEQ. ID NO:153 or fragment thereof.

29. The screening method of claim 1, wherein the polypeptide comprises SEQ. ID NO:154 or fragment thereof.

* * * * *